US012807602B2

(12) United States Patent
Wernke et al.

(10) Patent No.: US 12,807,602 B2
(45) Date of Patent: Nov. 24, 2026

(54) COLIBACTIN DERIVATIVES AND METHODS OF TREATING, AMELIORATING, AND/OR PREVENTING CANCER

(71) Applicant: Yale University, New Haven, CT (US)

(72) Inventors: Kevin Wernke, New Haven, CT (US); Seth Herzon, New Haven, CT (US)

(73) Assignee: Yale University, New Haven, CT (US)

( * ) Notice: Subject to any disclaimer, the term of this patent is extended or adjusted under 35 U.S.C. 154(b) by 323 days.

(21) Appl. No.: 18/690,129

(22) PCT Filed: Sep. 8, 2022

(86) PCT No.: PCT/US2022/042846
§ 371 (c)(1),
(2) Date: Mar. 7, 2024

(87) PCT Pub. No.: WO2023/039027
PCT Pub. Date: Mar. 16, 2023

(65) Prior Publication Data

US 2025/0026747 A1 Jan. 23, 2025

Related U.S. Application Data

(60) Provisional application No. 63/242,368, filed on Sep. 9, 2021.

(51) Int. Cl.

| | |
|---|---|
| ***C07D 417/14*** | (2006.01) |
| ***A61K 31/403*** | (2006.01) |
| ***A61K 31/427*** | (2006.01) |
| ***A61P 35/00*** | (2006.01) |
| ***C07D 403/14*** | (2006.01) |

(52) U.S. Cl.

CPC .......... *C07D 417/14* (2013.01); *A61K 31/403* (2013.01); *A61K 31/427* (2013.01); *A61P 35/00* (2018.01); *C07D 403/14* (2013.01)

(58) Field of Classification Search

None

See application file for complete search history.

(56) References Cited

U.S. PATENT DOCUMENTS

2019/0031650 A1 1/2019 Herzon et al.

OTHER PUBLICATIONS

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

International Search Report and Written Opinion for International Application No. PCT/US2022/042846 issued on Jan. 4, 2023.

Herzon "Macrocyclic colibactins." Nature chemistry 12.11 (2020): 1005-1006.

Williams, et al. "Employing chemical synthesis to study the structure and function of colibactin, a "dark matter" metabolite." Natural product reports 37.11 (2020): 1532-1548.

Wernke, et al. "Structure and bioactivity of colibactin." Bioorganic & medicinal chemistry letters 30.15 (2020): 127280.

* cited by examiner

*Primary Examiner* — Po-Chih Chen

(74) *Attorney, Agent, or Firm* — Saul Ewing LLP; Kathryn Doyle; Domingos J. Silva

(57) ABSTRACT

Described herein is a stable colibactin derivative, or a salt, solvate, isotopically labelled derivative, stereoisomer, tautomer, or geometric isomer thereof, or any mixtures thereof. Also described herein is a method of alkylating a DNA molecule, a method of forming a DNA interstrand cross-link (ICL), as well as a method of preventing, treating, and/or ameliorating cancer.

17 Claims, 17 Drawing Sheets colibactin 771 (1a)

• structure of colibactin based on biosynthetic analysis
• undetectable in bacterial cultures colibactin 769 (2a), X = NH
colibactin 770 (3a), X = O

• not isolated
• unstable in cell culture
• difficult to prepare in homogenous form colibactin 742 (4a)

• indefinitely stable in cell culture
• readily-prepared on >100 mg scale

5 or 6

7; 51% from 5
49% from 6

8a X = $NH_2$; 42% from 5
8b X = OH; 25% from 6

15, 16, 18, 14, 19, 20, 13, 21, 12, 17, 11, 10 linear precursor 9 chain isomer 4a ring isomer 4b colibactin 742 (4) | 1:8 mixture of 4a/4b

4b no deuterium incorporation observed at C44 after heating in methanol-$d_4$ or aqueous $K_2DPO_4$ (containing 50% methanol-$d_4$, v/v) at 37 °C, 75 min

22

23

24
(1.3:1 mixture of C41 diastereomers)

| | DMSO | | | | | 9 | | | | | 4 | | | | | MMC | | | | |
|---|---|---|---|---|---|---|---|---|---|---|---|---|---|---|---|---|---|---|---|---|
| cell stage | Sub-G1 | G1 | S | G2 | >4N | Sub-G1 | G1 | S | G2 | >4N | Sub-G1 | G1 | S | G2 | >4N | Sub-G1 | G1 | S | G2 | >4N |
| % | 8.4 | 32.9 | 7.6 | 30.1 | 11.0 | 4.4 | 10.6 | 19.2 | 56.9 | 8.9 | 3.7 | 6.2 | 18.0 | 63.6 | 8.5 | 3.3 | 7.7 | 16.7 | 61 | 11.3 |

9

4a

25

4b

1b

2b, X = NH
3b, X = O

9
% dead cells
Concentration [μM]
9 IC$_{50}$ = 7.2 ± 1.7 μM colibactin 742 (4)
% dead cells
Concentration [μM]
KW-383 IC$_{50}$ = 5.2 ± 2.1 μM 22
% dead cells
Concentration [μM]

23
% dead cells
Concentration [μM]
23 IC$_{50}$ = 8.4 ± 2.4 μM

24
% dead cells
Concentration [μM]

| | 100 μM | | | | | 33 μM | | | | | 3.7 μM | | | | | 1.2 μM | | | | |
|---|---|---|---|---|---|---|---|---|---|---|---|---|---|---|---|---|---|---|---|---|
| cell stage | Sub-G1 | G1 | S | G2 | >4N | Sub-G1 | G1 | S | G2 | >4N | Sub-G1 | G1 | S | G2 | >4N | Sub-G1 | G1 | S | G2 | >4N |
| % | 2.0 | 5.1 | 20.6 | 59.4 | 12.9 | 3.1 | 5.6 | 29.9 | 51.1 | 10.3 | 9.0 | 25.7 | 14.0 | 43.9 | 7.4 | 9.9 | 36.7 | 14 | 30.2 | 9.2 |

| | 100 μM | | | | | 33 μM | | | | | 3.7 μM | | | | | 1.2 μM | | | | |
|---|---|---|---|---|---|---|---|---|---|---|---|---|---|---|---|---|---|---|---|---|
| cell stage | Sub-G1 | G1 | S | G2 | >4N | Sub-G1 | G1 | S | G2 | >4N | Sub-G1 | G1 | S | G2 | >4N | Sub-G1 | G1 | S | G2 | >4N |
| % | 2.4 | 6.1 | 25.4 | 52.9 | 13.2 | 2.7 | 4.8 | 19.7 | 63.0 | 9.9 | 7.5 | 19.3 | 11.6 | 53.7 | 7.8 | 9.2 | 38.6 | 14.0 | 29.8 | 8.4 |

COLIBACTIN DERIVATIVES AND METHODS OF TREATING, AMELIORATING, AND/OR PREVENTING CANCER

CROSS-REFERENCE TO RELATED APPLICATIONS

The present application is a 35 U.S.C. § 371 national phase application from, and claims priority to, International Application No. PCT/US2022/042846, filed Sep. 8, 2022, which claims priority under 35 U.S.C. § 119(e) to U.S. Provisional Patent Application No. 63/242,368, filed Sep. 9, 2021, all of which are incorporated herein by reference in their entireties.

STATEMENT REGARDING FEDERALLY SPONSORED RESEARCH

This invention was made with government support under CA215553 and GM067543 awarded by National Institutes of Health. The government has certain rights in the invention.

BACKGROUND

Colibactin is a genotoxic hybrid polyketide-non-ribosomal peptide secondary metabolite possessing two electrophilic warheads, which promotes interstrand cross-links (ICLs) in DNA through a cyclopropane ring-opening mechanism. The biosynthesis of colibactin is encoded in the clb (aka pks) biosynthetic gene cluster, which is widely distributed in Enterobacteriaceae, including certain commensal and pathogenic *E. coli*. $clb^+$ Bacteria are overrepresented in patients with colorectal cancer and genomic studies have revealed a causal link between clb genotoxicity and tumorigenesis in humans. Indeed, $clb^+$ bacteria induce tumorigenesis in models of intestinal inflammation and have been causally linked to oncogenesis in human tumors.

It follows that understanding colibactin's molecular mechanism of action and genotoxic effects will facilitate cancer prevention, detection, and treatment strategies. Studying colibactin directly, however, has not been possible due to the compound's low production level and overall instability.

Therefore, there is a need in the art to synthesize stable derivatives of colibactin that still possess the colibactin's chemical reactivity and biological activity. There is a further need in the art for novel antitumor agents, which can be used to treat, ameliorate, and/or prevent cancer in a subject. The instant application addresses these needs.

SUMMARY

In some aspects, the present invention is directed to the following non-limiting embodiments:

In some embodiments, the present invention is directed to a compound of Formula (I):

A1-B-A2 (I), or a salt, solvate, isotopically labelled derivative, stereoisomer, tautomer, or geometric isomer thereof, or a mixture thereof.

In some embodiments, in Formula (I), A1 and A2 are each independently selected from the group consisting of

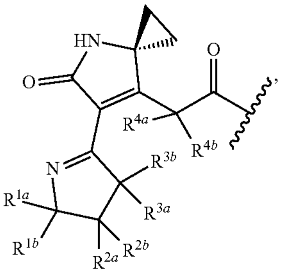

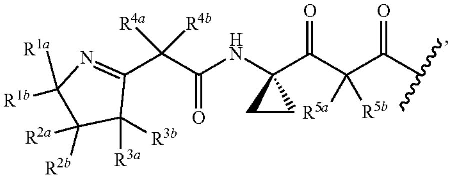

and

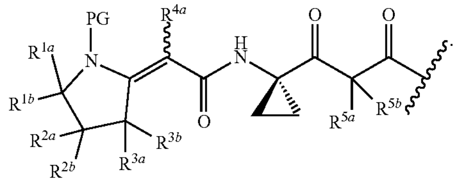

In some embodiments, in Formula (I), B is a bifunctional group selected from the group consisting of:

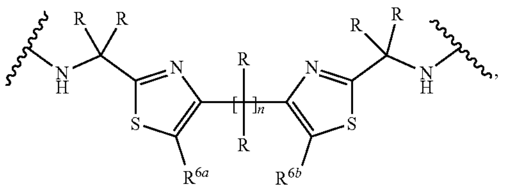

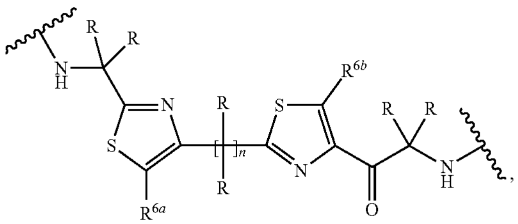

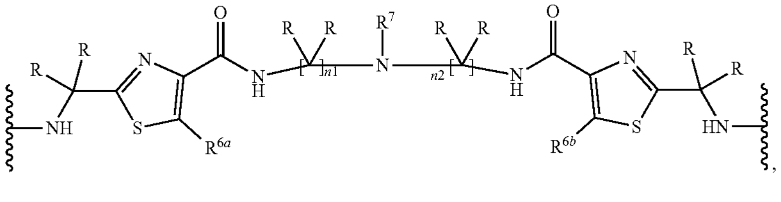

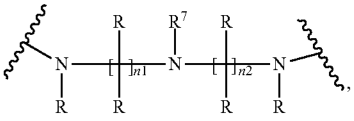

and

-continued

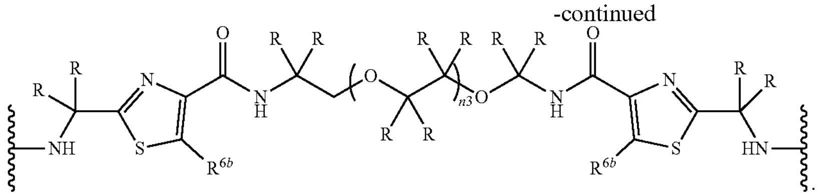

In some embodiments, each occurrence of $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl.

In some embodiments, $R^7$ is selected from the group consisting of hydrogen, optionally substituted $C_1$-$C_6$ alkyl, optionally substituted $C_3$-$C_6$ cycloalkyl, optionally substituted $C_2$-$C_6$ cycloalkenyl, and optionally substituted $C_2$-$C_6$ cycloalkynyl.

In some embodiments, PG is a protective group selected from the group consisting of tert-butoxycarbonyl (Boc), trityl, dimethoxytrityl, tert-butyldimethylsilyl (TBDMS), carboxybenzyl (Cbz), nitroveratryloxycarbonyl (Nvoc), aryldithioethyloxycarbonyl (Ardec), (9H-fluoren-9-yl) methyl ((S)-1-(((S)-1-((4-(hydroxymethyl)phenyl)amino)-1-oxo-5-ureidopentan-2-yl)amino)-3-methyl-1-oxobutan-2-yl) carbamate (Fmoc-Val-Cit-PAB) and derivates thereof.

In some embodiments, each occurrence of R is independently H and optionally substituted $C_1$-$C_6$ alkyl.

In some embodiments, each occurrence of n, n1, and n2 is independently an integer ranging from 2 to 6.

In some embodiments, each occurrence of n3 is independently an integer ranging from 1 to 6.

In some embodiments, A1 and A2 are each independently selected from the group consisting of

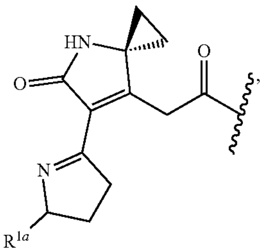

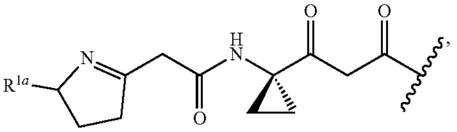

and

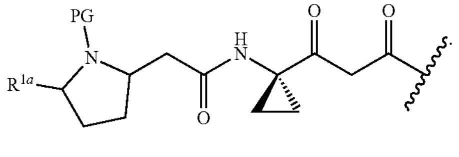

In some embodiments, A1 and A2 are each independently selected from the group consisting of:

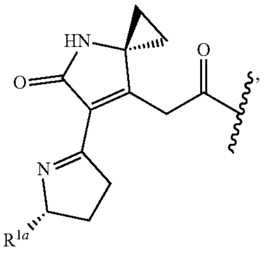

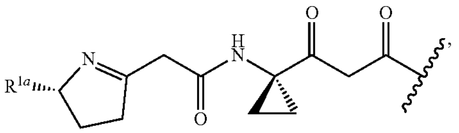

and

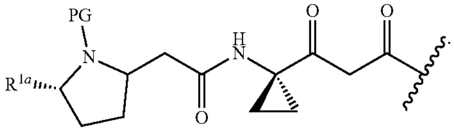

In some embodiments, A is

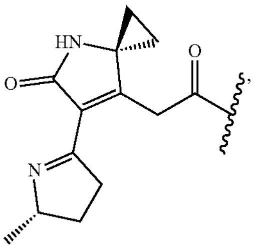

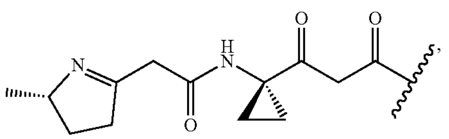

or

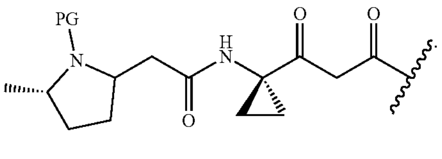

In some embodiments, the compound is at least one selected from the group consisting of:

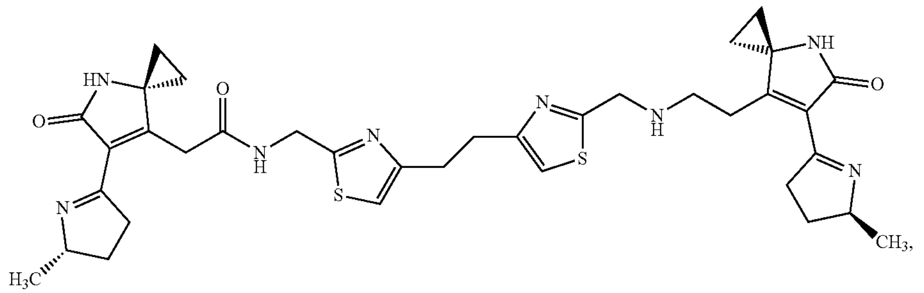
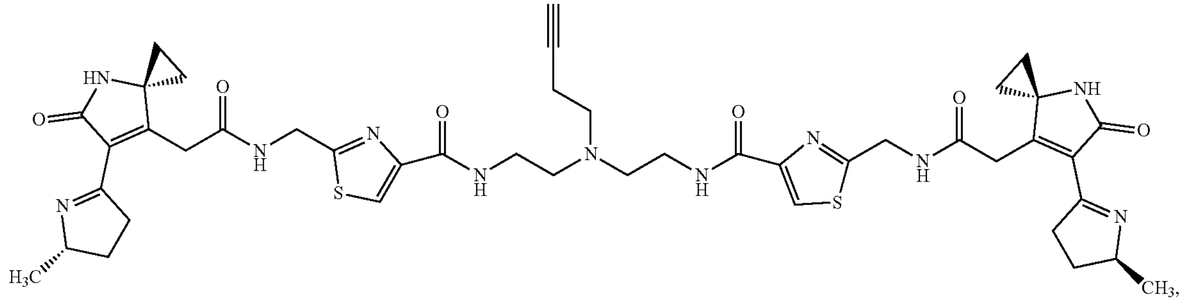
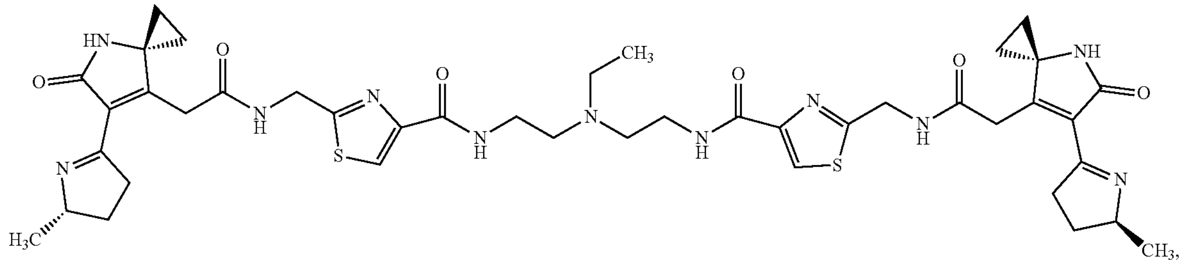
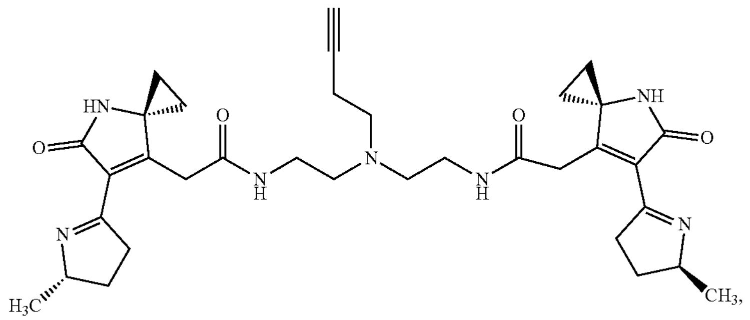
and
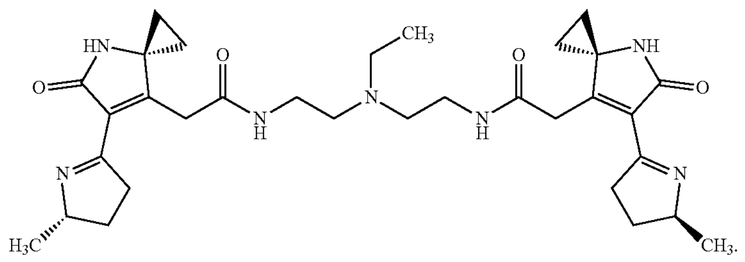
In some embodiments, the compound is capable of alkylating a DNA molecule.
In some embodiments, the compound is capable of forming an interstrand cross-link in a DNA molecule.
In some aspects, the present invention is directed to a compound of Formula (II):

(II)

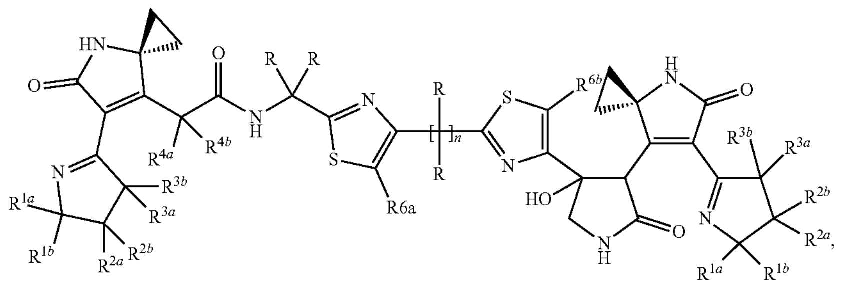

or a salt, solvate, isotopically labelled derivative, stereoisomer, tautomer, or geometric isomer thereof, and any mixtures thereof.

In some embodiments, each occurrence of $R^{1a}$, $R^{1b}$, $R^{2a}$, $R^{2b}$, $R^{3a}$, $R^{3b}$, $R^{4a}$, $R^{4b}$, $R^{6a}$, and $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl.

In some embodiments, each occurrence of R is independently H and optionally substituted $C_1$-$C_6$ alkyl.

In some embodiments, n is independently an integer ranging from 2 to 6.

In some embodiments, the compound is

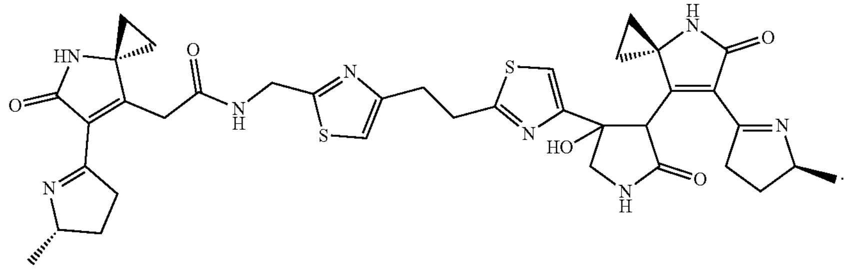

In some aspects, the present invention is directed to a method of alkylating a DNA molecule, the method comprising contacting the DNA molecule with the compound represented by Formula (I), or a salt, solvate, isotopically labelled derivative, stereoisomer, tautomer, or geometric isomer, or mixtures thereof.

In some embodiments, alkylating the DNA molecule comprising forming a DNA interstrand cross-link in the DNA molecule.

In some embodiments, the contacting is performed at a pH ranging from about 5.0 to 7.0.

In some embodiments, the DNA molecule is genomic DNA of a cell in a nucleus of the cell.

In some embodiments, the cell is a cancer cell.

In some aspects, the present invention is directed to a method of preventing, treating, and/or ameliorating cancer in a subject in need thereof, the method comprising administering to the subject an effective amount of the compound of Formula (I), or a salt, solvate, isotopically labelled derivative, stereoisomer, tautomer, or geometric isomer, or mixtures thereof.

In some embodiments, the compound is administered as a pharmaceutical composition comprising a pharmaceutically acceptable carrier.

In some embodiments, the cancer comprises at least one of cervical cancer, breast cancer, urinary tract cancer, and gastrointestinal cancer.

BRIEF DESCRIPTION OF THE DRAWINGS

The following detailed description of exemplary embodiments will be better understood when read in conjunction with the appended drawings. For the purpose of illustrating, non-limiting embodiments are shown in the drawings. It should be understood, however, that the instant specification is not limited to the precise arrangements and instrumentalities of the embodiments shown in the drawings.

FIG. 1A shows that the biosynthetic analysis and the characterization of clb intermediates indicate colibactin contains an α-aminoketone between two thia-zole rings, as in colibactin 771 (1a). However, this species has never been observed due to its facile oxidation to the 1,2-iminoketone colibactin 769 (2a), and subsequent hydrolysis to the diketone colibactin 770 (3a). The C36-descarbonyl-C37-desamino derivative colibactin 742 (4a) was envisioned to possess higher stability. FIG. 1B shows that the model systems 5 and 6 undergo cleavage of the central car-bon-carbon bond under mildly basic conditions, to form 7 and 8a/8b.

FIG. 3A depicts the synthesis of the aldehyde 14.

FIG. 3B depicts the synthesis of the thiazole 12 and its elaboration to 4a and 4b.

FIG. 6A depicts the DNA cross-linking comparison of colibactin 770 (3a), stable colibactin 742 (4), and its linear precursor 9 at pH 5.0. FIG. 6B depicts the comparison of the relative DNA cross-linking abilities of colibactin 742 (4) and its linear precursor 9 at pH 5.0. FIG. 6C depicts the comparison of the relative DNA cross-linking abilities of colibactin 742 (4) and its linear precursor 9 at pH 7.0.

FIG. 7A shows the evaluation of FANCD2 or γH2AX activation in cells treated with 4 or 9. HeLa cells were treated with the linear precursor 9 (1-100 μM), colibactin 742 (4) (1-100 μM) or MMC (150 nM) for 4 h. The cells were then washed and incubated for 20 h before immunofluorescence imaging. Cells were considered positive when >5 FANCD2 or γH2AX foci formed. Means and standard deviations of results from at least three independent experiments are shown. FIG. 7B depicts the DNA content histograms upon treatment with colibactin 742 (4, 11 μM) or 9 (11 μM) quantification of the sub-population of the histograms.

FIGS. 12A-12E show the results of the Cell viability assays. Specifically, HeLa cells were incubated with: (FIG. 12A) compound 9; (FIG. 12B) colibactin 742 (4); (FIG. 12C) compound 22; (FIG. 12D) compound 23; or (FIG. 12E) compound 24 at 24 nM-100 μM for 72 h, according some embodiments. The cells were then incubated with CTG reagent and the luminescence was measured. Results were normalized to DMSO control (0.1%, 0% effect) tamoxifen (60 μM, 100% effect). The points are the averages of twelve measurements (triplicates of four). The lines are four parameters logistic regression (4PL) fit. Error bars represent 95% confidence ranges.

DETAILED DESCRIPTION

Figure 1A:
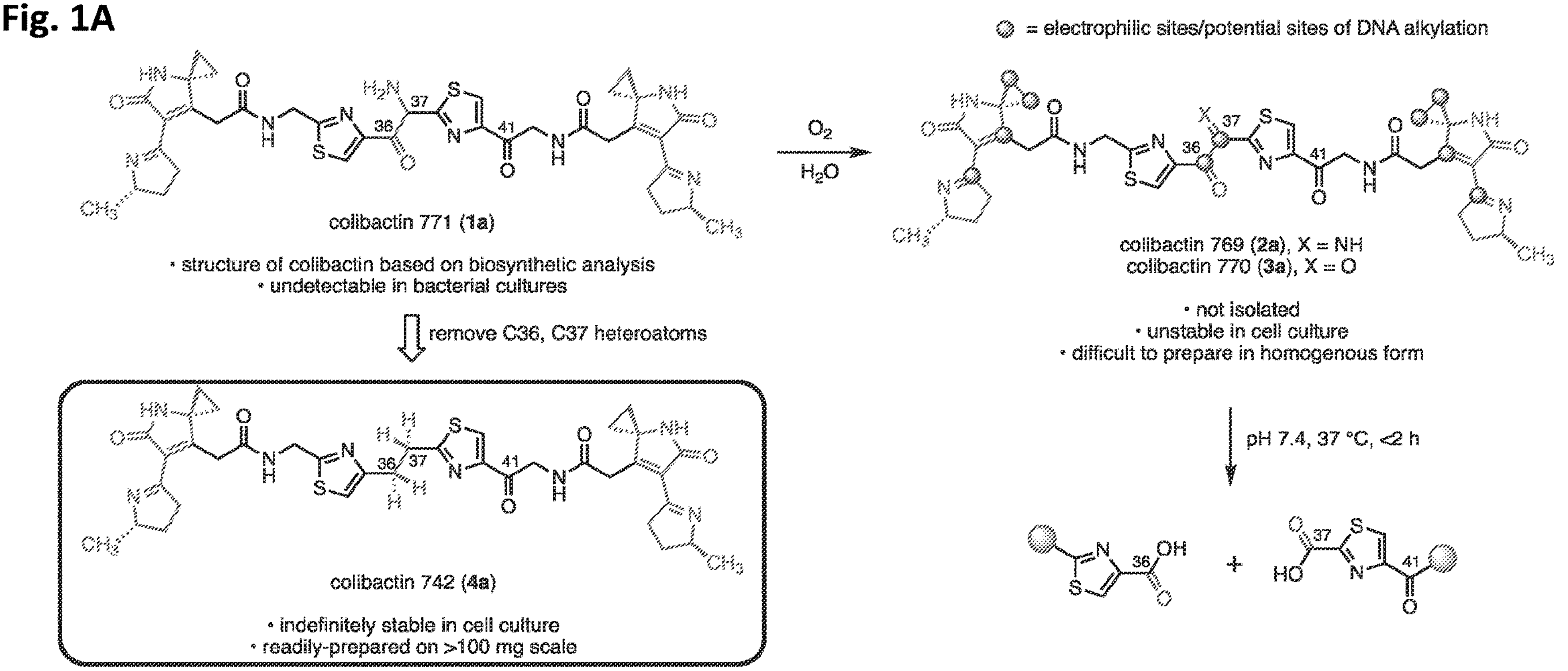
FIGS. 1A-1B depict the structure, instability, and DNA reactivity of colibactins according to some embodiments.

The following disclosure provides many different embodiments, or examples, for implementing different features of the provided subject matter. Specific examples of components and arrangements are described below to simplify the instant specification. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the instant specification may repeat reference numerals and/or letters in the various examples. This repetition is for the purpose of simplicity and clarity and does not in itself dictate a relationship between the various embodiments and/or configurations discussed.

As detailed elsewhere herein, the study as described in the instant specification identified and synthesized stable derivatives of colibactins. The instant study showed that the stable colibactins derivatives are capable of alkylating DNA molecules, and forming DNA interstrand cross-links. Furthermore, the instant study shows that the stable colibactins derivatives are able to induce cell death in cancer cells.

Therefore, in come embodiments, the instant specification is directed to a derivative of colibactins. In some embodiments, the instant specification is directed to a method of alkylating DNA molecules, or a method of forming DNA interstrand cross-links. In some embodiments, the instant specification is directed to a method of preventing, treating, and/or ameliorating cancer in a subject in need thereof.

Definitions

As used herein, each of the following terms has the meaning associated with it in this section. Unless defined otherwise, all technical and scientific terms used herein generally have the same meaning as commonly understood by one of ordinary skill in the art to which the instant specification belongs. Generally, the nomenclature used herein and the laboratory procedures in animal pharmacology, pharmaceutical science, peptide chemistry, and organic chemistry are those well-known and commonly employed in the art. It should be understood that the order of steps or order for performing certain actions is immaterial, so long as the instant specification remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

"About" as used herein when referring to a measurable value such as an amount, a temporal duration, and the like, is meant to encompass variations of ±20% or ±10%, in some embodiments ±5%, in some embodiments ±1%, in some embodiments ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

In one aspect, the terms "co-administered" and "co-administration" as relating to a subject refer to administering to the subject a compound and/or composition of the instant specification along with a compound and/or composition that may also treat or prevent a disease or disorder contemplated herein. In some embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "pharmaceutical composition" or "composition" refers to a mixture of at least one compound useful within the instant specification with a pharmaceutically acceptable carrier. The pharmaceutical composition facilitates administration of the compound to a patient. Multiple techniques of administering a compound exist in the art including, but not limited to, subcutaneous, intravenous, oral, aerosol, inhalational, rectal, vaginal, transdermal, intranasal, buccal, sublingual, parenteral, intrathecal, intragastrical, ophthalmic, pulmonary, and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the instant specification within or to the patient such that it may perform its intended function. Each carrier must be "acceptable" in the sense of being compatible with the other ingredients of the formulation, including the compound useful within the instant specification, and not injurious to the patient. Some examples of materials that may serve as pharmaceutically acceptable carriers include: sugars, such as lactose, glucose and sucrose; starches, such as corn starch and potato starch; cellulose, and its derivatives. As used herein, "pharmaceutically acceptable carrier" also includes any and all coatings, antibacterial and antifungal agents, and absorption delaying agents, and the like that are compatible with the activity of the compound useful within the instant specification, and are physiologically acceptable to the patient. The "pharmaceutically acceptable carrier" may further include a pharmaceutically acceptable salt of the compound useful within the instant specification. Other additional ingredients that may be included in the pharmaceutical compositions used in the practice of the instant specification are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, a "pharmaceutically effective amount," "therapeutically effective amount," or "effective amount" of a compound is that amount of compound that is sufficient to provide a beneficial effect to the subject to which the compound is administered.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In some embodiments, the subject is human.

As used herein, the term "treatment" or "treating" is defined as the application or administration of a therapeutic agent, i.e., a compound useful within the instant specification (alone or in combination with another pharmaceutical agent), to a patient, or application or administration of a therapeutic agent to an isolated tissue or cell line from a patient (e.g., for diagnosis or ex vivo applications), who has a disease or disorder and/or a symptom of a disease or disorder, with the purpose to cure, heal, alleviate, relieve, alter, remedy, ameliorate, improve or affect the disease or disorder and/or the symptoms of the disease or disorder. Such treatments may be specifically tailored or modified, based on knowledge obtained from the field of pharmacogenomics.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_6$) alkyl, such as, but not limited to, ethyl, methyl, isopropyl, isobutyl, n-pentyl, n-hexyl, and cyclopropylmethyl.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by $—CH_2—CH=CH_2$.

As used herein, the term "alkynyl," employed alone or in combination with other terms, means, unless otherwise stated, refers to a straight-chain or branched hydrocarbon residue having a carbon-carbon triple bond and have the number of carbon atoms designated (i.e., $C_1$-$C_{10}$ means one to ten carbon atoms) and includes straight, branched chain, or cyclic substituent groups.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is ($C_1$-$C_3$) alkoxy, such as, but not limited to, ethoxy and methoxy.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$) cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, the term "halo" or "halogen" alone or as part of another substituent refers to, unless otherwise stated, a fluorine, chlorine, bromine, or iodine atom.

As used herein, the term "substituted" refers to that an atom or group of atoms has replaced hydrogen as the substituent attached to another group.

As used herein, the term "substituted alkyl," "substituted cycloalkyl," "substituted alkenyl," or "substituted alkynyl" refers to alkyl, cycloalkyl, alkenyl, or alkynyl, as defined elsewhere herein, substituted by one, two or three substituents independently selected from the group consisting of halogen, —OH, alkoxy, tetrahydro-2-H-pyranyl, $—NH_2$, $—NH(C_1\text{-}C_6alkyl)$, $—N(C_1\text{-}C_6\ alkyl)_2$, 1-methyl-imidazol-2-yl, pyridin-2-yl, pyridin-3-yl, pyridin-4-yl, —C(═O)OH, $—C(═O)O(C_1\text{-}C_6)alkyl$, trifluoromethyl, —C≡N, $—C(═O)NH_2$, $—C(═O)NH(C_1\text{-}C_6)alkyl$, $—C(═O)N((C_1\text{-}C_6)alkyl)_2$, $—SO_2NH_2$, $—SO_2NH(C_1\text{-}C_6alkyl)$, $—SO_2N(C_1\text{-}C_6\ alkyl)_2$, $—C(═NH)NH_2$, and $—NO_2$, in some embodiments containing one or two substituents independently selected from halogen, —OH, alkoxy, $—NH_2$, trifluoromethyl, $—N(CH_3)_2$, and —C(═O)OH, in some embodiments independently selected from halogen, alkoxy and —OH. Examples of substituted alkyls include, but are not limited to, 2,2-difluoropropyl, 2-carboxycyclopentyl and 3-chloropropyl.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In some embodiments, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

Ranges: throughout the instant specification, various aspects of the instant specification can be presented in a range format. It should be understood that the description in range format is merely for convenience and brevity and should not be construed as an inflexible limitation on the scope of the instant specification. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compound and Composition

As detailed elsewhere herein, in the instant study, several derivatives of colibactin were synthesized. In certain non-limiting embodiments, these colibactin derivatives possess similar chemical properties to those of colibactin, such as but not limited to being able to alkylate DNA molecules and/or forming interstrand cross-links (ICLs) in DNA. Unlike colibactin, which is known for the chemical instability, however, the colibactin derivatives in the instant study are stable. Such stable derivatives of colibactin can be useful tools to study colibactin, such as colibactin's ability to cause tumor and inflammation, without the need to isolate or handle an unstable molecule. Furthermore, the instant study further discovered that the colibactin derivatives are able to cause cell cycle arrest and cell death in a cancer cell line.

Therefore, in some embodiments, the instant specification is directed to a colibactin derivative, or a salt, solvate, isotopically labelled derivative, stereoisomer, tautomer, or geometric isomer thereof, or a mixture thereof.

In some embodiments, the colibactin derivative has a chemical structure of

A1-B-A2 Formula (I)

In some embodiments, the A1 portion and the A2 portion are independently the electrophilic warhead of colibactin or similar chemical groups.

In some embodiments, the B portion is a linker. In some embodiments, the B portion is a DNA intercalating motif capable of interacting with a DNA molecule.

In some embodiments, A1 is

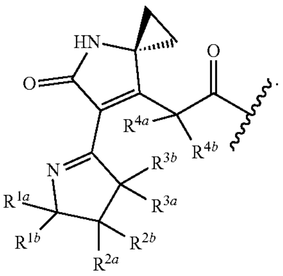

In some embodiments, A1 is

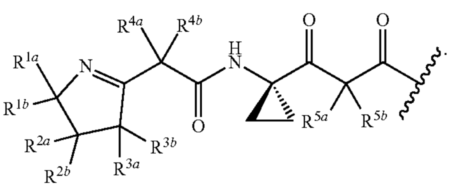

In some embodiments, A1 is
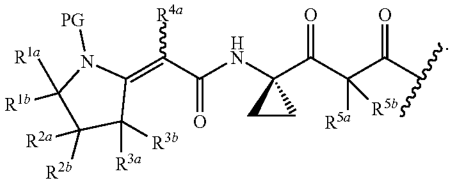
In some embodiments, A2 is
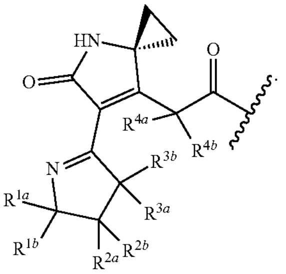
In some embodiments, A2 is
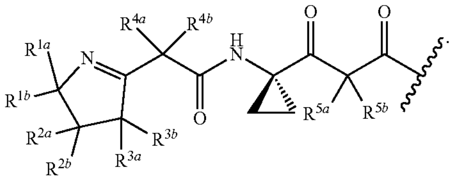
In some embodiments, A2 is
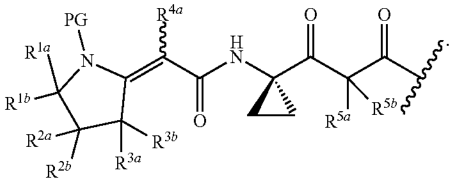
In some embodiments, B is a DNA intercalating motif. In some embodiments, B is
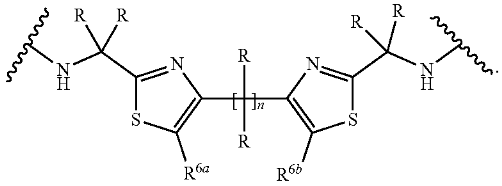
In some embodiments, B is
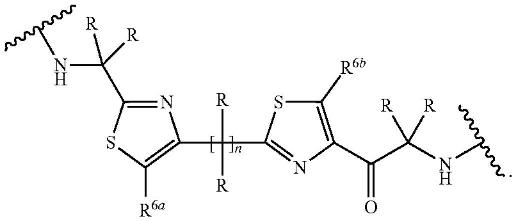
In some embodiments, B is
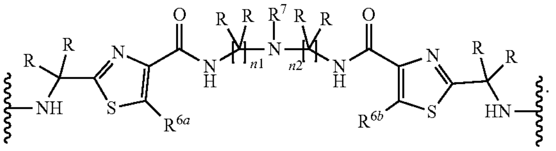
In some embodiments, B is
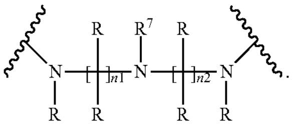
In some embodiments, B is
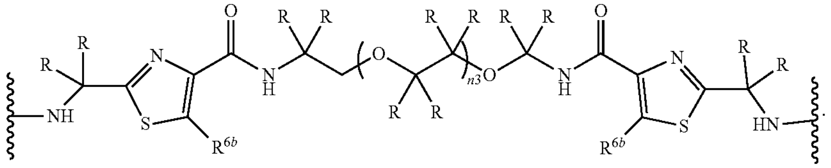

In some embodiments, each occurrence of $R^{1a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{1a}$ is hydrogen. In some embodiments, $R^{1a}$ is deuterium. In some embodiments, $R^{1a}$ is halogen. In some embodiments, $R^{1a}$ is optionally substituted $C_1$-$C_6$ alkoxy. In some embodiments, $R^{1a}$ is optionally substituted $C_1$-$C_6$ alkyl. In some embodiments, $R^{1a}$ is optionally substituted $C_3$-$C_6$ cycloalkyl.

In some embodiments, each occurrence of $R^{1b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{1b}$ is hydrogen. In some embodiments, $R^{1b}$ is deuterium. In some embodiments, $R^{1b}$ is halogen. In some embodiments, $R^{1b}$ is optionally substituted $C_1$-$C_6$ alkoxy. In some embodiments, $R^{1b}$ is optionally substituted $C_1$-$C_6$ alkyl. In some embodiments, $R^{1b}$ is optionally substituted $C_3$-$C_6$ cycloalkyl.

In some embodiments, each occurrence of $R^{2a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{2a}$ is hydrogen. In some embodiments, $R^{2a}$ is deuterium. In some embodiments, $R^{2a}$ is halogen. In some embodiments, $R^{2a}$ is optionally substituted $C_1$-$C_6$ alkoxy. In some embodiments, $R^{2a}$ is optionally substituted $C_1$-$C_6$ alkyl. In some embodiments, $R^{2a}$ is optionally substituted $C_3$-$C_6$ cycloalkyl.

In some embodiments, each occurrence of $R^{2b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{2b}$ is hydrogen. In some embodiments, $R^{2b}$ is deuterium. In some embodiments, $R^{2b}$ is halogen. In some embodiments, $R^{2b}$ is optionally substituted $C_1$-$C_6$ alkoxy. In some embodiments, $R^{2b}$ is optionally substituted $C_1$-$C_6$ alkyl. In some embodiments, $R^{2b}$ is optionally substituted $C_3$-$C_6$ cycloalkyl.

In some embodiments, each occurrence of $R^{3a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{3a}$ is hydrogen. In some embodiments, $R^{3a}$ is deuterium. In some embodiments, $R^{3a}$ is halogen. In some embodiments, $R^{3a}$ is optionally substituted $C_1$-$C_6$ alkoxy. In some embodiments, $R^{3a}$ is optionally substituted $C_1$-$C_6$ alkyl. In some embodiments, $R^{3a}$ is optionally substituted $C_3$-$C_6$ cycloalkyl.

In some embodiments, each occurrence of $R^{3b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{3b}$ is hydrogen. In some embodiments, $R^{3b}$ is deuterium. In some embodiments, $R^{3b}$ is halogen. In some embodiments, $R^{3b}$ is optionally substituted $C_1$-$C_6$ alkoxy. In some embodiments, $R^{3b}$ is optionally substituted $C_1$-$C_6$ alkyl. In some embodiments, $R^{3b}$ is optionally substituted $C_3$-$C_6$ cycloalkyl.

In some embodiments, each occurrence of $R^{4a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{4a}$ is hydrogen. In some embodiments, $R^{4a}$ is deuterium. In some embodiments, $R^{4a}$ is halogen. In some embodiments, $R^{4a}$ is optionally substituted $C_1$-$C_6$ alkoxy. In some embodiments, $R^{4a}$ is optionally substituted $C_1$-$C_6$ alkyl. In some embodiments, $R^{4a}$ is optionally substituted $C_3$-$C_6$ cycloalkyl.

In some embodiments, each occurrence of $R^{4b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{4b}$ is hydrogen. In some embodiments, $R^{4b}$ is deuterium. In some embodiments, $R^{4b}$ is halogen. In some embodiments, $R^{4b}$ is optionally substituted $C_1$-$C_6$ alkoxy. In some embodiments, $R^{4b}$ is optionally substituted $C_1$-$C_6$ alkyl. In some embodiments, $R^{4b}$ is optionally substituted $C_3$-$C_6$ cycloalkyl.

In some embodiments, each occurrence of $R^{5a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{5a}$ is hydrogen. In some embodiments, $R^{5a}$ is deuterium. In some embodiments, $R^{5a}$ is halogen. In some embodiments, $R^{5a}$ is optionally substituted $C_1$-$C_6$ alkoxy. In some embodiments, $R^{5a}$ is optionally substituted $C_1$-$C_6$ alkyl. In some embodiments, $R^{5a}$ is optionally substituted $C_3$-$C_6$ cycloalkyl.

In some embodiments, each occurrence of $R^{5b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{5b}$ is hydrogen. In some embodiments, $R^{5b}$ is deuterium. In some embodiments, $R^{5b}$ is halogen. In some embodiments, $R^{5b}$ is optionally substituted $C_1$-$C_6$ alkoxy. In some embodiments, $R^{5b}$ is optionally substituted $C_1$-$C_6$ alkyl. In some embodiments, $R^{5b}$ is optionally substituted $C_3$-$C_6$ cycloalkyl.

In some embodiments, each occurrence of $R^{6a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{6a}$ is hydrogen. In some embodiments, $R^{6a}$ is deuterium. In some embodiments, $R^{6a}$ is halogen. In some embodiments, $R^{6a}$ is optionally substituted $C_1$-$C_6$ alkoxy. In some embodiments, $R^{6a}$ is optionally substituted $C_1$-$C_6$ alkyl. In some embodiments, $R^{6a}$ is optionally substituted $C_3$-$C_6$ cycloalkyl.

In some embodiments, each occurrence of $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{6b}$ is hydrogen. In some embodiments, $R^{6b}$ is deuterium. In some embodiments, $R^{6b}$ is halogen. In some embodiments, $R^{6b}$ is optionally substituted $C_1$-$C_6$ alkoxy. In some embodiments, $R^{6b}$ is optionally substituted $C_1$-$C_6$ alkyl. In some embodiments, $R^{6b}$ is optionally substituted $C_3$-$C_6$ cycloalkyl.

In some embodiments, $R^7$ is selected from the group consisting of hydrogen, optionally substituted $C_1$-$C_6$ alkyl, optionally substituted $C_3$-$C_6$ cycloalkyl, optionally substituted $C_2$-$C_6$ cycloalkenyl. In some embodiments, $R^7$ is hydrogen. In some embodiments, $R^7$ is optionally substituted $C_1$-$C_6$ alkyl. In some embodiments, $R^7$ is optionally substituted $C_3$-$C_6$ cycloalkyl. In some embodiments, $R^7$ is optionally substituted $C_2$-$C_6$ cycloalkenyl.

In some embodiments, PG is a protective group. In some embodiments, PG is tert-butoxycarbonyl (Boc). In some embodiments, PG is trityl. In some embodiments, PG is dimethoxytrityl. In some embodiments, PG is tert-butyldimethylsilyl (TBDMS). In some embodiments, PG is carboxybenzyl (Cbz). In some embodiments, PG is nitroveratryloxycarbonyl (Nvoc). In some embodiments, PG is aryldithioethyloxycarbonyl (Ardec). In some embodiments, PG is (9H-fluoren-9-yl)methyl. In some embodiments, PG is ((S)-1-(((S)-1-((4-(hydroxymethyl)phenyl)amino)-1-oxo-5-ureidopentan-2-yl)amino)-3-methyl-1-oxobutan-2-yl) carbamate (Fmoc-Val-Cit-PAB). In some embodiments, PG is a derivate of any compound recited herein.

In some embodiments, each occurrence of R is independently H and optionally substituted $C_1$-$C_6$ alkyl. In some embodiments, R is H. In some embodiments, R is optionally substituted $C_1$-$C_6$ alkyl.

In some embodiments, each occurrence of n, n1, and n2 is independently an integer ranging from 2 to 6. In some embodiments, n is 2. In some embodiments, n is 3. In some embodiments, n is 4. In some embodiments, n is 5. In some embodiments, n is 6. In some embodiments, n1 is 2. In some embodiments, n1 is 3. In some embodiments, n1 is 4. In some embodiments, n1 is 5. In some embodiments, n1 is 6. In some embodiments, n2 is 2. In some embodiments, n2 is 3. In some embodiments, n2 is 4. In some embodiments, n2 is 5. In some embodiments, n2 is 6.

In some embodiments, each occurrence of n3 is independently an integer ranging from 1 to 6. In some embodiments, n3 is 1. In some embodiments, n3 is 2. In some embodiments, n3 is 3. In some embodiments, n3 is 4. In some embodiments, n3 is 5. In some embodiments, n3 is 6.

In some embodiments, A1 and A2 are each independently selected from the group consisting of

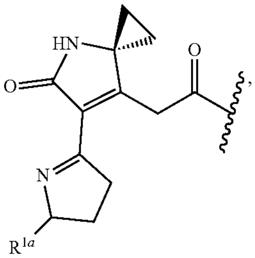

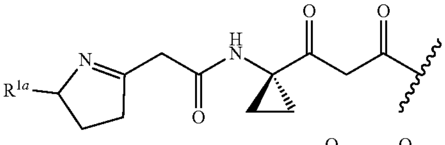

, and

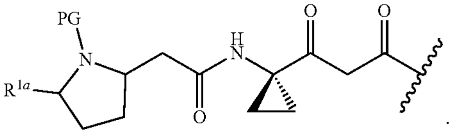

In some embodiments, A1 and A2 are each independently selected from the group consisting of

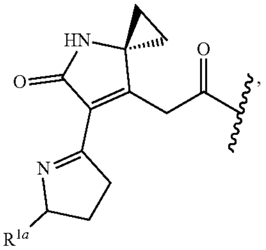

-continued

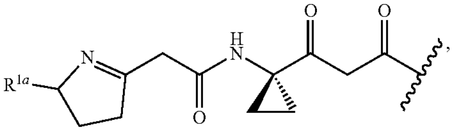

, and

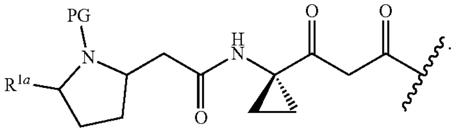

In some embodiments, A1 is

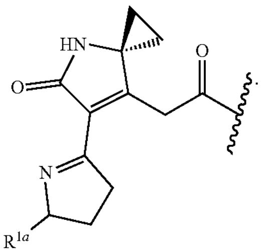

In some embodiments, A1 is

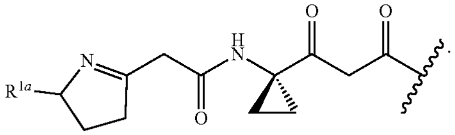

In some embodiments, A1 is

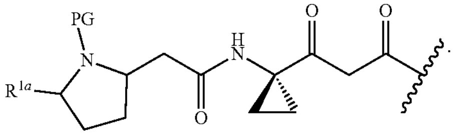

In some embodiments, A2 is

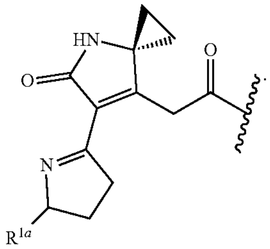

In some embodiments, A2 is

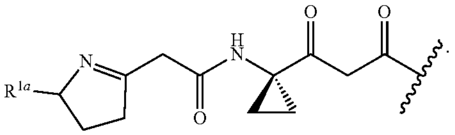

In some embodiments, A2 is

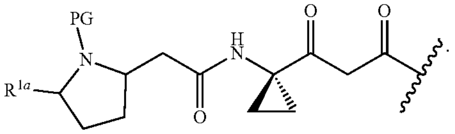

In some embodiments, A1 and A2 are each independently selected from the group consisting of

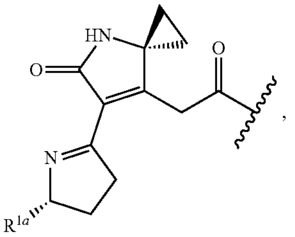

,

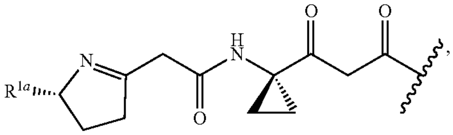

, and

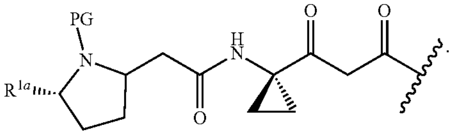

In some embodiments, A1 is

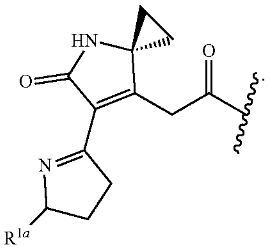

In some embodiments, A1 is

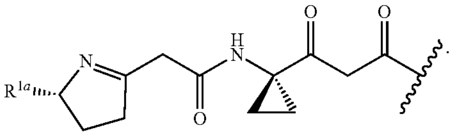

In some embodiments, A1 is

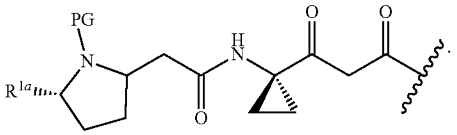

In some embodiments, A2 is

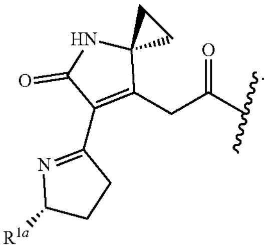

In some embodiments, A2 is

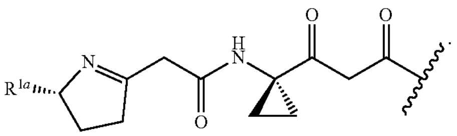

In some embodiments, A2 is

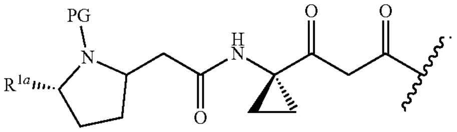

In some embodiments, A1 and A2 are each independently selected from the group consisting of

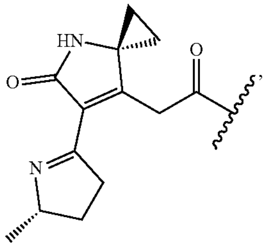

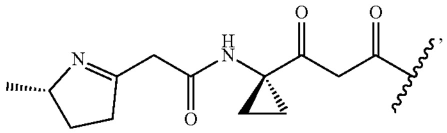

, and

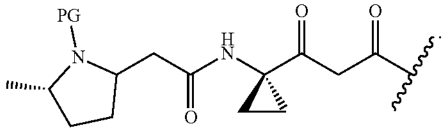

In some embodiments, A1 is
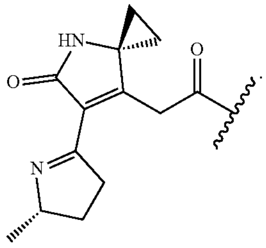
In some embodiments, A1 is
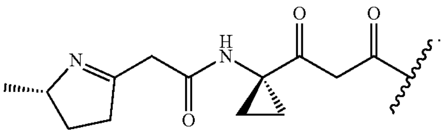
In some embodiments, A1 is
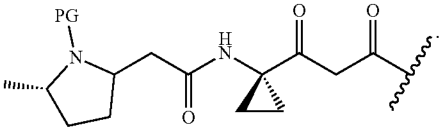
In some embodiments, A2 is
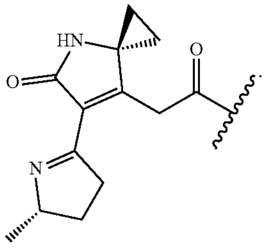
In some embodiments, A2 is
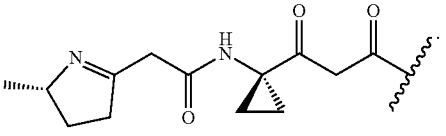
In some embodiments, A2 is
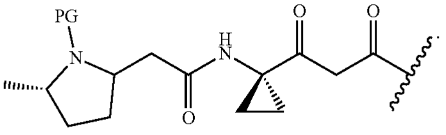
In some embodiments, the compound is:
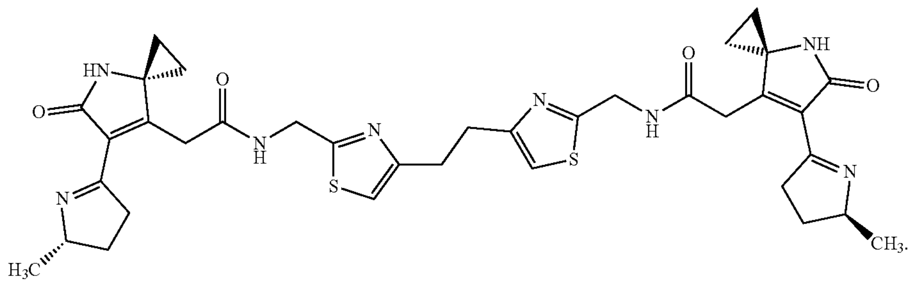
In some embodiments, the compound is:
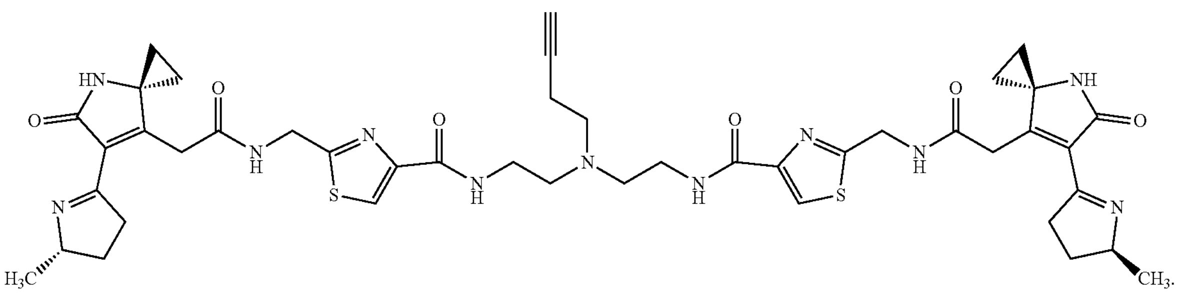

In some embodiments, the compound is:

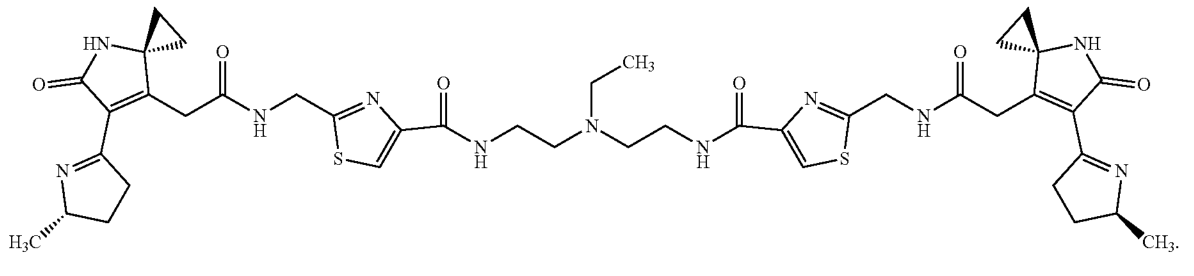

In some embodiments, the compound is:

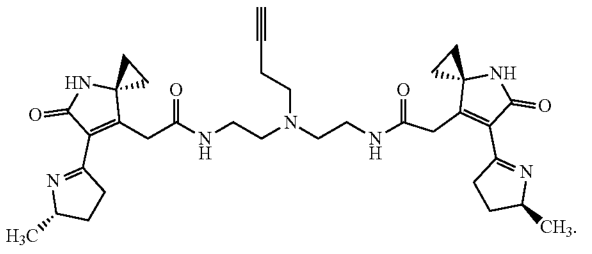

In some embodiments, the compound is:

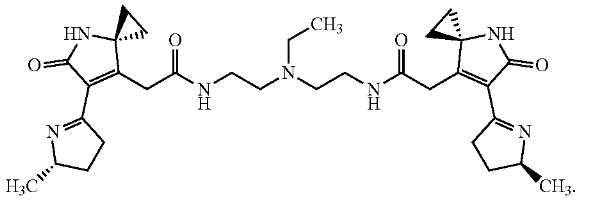

In some embodiments, the compound is a compound of Formula (II):

tuted $C_3$-$C_6$ cycloalkyl. In some embodiments, $R^{1a}$ is hydrogen. In some embodiments, $R^{1a}$ is deuterium. In some embodiments, $R^{1a}$ is halogen. In some embodiments, $R^{1a}$ is optionally substituted $C_1$-$C_6$ alkoxy. In some embodiments, $R^{1a}$ is optionally substituted $C_1$-$C_6$ alkyl. In some embodiments, $R^{1a}$ is optionally substituted $C_3$-$C_6$ cycloalkyl.

In some embodiments, each occurrence of $R^{1b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{1b}$ is hydrogen. In some embodiments, $R^{1b}$ is deuterium. In some embodiments, $R^{1b}$ is halogen. In some embodiments, $R^{1b}$ is optionally substituted $C_1$-$C_6$ alkoxy. In some embodiments, $R^{1b}$ is optionally substituted $C_1$-$C_6$ alkyl. In some embodiments, $R^{1b}$ is optionally substituted $C_3$-$C_6$ cycloalkyl.

In some embodiments, each occurrence of $R^{2a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{2a}$ is hydrogen. In some embodiments, $R^{2a}$ is deuterium. In some embodiments, $R^{2a}$ is halogen. In some embodiments, $R^{2a}$ is optionally substituted $C_1$-$C_6$ alkoxy. In some embodiments, $R^{2a}$ is optionally substituted $C_1$-$C_6$ alkyl. In some embodiments, $R^{2a}$ is optionally substituted $C_3$-$C_6$ cycloalkyl.

In some embodiments, each occurrence of $R^{2b}$ is independently selected from the group consisting of hydrogen, Formula (II)

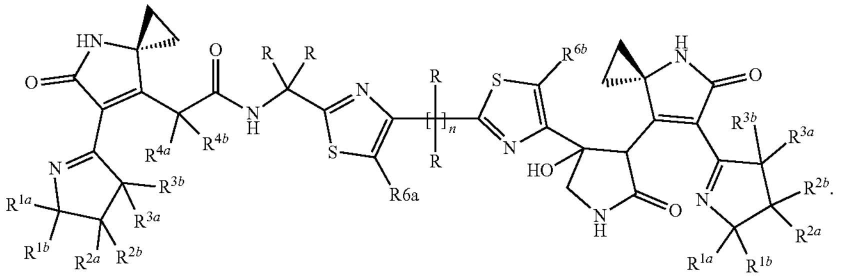

In some embodiments, each occurrence of $R^{1a}$, $R^{1b}$, $R^{2a}$, $R^{2b}$, $R^{3a}$, $R^{3b}$, $R^{4a}$, $R^{4b}$, $R^{6a}$, and $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl.

In some embodiments, each occurrence of $R^{1a}$ is independently selected from the group consisting of hydrogen, deuterium, halogen, optionally substituted $C_1$-$C_6$ alkoxy, optionally substituted $C_1$-$C_6$ alkyl, and optionally substideuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{2b}$ is hydrogen. In some embodiments, $R^{2b}$ is deuterium. In some embodiments, $R^{2b}$ is halogen. In some embodiments, $R^{2b}$ is optionally substituted $C_1$-$C_6$ alkoxy. In some embodiments, $R^{2b}$ is optionally substituted $C_1$-$C_6$ alkyl. In some embodiments, $R^{2b}$ is optionally substituted $C_3$-$C_6$ cycloalkyl.

In some embodiments, each occurrence of $R^{3a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{3a}$ is hydrogen. In some embodiments, $R^{3a}$ is deuterium. In some embodiments, $R^{3a}$ is halogen. In some embodiments, $R^{3a}$ is optionally substituted $C_1$-$C_6$ alkoxy. In some embodiments, $R^{3a}$ is optionally substituted $C_1$-$C_6$ alkyl. In some embodiments, $R^{3a}$ is optionally substituted $C_3$-$C_6$ cycloalkyl.

In some embodiments, each occurrence of $R^{3b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{3b}$ is hydrogen. In some embodiments, $R^{3b}$ is deuterium. In some embodiments, $R^{3b}$ is halogen. In some embodiments, $R^{3b}$ is optionally substituted $C_1$-$C_6$ alkoxy. In some embodiments, $R^{3b}$ is optionally substituted $C_1$-$C_6$ alkyl. In some embodiments, $R^{3b}$ is optionally substituted $C_3$-$C_6$ cycloalkyl.

In some embodiments, each occurrence of $R^{4a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{4a}$ is hydrogen. In some embodiments, $R^{4a}$ is deuterium. In some embodiments, $R^{4a}$ is halogen. In some embodiments, $R^{4a}$ is optionally substituted $C_1$-$C_6$ alkoxy. In some embodiments, $R^{4a}$ is optionally substituted $C_1$-$C_6$ alkyl. In some embodiments, $R^{4a}$ is optionally substituted $C_3$-$C_6$ cycloalkyl.

In some embodiments, each occurrence of Rb is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{4b}$ is hydrogen. In some embodiments, $R^{4b}$ is deuterium. In some embodiments, $R^{4b}$ is halogen. In some embodiments, $R^{4b}$ is optionally substituted $C_1$-$C_6$ alkoxy. In some embodiments, $R^{4b}$ is optionally substituted $C_1$-$C_6$ alkyl. In some embodiments, $R^{4b}$ is optionally substituted $C_3$-$C_6$ cycloalkyl.

In some embodiments, each occurrence of $R^{6a}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{6a}$ is hydrogen. In some embodiments, $R^{6a}$ is deuterium. In some embodiments, $R^{6a}$ is halogen. In some embodiments, $R^{6a}$ is optionally substituted $C_1$-$C_6$ alkoxy. In some embodiments, $R^{6a}$ is optionally substituted $C_1$-$C_6$ alkyl. In some embodiments, $R^{6a}$ is optionally substituted $C_3$-$C_6$ cycloalkyl.

In some embodiments, each occurrence of $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl. In some embodiments, $R^{6b}$ is hydrogen. In some embodiments, $R^{6b}$ is deuterium. In some embodiments, $R^{6b}$ is halogen. In some embodiments, $R^{6b}$ is optionally substituted $C_1$-$C_6$ alkoxy. In some embodiments, $R^{6b}$ is optionally substituted $C_1$-$C_6$ alkyl. In some embodiments, $R^{6b}$ is optionally substituted $C_3$-$C_6$ cycloalkyl.

In some embodiments, each occurrence of R is independently H and optionally substituted $C_1$-$C_6$ alkyl. In some embodiments, R is H. In some embodiments, R is optionally substituted $C_1$-$C_6$ alkyl In some embodiments, n is independently an integer ranging from 2 to 6. In some embodiments, n is 2. In some embodiments, n is 3. In some embodiments, n is 4. In some embodiments, n is 5. In some embodiments, n is 6.

In some embodiments, the compound is

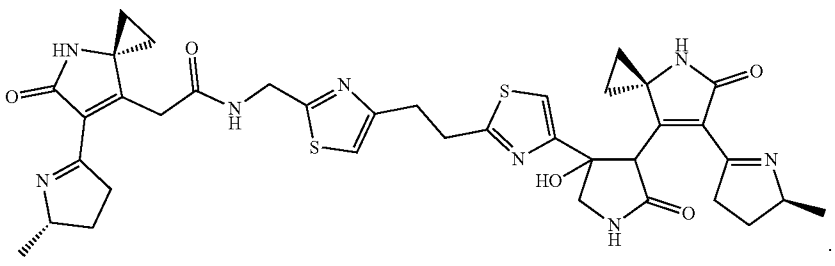

In some embodiments, the compound is capable of alkylating a DNA molecule. In some embodiments, the compound is capable of forming an interstrand cross-link in a DNA molecule.

In some embodiments, the compound is capable of causing a cell cycle arrest in a cell. In some embodiments, the compound is capable of causing a cell death in a cell. In some embodiments, the cell is a cancer cell.

In some embodiments, the compound is a compound for preventing, treating, and/or ameliorating a cancer in a subject in need thereof. In some embodiments, the cancer is a cervical cancer.

The compounds of the instant specification may possess one or more stereocenters, and each stereocenter may exist independently in either the (R) or (S) configuration. In some embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including, by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or any mixtures thereof, or in the case where two or more chiral centers are present, all diastereomers or any mixtures thereof.

In some embodiments, the compounds of the instant specification exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In some embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In some embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed disclosure. The compounds of the instant specification may contain any of the substituents, or combinations of substituents, provided herein.

Salts

The compounds described herein may form salts with acids or bases, and such salts are included in the instant specification. The term "salts" embraces addition salts of free acids or bases that are useful within the methods of the instant specification. The term "pharmaceutically acceptable salt" refers to salts that possess toxicity profiles within a range that affords utility in pharmaceutical applications. In some embodiments, the salts are pharmaceutically acceptable salts. Pharmaceutically unacceptable salts may nonetheless possess properties such as high crystallinity, which have utility in the practice of the instant specification, such as for example utility in process of synthesis, purification or formulation of compounds useful within the methods of the instant specification.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the instant specification.

Suitable pharmaceutically acceptable base addition salts of compounds of the instant specification include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Synthesis

In some embodiments, the compound of the instant specification can be prepared by a synthesis method the same as or similar to those as described in the "Example 1: Synthesis and Characterization of Colibactin Derivatives" section.

The instant specification further provides methods of preparing the compound of the instant specification. Compounds of the instant specification can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatography such as high-performance liquid chromatography (HPLC), gas chromatography (GC), gel-permeation chromatography (GPC), or thin layer chromatography (TLC).

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In some embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In some embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In some embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

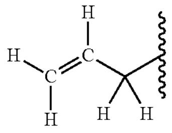
allyl

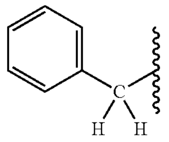
Br

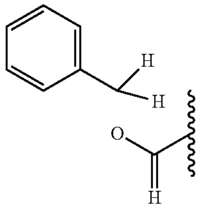
Obz

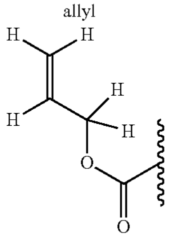
Alloc

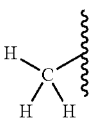
Mo

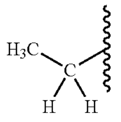
Et

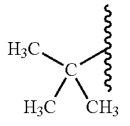
t-butyl

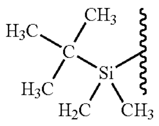
TBCMS

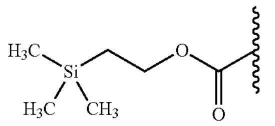
Tooc

-continued

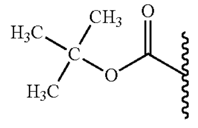
Boc

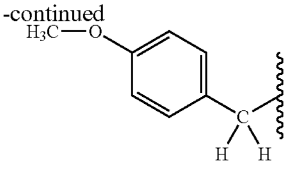
PMB

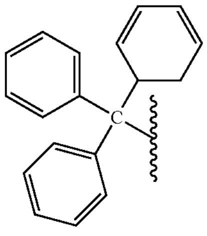
trityl

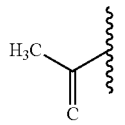
acetyl

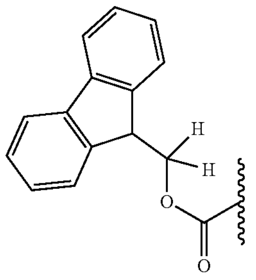
FMOC

Other protecting groups, plus a detailed description of techniques applicable to the creation of protecting groups and their removal are described in Greene & Wuts, Protective Groups in Organic Synthesis, $3^{rd}$ Ed., John Wiley & Sons, New York, NY, 1999, and Kocienski, Protective Groups, Thieme Verlag, New York, NY, 1994, which are incorporated herein by reference for such disclosure.

In some embodiments, a compound of the instant specification can be prepared, for example, according to the illustrative synthetic methods outlined herein.

In some embodiments, the instant specification is directed to a pharmaceutical composition including the salt, solvate, isotopically labelled derivative, stereoisomer, tautomer, or geometric isomer thereof, or any mixture thereof. The pharmaceutical composition as well as the formulation thereof is detailed below in the "Pharmaceutical Compositions and Formulations" section.

Method of Alkylating DNA Molecule and Forming DNA Interstrand Cross-Link (ICL)

As detailed elsewhere herein, the colibactin derivatives synthesized in the instant study are able to alkylate DNA molecules, and to form DNA interstrand-cross links (ICLs). ICLs are lesions that pose a significant threat to eukaryotic cells during cell division, especially to cells undergoing rapid division such as the cells found in cancers. Indeed, the chemotherapy medication cisplatin is known to kill fast proliferating cancer cells by alkylating the DNA molecules and forming interstrand-cross links.

Therefore, in some embodiments, the instant specification is directed to a method of alkylating a DNA molecule. In some embodiments, the method includes contacting the DNA molecule with a colibactin derivative, or a salt, solvate, isotopically labelled derivative, stereoisomer, tautomer, or geometric isomer thereof, or a mixture thereof.

In some embodiments, the colibactin derivative is the same as or similar to the compounds detailed above in the "Compound and Composition" section.

In some embodiments, alkylating the DNA molecule includes forming a DNA interstrand cross-link (ICL) in the DNA molecule.

In some embodiments, the method includes contacting the DNA molecule with the compound contemplated in the invention at a pH ranging from 5.0 to 7.0. In some embodiments, the pH is equal to or greater than about 5.0, 5.2, 5.4, 5.6, 5.8, 6.0, 6.2, 6.4, 6.6, 6.8, or 7.0. In some embodiments, the pH is equal to or less than about 5.0, 5.2, 5.4, 5.6, 5.8, 6.0, 6.2, 6.4, 6.6, 6.8, or 7.0.

In some embodiments, the DNA molecule is a genomic DNA of a cell and in a nucleus of the cell. In some embodiments, the cell is a cancer cell.

Method of Preventing, Treating, and/or Ameliorating Cancer

As detailed elsewhere herein, the colibactin derivatives synthesized in the instant study are able to alkylate DNA molecules, and to form DNA interstrand-cross links. Alkylation of the DNA molecules formation of interstrand-cross links are believe to be the mechanism by which the chemotherapy medication cisplatin kill cancer cells. Indeed, the instant study shows that the colibactin derivatives are able to cause cell cycle arrest and cell death in a human cervical cancer cell line, the HeLa cell line.

Therefore, in some embodiments, the instant specification is directed to a method of preventing, treating, and/or ameliorating cancer in a subject in need thereof. In some embodiments, the method includes administering to the subject an effective amount of a colibactin derivative, or a salt, solvate, isotopically labelled derivative, stereoisomer, tautomer, or geometric isomer thereof, or a mixture thereof.

In some embodiments, the colibactin derivative is a compound the same as or similar to the compound as described in the "Compound and Composition" section above.

In some embodiments, the compounds disclosed herein are useful to prevent, treat, and/or ameliorate any cancer that is susceptible to DNA-modifying and/or DNA-damaging agents in chemotherapy, such as but not limited to cancers that are susceptible to temozolomide, anthracyclines, and/or platin derivatives. In some embodiments, the cancer is cervical cancer. In some embodiments, the cancer is breast cancer. In some embodiments, the cancer is urinary tract cancer. In some embodiments, the cancer is gastrointestinal cancers.

In some embodiments, the colibactin derivative, or the salt, solvate, isotopically labelled derivative, stereoisomer, tautomer, or geometric isomer thereof, or any mixture thereof is administered in the form of a pharmaceutical composition. Pharmaceutical compositions as well as formulations thereof are described in detail in the "Pharmaceutical Compositions and Formulations" section below.

Methods of administrating the colibactin derivative, or the salt, solvate, isotopically labelled derivative, stereoisomer, tautomer, or geometric isomer thereof, or any mixture thereof, or the pharmaceutical composition thereof are described in detail in the "Administration/Dosing" section and the "Administration" section.

Pharmaceutical Compositions and Formulations

The instant specification provides pharmaceutical compositions comprising at least one compound of the instant specification or a salt or solvate thereof, which are useful to practice methods of the instant specification. Such a pharmaceutical composition may consist of at least one compound of the instant specification or a salt or solvate thereof, in a form suitable for administration to a subject, or the pharmaceutical composition may comprise at least one compound of the instant specification or a salt or solvate thereof, and one or more pharmaceutically acceptable carriers, one or more additional ingredients, or any combinations of these. At least one compound of the instant specification may be present in the pharmaceutical composition in the form of a physiologically acceptable salt, such as in combination with a physiologically acceptable cation or anion, as is well known in the art.

In some embodiments, the pharmaceutical compositions useful for practicing the method of the instant specification may be administered to deliver a dose of between 1 ng/kg/day and 100 mg/kg/day. In other embodiments, the pharmaceutical compositions useful for practicing the instant specification may be administered to deliver a dose of between 1 ng/kg/day and 1,000 mg/kg/day.

The relative amounts of the active ingredient, the pharmaceutically acceptable carrier, and any additional ingredients in a pharmaceutical composition of the instant specification will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the instant specification may be suitably developed for nasal, inhalational, oral, rectal, vaginal, pleural, peritoneal, parenteral, topical, transdermal, pulmonary, intranasal, buccal, ophthalmic, epidural, intrathecal, intravenous, or another route of administration. A composition useful within the methods of the instant specification may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In some embodiments, the compositions of the instant specification are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the instant specification is contemplated include, but are not limited to, humans and other primates, mammals including commercially relevant mammals such as cattle, pigs, horses, sheep, cats, and dogs.

In some embodiments, the compositions of the instant specification are formulated using one or more pharmaceutically acceptable excipients or carriers. In some embodiments, the pharmaceutical compositions of the instant specification comprise a therapeutically effective amount of at least one compound of the instant specification and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring, and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the instant specification may comprise a preservative from about 0.005% to 2.0% by total weight of the composition. The preservative is used to prevent spoilage in the case of exposure to contaminants in the environment. Examples of preservatives useful in accordance with the instant specification include but are not limited to those selected from the group consisting of benzyl alcohol, sorbic acid, parabens, imidurea and any combinations thereof. One such preservative is a combination of about 0.5% to 2.0% benzyl alcohol and 0.05-0.5% sorbic acid.

The composition may include an antioxidant and a chelating agent that inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non-ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the instant specification may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the instant specification may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the instant specification may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the instant specification to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the instant specification is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of the instant specification may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the instant specification employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the instant specification are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In some embodiments, the compositions of the instant specification are administered to the patient in dosages that range from one to five times per day or more. In other embodiments, the compositions of the instant specification are administered to the patient in range of dosages that include, but are not limited to, once every day, every two days, every three days to once a week, and once every two weeks. It will be readily apparent to one skilled in the art that the frequency of administration of the various combination compositions of the instant specification will vary from subject to subject depending on many factors including, but not limited to, age, disease or disorder to be treated, gender, overall health, and other factors. Thus, the instant specification should not be construed to be limited to any particular dosage regime and the precise dosage and composition to be administered to any patient will be determined by the attending physician taking all other factors about the patient into account.

Compounds of the instant specification for administration may be in the range of from about 1 μg to about 7,500 mg, about 20 μg to about 7,000 mg, about 40 μg to about 6,500 mg, about 80 μg to about 6,000 mg, about 100 μg to about 5,500 mg, about 200 μg to about 5,000 mg, about 400 μg to about 4,000 mg, about 800 μg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the instant specification is from about 0.5 μg and about 5,000 mg. In some embodiments, a dose of a compound of the instant specification used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In some embodiments, the instant specification is directed to a packaged pharmaceutical composition comprising a container holding a therapeutically effective amount of a compound of the instant specification, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in some embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the instant specification include inhalational, oral, nasal, rectal, parenteral, sublingual, transdermal, transmucosal (e.g., sublingual, lingual, (trans) buccal, (trans) urethral, vaginal (e.g., trans- and perivaginally), (intra) nasal, and (trans) rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the instant specification are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the instant specification may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, PA (e.g., OPADRY® OY Type, OYC Type, Organic Enteric OY-P Type, Aqueous Enteric OY-A Type, OY-PM Type and OPADRY® White, 32K18400). It is understood that similar type of film coating or polymeric products from other companies may be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the instant specification may contain liposomes. The composition of the liposomes and their use are known in the art (i.e., U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. For example, it should be present in an amount from about 0.0005% to about 5% of the composition; for example, it should be present in an amount of from about 0.001% to about 1% of the composition. Such compounds may be synthetically- or naturally derived.

Buccal Administration

A pharmaceutical composition of the instant specification may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the instant specification includes additional modifications of these and other formulations not described herein, but which are known to those of skill in the art.

Rectal Administration

A pharmaceutical composition of the instant specification may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of the instant specification include dosage forms as described in U.S. Pat. Nos. 6,340,475, 6,488,962, 6,451,808, 5,972,389, 5,582,837, and 5,007,790. Additional dosage forms of the instant specification also include dosage forms as described in U.S. patent applications Nos. 20030147952, 20030104062, 20030104053, 20030044466, 20030039688, and 20020051820. Additional dosage forms of the instant specification also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In some embodiments, the compositions and/or formulations of the instant specification may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the instant specification may be administered in the form of microparticles, for example, by injection or in the form of wafers or discs by implantation.

In some embodiments of the instant specification, the compounds useful within the instant specification are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of the instant specification and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the instant specification. Accordingly, all values and ranges encompassed by these values and ranges are meant to be encompassed within the scope of the instant specification. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

EXAMPLES

The instant specification further describes in detail by reference to the following experimental examples. These examples are provided for purposes of illustration only, and are not intended to be limiting unless so specified. Thus, the instant specification should in no way be construed as being limited to the following examples, but rather, should be construed to encompass any and all variations which become evident as a result of the teaching provided herein.

Example 1: Synthesis and Characterization of Colibactin Derivatives

One of the most defining characteristics of colibactin is its instability, and despite extensive effort colibactin has not yet been isolated from the producing bacteria. The highly electrophilic warhead containing a spirocyclic cyclopropane readily degrades under isolation and purification conditions and has only been accessed via chemical synthesis. Additionally, the central region of colibactin contains two thiazole rings linked by an α-aminoketone (see colibactin 771 (1a), FIG. 1A), as determined by biosynthetic analysis and the isolation of truncated metabolites. This substructure readily undergoes aerobic oxidation to an α-ketoimine, as in colibactin 769 (2a), which in turn hydrolyzes to the 1,2-diketone colibactin 770 (3a). Each structure 1a-3a is nominally capable of DNA alkylation, but given the varying partial pressure of dioxygen in the gut, the composition of this central residue at the time of cross-linking remains an unresolved question. Only dinucleotide adducts containing the α-diketone 3a have been detected in bacterial extracts, likely because these studies have occurred in the presence of atmospheric oxygen.

Figure 1B:
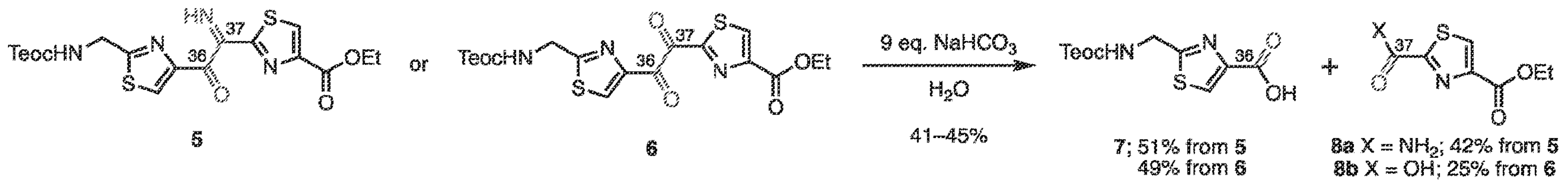

Additionally, studies of the synthetic α-ketoimine 5 and the 1,2-diketone 6 revealed a novel decomposition pathway that further complicates efforts to isolate and study colibactin (FIG. 1B). Thus, the central carbon-carbon (connecting C36 and C37, colibactin numbering) undergoes cleavage upon exposure to water or methanol under slightly basic conditions (e.g., tetrahydrofuran-aqueous sodium bicarbonate, 23° C., FIG. 1B). The α-ketoimine 2a and the 1,2-diketone 3a in colibactin decompose by parallel pathways and previous studies of synthetic 3 demonstrated that the 1,2-diketone undergoes rapid carbon-carbon bond oxidation and cleavage at neutral pH. Without wishing to be limited by any theory, it is likely that the electrophilic warheads and/or the C36-C37 decomposition pathway defines colibactin's physiological half-life.

These facile modes of degradation have prevented the isolation of colibactin and its direct biological study. As such, colibactin has been generated in situ by $clb^+$ bacteria co-incubated with either exogenous DNA or eukaryotic cells. This coculture approach has been successful in elucidating the genotoxic phenotype of $clb^+$ bacteria, but it does not allow colibactin to be studied directly, or independently from the producing organism and other virulence factors that may be associated with these effects.

Anticipating that the instability of colibactin 770 (3a) might preclude its study in cellular assays, the instant study sought to identify a stable colibactin analog that would facilitate these otherwise inaccessible studies. Specifically, the instant study sought to determine if the C36-C37 1,2-diketone residue was essential to colibactin's mode of action, as removal of this residue might lead to a more stable derivative. To test this, the 1,2-diketone residue was replaced with a saturated, unsubstituted two-carbon linker, as in 4a (FIG. 1A). Without wishing to be limited by any theory, it was envisioned that this alteration would not change the spacing between the two electrophilic warheads and maintain the flexibility required to bind within the DNA minor groove. Therefore, removal of these substituents would reveal if this highly unstable C36-C37 functional group is needed in forming DNA cross-links, through hydrogen bonding, electrostatic interactions, or even covalent interactions with DNA. Additionally, study of 4a would allow the determination if the oxidative decomposition of the C36-C37 bond was a phenomenon essential to colibactin's DNA-damaging capabilities. While the cyclopropane residues in colibactin are established DNA electrophiles, other potential sites of alkylation have been proposed. Accordingly, a derivative of 4a bearing methyl substituents in place of the cyclopropane was prepared, and left- and right-hand fragments possessing the electrophilic pharmacophore were synthesized, to determine if both cyclopropanes of colibactin were involved in ICL formation.

Herein synthetic and biological mechanism of action studies that support this strategy as a viable approach to study colibactin's genotoxicity is described. It was found that the target 4a can be synthesized by a biomimetic sequence involving cyclization of its linear precursor 9, but that the unexpected ring isomer 4b (FIG. 2) is the major product formed. This cyclization is apparently irreversible and was previously undetected using MS-based characterization of 3a. The synthesis and study of 4a and 4b and related control compounds has established the first method to study colibactin's genotoxicity independent of the producing bacteria. Furthermore, it is shown that the unstable C36-C37 diketone is not required for DNA ICL formation and confirm the cyclopropane residues as the site of covalent cross-linking, thus further refining colibactin's structure and mode of DNA binding.

Figure 2:
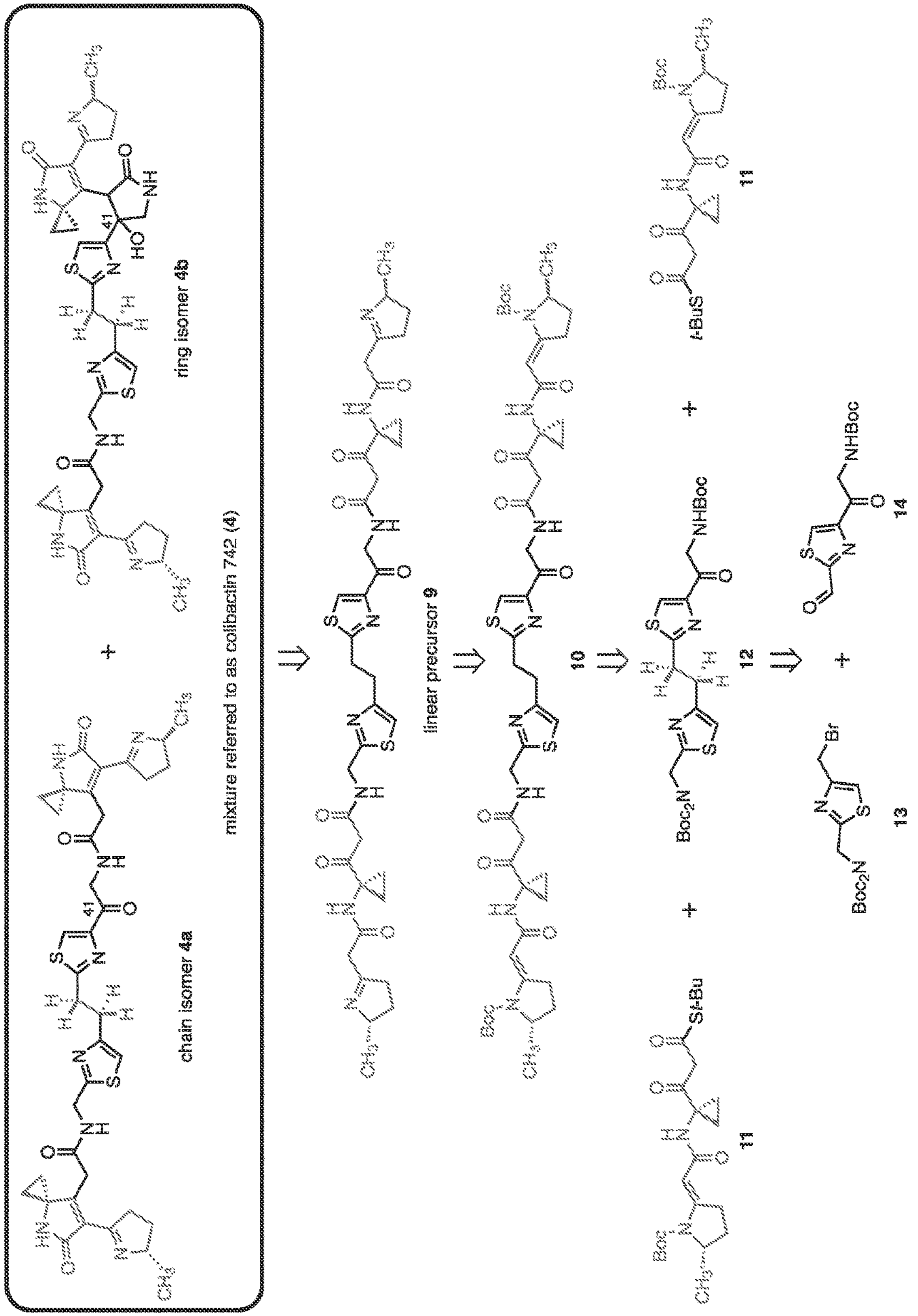
FIG. 2 depicts the retrosynthetic analysis of colibactin 742 (4) according to some embodiments.

It was envisioned that 4a/4b, hereafter referred to collectively as colibactin 742 (4), could be prepared by the convergent approach outlined in FIG. 2. The electrophilic spirocyclopropyldihydro-2-pyrrolones that constitutes the colibactin warheads were envisioned to be accessible from the linear precursor 9. Inspired by the biosynthetic prodrug strategy utilized by the bacteria, the instant study targeted the vinylogous imide 10, which was expected to be stable toward purification and handling. The colibactin pharmacophore is prone to cyclopropane-opening and this has prevented its purification and isolation, making these deprotection-cyclization cascades a necessary approach. Prior synthetic work (Xue, M. et al., Science 2019, 365) indicated that the vinylogous imide 10 would facilitate late-stage incorporation of the most reactive portions of the molecule through a three-component silver-mediated fragment coupling employing the vinylogous imide fragment 11 (2.2 equivs) and the bis (thiazole) core 12. The bis (thiazole) core 12 itself was disconnected via a Wittig homologation between the phosphonium salt derived from the bromothiazole 13 and the aldehyde 14.

Figures 3A, 3B:
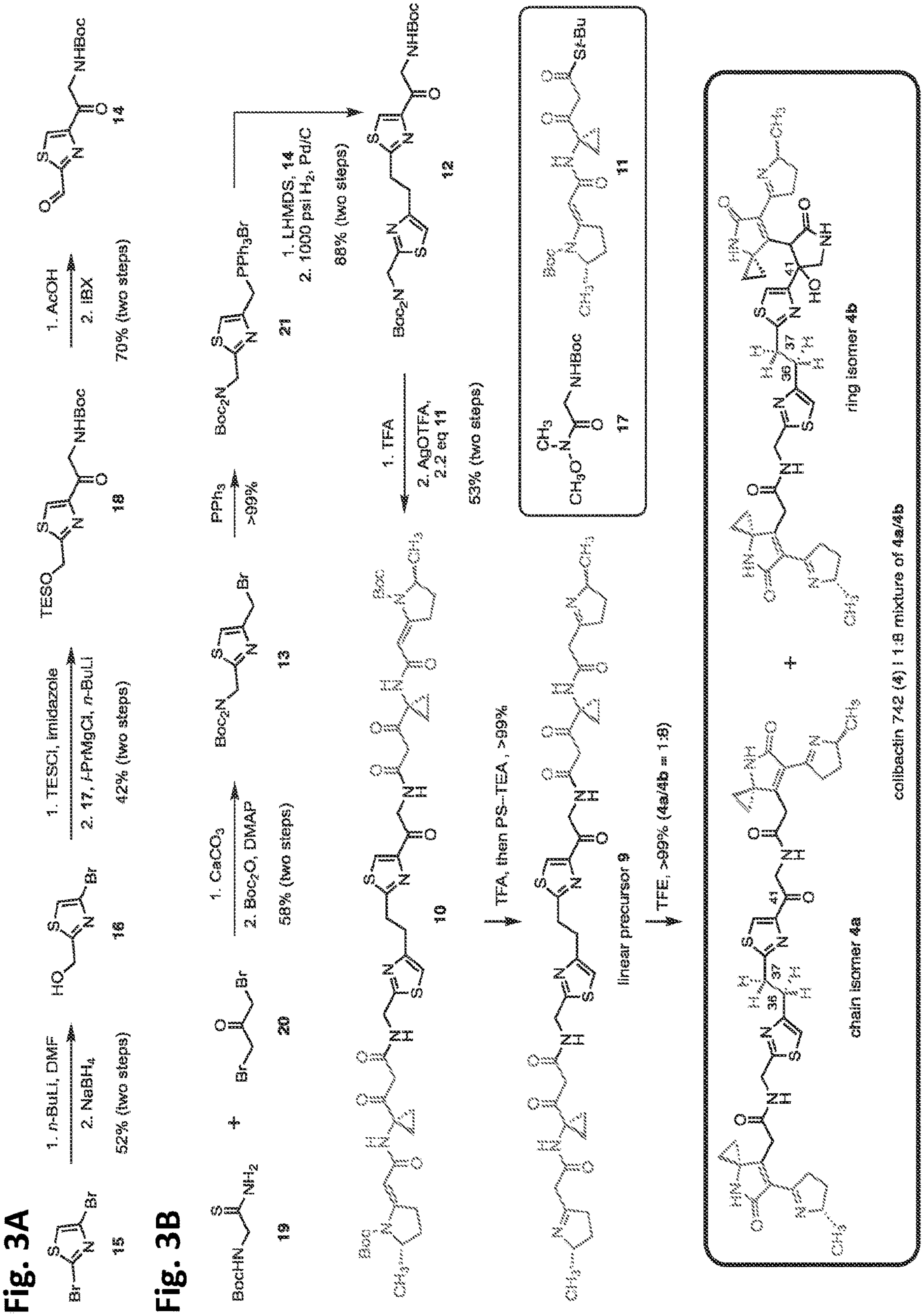
FIGS. 3A-3B depict the synthesis of colibactin 742 (mixture of chain and ring isomers 4a and 4b) according to some embodiments.

The synthesis began with the preparation of the aldehyde 14 (FIG. 3A). Starting with 2,4-dibromothiazole (15), a Bouveault aldehyde synthesis, followed by sodium borohydride reduction, provided the alcohol 16 (52%). The hydroxy group was protected as a silyl ether (triethylsilyl chloride (TESCl), imidazole). Lithium-halogen exchange (n-butyllithium) followed by addition of the magnesiated Weinreb amide 17 provided the ketone 18 (42%, two steps). Prior deprotonation of the Weinreb amide 17 with iso-propyl magnesium chloride was essential to prevent protonation of the organolithium intermediate. Selective removal of the triethylsilyl ether in the presence of the tert-butyl carbamate was achieved by treatment with acetic acid. Oxidation (2-iodoxybenzoic acid, IBX) generated the aldehyde 14 (70%, two steps; overall: 6 steps, 23%).

The synthesis of the thiazole 13 began with a Hantzsch thiazole condensation between the protected thioamide 19 and 1,3-dibromoacetone (20, FIG. 3B). Treatment of the product with di-tert-butyldicarbonate generated the imide 13 (58%, two steps). The phosphonium salt 21 was prepared in quantitative yield by heating of the bromide 13 with triphenylphosphine. Fragment coupling via Wittig homologation provided the expected alkene as an uncharacterized 1:1 mixture of isomers. The mixture of alkene isomers was reduced (dihydrogen, palladium on carbon, 1000 psi) to generate the bis (thiazole) 12 (88%, two steps). Unmasking of the primary amines (trifluoroacetic acid) followed by a two-fold amidation with the thioester 11 (Xue, M. et al., Science 2019, 365), furnished the vinylogous imide 10 (53%, two steps). Finally, removal of the tert-butyl carbamate protecting groups (trifluoroacetic acid) formed a linear bis (iminium) ion that was neutralized with polymer-supported triethylamine (PS-TEA) to provide the imine 9 (>99%).

Cyclodehydration of 9 occurred rapidly (5-10 min at 22° C.) in protic solvents such as methanol, water, and 2,2,2-trifluoroethanol (TFE) and more slowly (~24 h at 22° C.) in non-polar solvents such as dichloromethane. On preparative scales the instant study found it most convenient to conduct the cyclization in TFE. Thus, quantitative cyclization was achieved by stirring a solution of 9 in TFE (20 mM) at 22° C. for 10 min, followed by concentration in vacuo. While the cyclopropane warheads formed as expected, it was surprising that the ring isomer 4b, which arises from the addition of C44 to the C41 ketone, was the major product (4b:4a~8:1).

Figure 5:
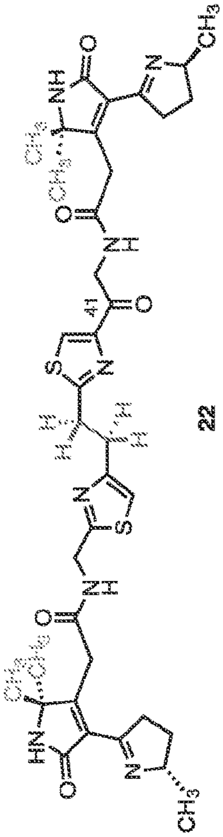
FIG. 5 depicts the control compounds prepared to evaluate structure-activity relationships according to some embodiments.
Figure 5:
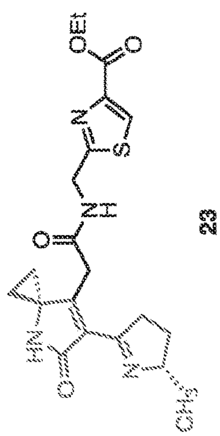
Figure 5:
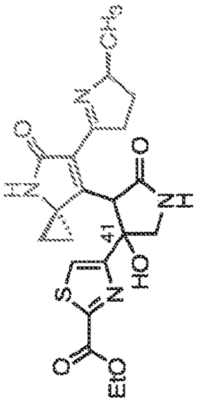

The timing of this addition relative to warhead formation is currently unknown (see Example 4 and FIG. 5 for details). The ring isomer 4b was generated as a 1:1.2 mixture of C41 diastereomers ($^1$H NMR analysis). The expected chain isomer 4a was a minor component of the mixture. Interestingly, one of the cyclopropane CH resonances in 4b appears at −0.43 ppm, a shift clearly caused by to the anisotropic effect of the proximal thiazole ring.

The formation of the ring isomer 4b raises the possibility that a parallel cyclization occurs in structures 1a-3a (discussed elsewhere herein). This additional ring closure may not have been detected in the MS-based approaches previously employed to characterize colibactin. Indeed, in subsequent attempts to procure homogenous samples of 3a, the corresponding ring isomers were detected by $^1$H NMR analysis.

Figure 4:
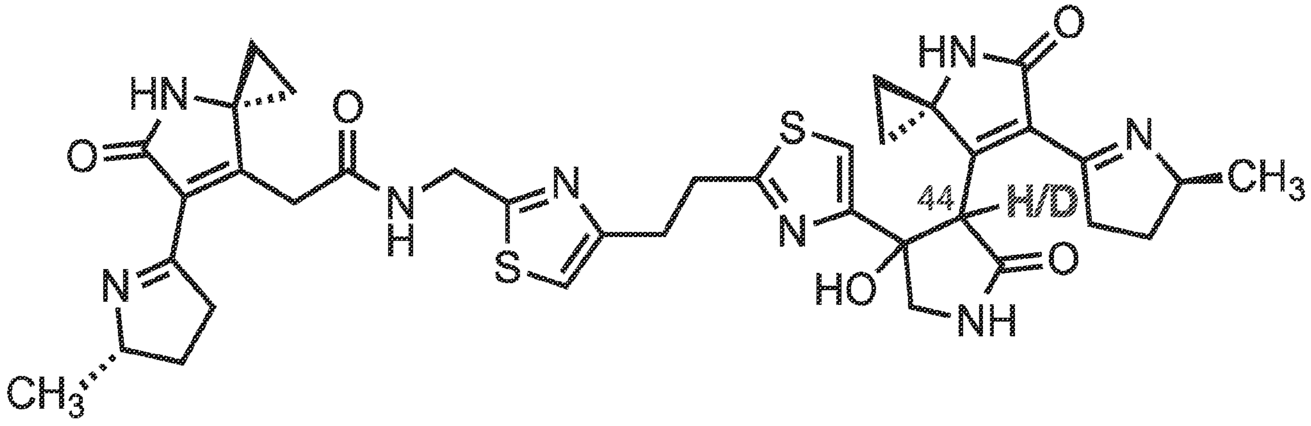
FIG. 4 depicts the attempted H-D exchange at C44 in 4b according to some embodiments.

The mixture of ring-chain isomers—colibactin 742 (4)—could not be separated due to the instability of the colibactin pharmacophore toward HPLC purification. To determine if the isomers were interconverting, the mixture were incubated in methanol-$d_4$ or with $KD_2PO_4$ in 1:1 methanol-$d_4$/$D_2O$, and monitored for deuterium incorporation at C44 in 4b (FIG. 4). No deuterium incorporation was observed in either experiment after heating for 75 min at 37° C. (1H NMR analysis), suggesting addition to the C41 carbonyl is irreversible under these conditions. The generation of the ring isomer 4b as the predominant species has important implications for the mode of DNA binding of colibactin, which has previously been modeled only as occurring through the chain structure 3a (Dziubańska-Kusibab, P. J. et al., Nat. Med. 2020, 26, 1063).

Example 2: Colibactin Derivatives Alkylate DNA Molecules and Form DNA Interstrand Cross-Links (ICLs)

While the abundance of evidence suggests colibactin induces DNA cross-links via cyclopropane ring-opening, other sites of DNA alkylation (such as 1,2-addition into the cyclic imine) have been proposed (see FIG. 1A) (Vizcaino, M. I. et al., Nat. Chem. 2015, 7, 411). To clarify this point, the control compounds shown in FIG. 5 were synthesized. The gem-dimethyl derivative 22 was prepared with the expectation that cross-linking should not be observed if cyclopropane addition constituted the most significant site of DNA alkylation. The left-hand and right-hand fragments 23 and 24, respectively, were prepared to further probe the involvement of each cyclopropane and the cyclic imine residues in DNA alkylation. These studies were designed to explore if multiple clb metabolites together induce clb genotoxicity (as previously proposed in, e.g., Li, Z. et al., Nat. Chem. 2019, 11, 880) or if the complete clb metabolite (colibactin) is solely responsible. It was anticipated that if cyclopropane-opening were the most significant site of alkylation, these compounds would alkylate but not cross-link DNA. However, careful biological interrogation of clb genotoxic and mutagenic capabilities have shown that the dominate phenotype induced in eukaryotic cells by clb is the product of DNA cross-links (Bossuet-Greif, N. et al., MBio 2018, 9). As such, investigating the DNA interactions of the left- and right-hand fragments 23 and 24, respectively, would provide insights into the polypharmacological capabilities of the clb gene cluster.

Figure 6A:
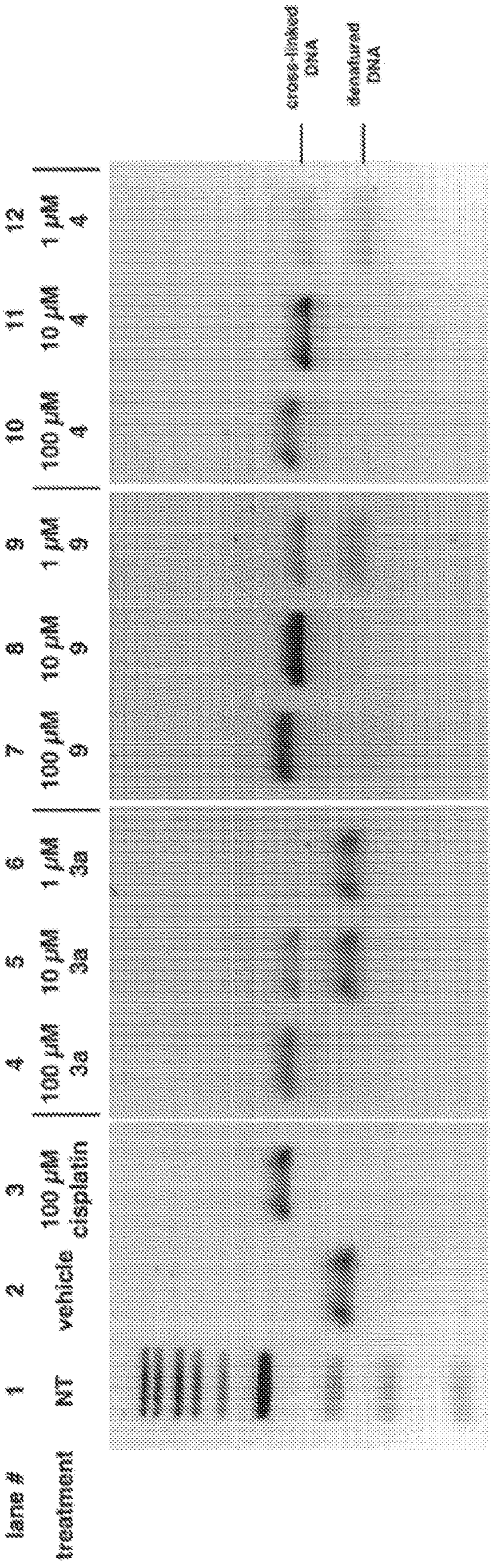
FIGS. 6A-6C depict the DNA crosslinking ability of several compounds according to some embodiments. The DNA cross-linking assays employ linear pUC19 DNA. DMSO was used as vehicle (negative control), and 100 μM cisplatin was used as positive controls. The DNA was analyzed by 0.4% NaOH denaturing and agarose gel electrophoresis (90 V, 1.5 h).
Figure 9:
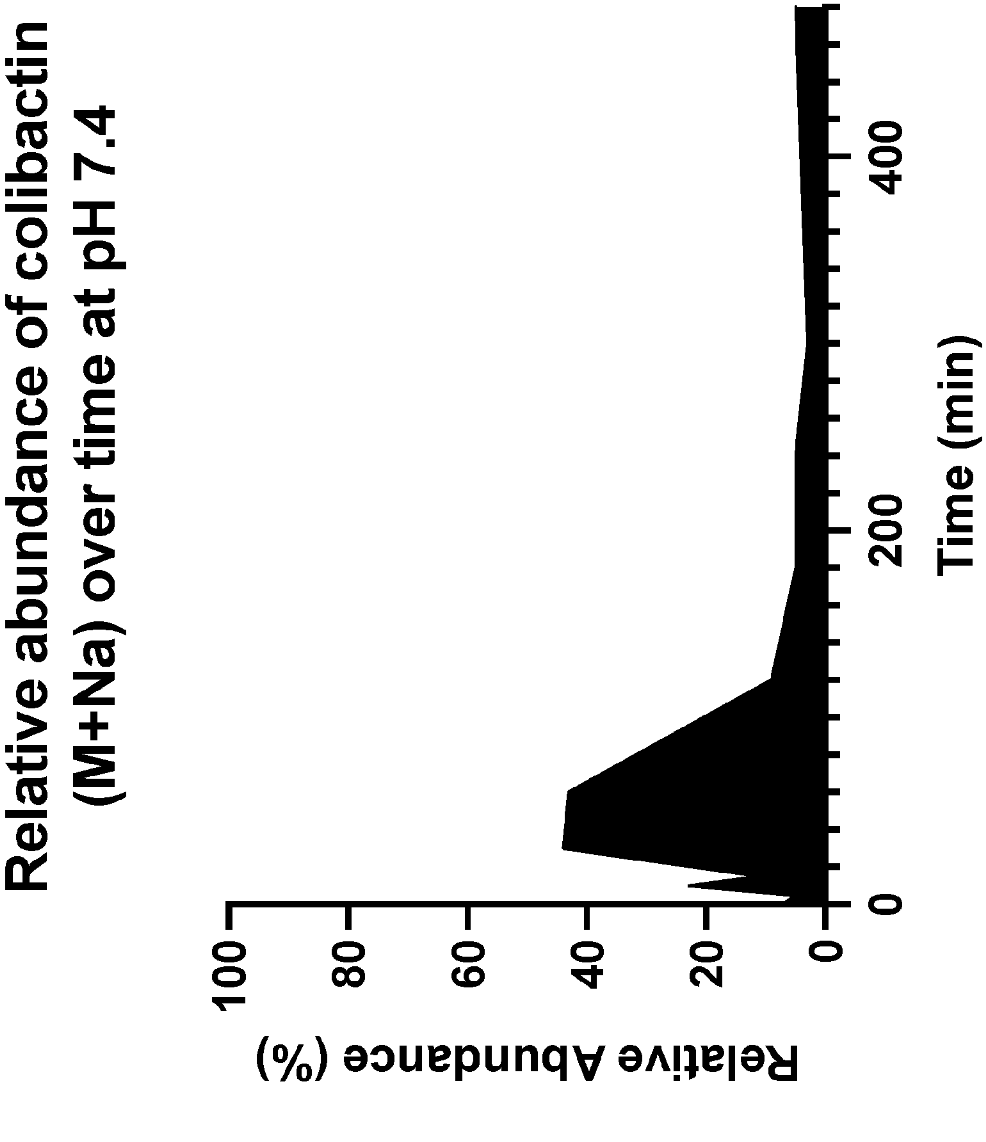
FIG. 9 depicts the percentage of colibactin 770 (M+Na) over time at pH 7.4, 37° C. according to some embodiments. Specifically, the linear precursor to colibactin 770 (nominally 404 nmol), prepared according to Xu et al. (Science 2019, 365) was dissolved in DMSO (100 μL) and the resulting solution was diluted with PBS buffer (400 μL) at 22° C. This solution was immediately warmed to 37° C. in a preheated water bath. Aliquots (15 μL) were taken at 0 min, 5 min, 10 min, 15 min, 30 min, 60 min, 120 min, 180 min, 240 min, 300 min, and 480 min. Each aliquot was dissolved in acetonitrile (150 μL) and then immediately frozen in liquid nitrogen. The frozen aliquots were stored at −78° C. until the time course was complete. Aliquots were quickly thawed and analyzed using a Shimadzu Scientific Instruments QToF 9030 LC-MS system, equipped with a Nexera LC-40D xs UHPLC, consisting of a CBM-40 Lite system controller, a DGU-405 Degasser Unit, two LC-40D XS UHPLC pumps, a SIL-40C XS autosampler and a Column Oven CTO-40S. UV data was collected with a Shimadzu Nexera HPLC/UHPLC Photodiode Array Detector SPD M-40 in the range of 190-800 nm. Mass spectra were recorded with the quadrupole time-of-flight (QToF) 9030 mass spectrometer. The samples were held at 4° C. in the autosampler compartment. 300 nL of each sample was injected into a sample loop and separated on a Shim-pack Scepter C18-120 (1.9 μm, 2.1×100 mm column, equilibrated at 40° C.). The ionization source was run in ESI mode, with the electrospray needle held at +4.5 kV. Solvent A: water containing 0.1% formic acid. Solvent B: acetonitrile containing 0.1% formic acid. Flow was held constant at 300 μL/min and the composition of the eluent was changed according to the following gradient: 0 to 0.5 min, held at 95% A, 5% B; 0.5 to 3 min, linear gradient to 5% A, 95% B; 3 to 4 min, hold at 5% A, 95% B. Measurements and data post-processing were performed with LabSolutions 5.97 Realtime Analysis and PostRun to obtain the area under the curve for each extracted mass. The areas were summed to obtain the total area and this value was used to calculate the relative abundance of each species as a percentage of the total area using Microsoft Excel. The percentage of colibactin 770 (M+Na) was plotted over time to obtain the trace above.
Figure 10:
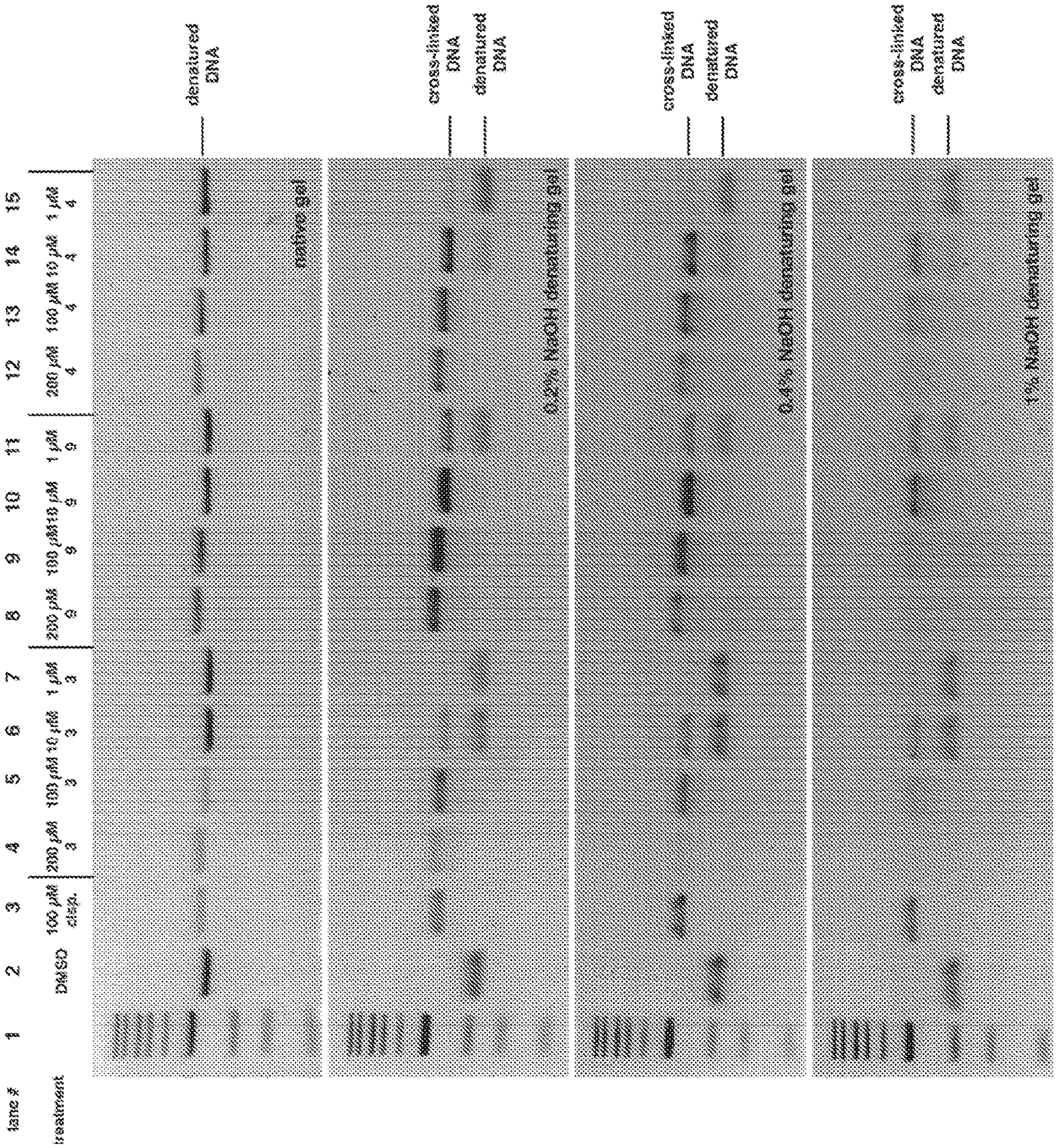
FIG. 10 depicts the DNA cross-linking assay employing linear pUC19 DNA and synthetic colibactin (3), 9, and colibactin 742 (4) according to some embodiments. Specifically, 5% DMSO was used as vehicle (negative control), and 100 μM cisplatin was used as positive control. DNA ladder (Lane #1); 5% DMSO (Lane #2); 100 μM cisplatin (Lane #3); 200 μM colibactin (3) (Lane #4); 100 μM colibactin (3) (Lane #5); 10 μM colibactin (3) (Lane #6); 1 μM colibactin (3) (Lane #7); 200 μM 9 (Lane #8); 100 μM 9 (Lane #9); 10 μM 9 (Lane #10); 1 μM 9 (Lane #11); 200 μM colibactin 742 (4) (Lane #12); 100 μM colibactin 742 (4) (Lane #13); 10 μM colibactin 742 (4) (Lane #14); 1 μM colibactin 742 (4) (Lane #15). Conditions (Lane #3): linearized pUC19 DNA (15.4 μM in base pairs), 5% DMSO (vehicle), 100 μM cisplatin, 10 mM citric buffer, pH 5.0, 4 h, 37° C. Conditions (Lanes #4-#7): linearized pUC19 DNA (15.4 μM in base pairs), colibactin (3) (200 μM-1 μM), 5% DMSO, 10 mM citric buffer, pH 5.0, 4 h, 37° C. Conditions (Lanes #8-#11): linearized pUC19 DNA (15.4 μM in base pairs), 9 (200 μM-1 μM), 5% DMSO, 10 mM citric buffer, pH 5.0, 4 h, 37° C. Conditions (Lanes #12-#15): linearized pUC19 DNA (15.4 μM in base pairs), colibactin 742 (4) (200 μM-1 μM), 5% DMSO, 10 mM citric buffer, pH 5.0, 4 h, 37° C. The DNA was analyzed by native, 0.2% NaOH, 0.4% NaOH, and 1% NaOH denaturing agarose gel electrophoresis (90 V, 1.5 h). Linear=linearized DNA in native form, linear-denat.=linearized DNA in denaturing form, linear-XL=linerized DNA cross-linked by colibactins or cisplatin.

The instant study evaluated the ability of colibactin 742 (4), the linear precursor 9, the gem-dimethyl derivative 22, and the left- and right-hand fragments 23 and 24 to cross-link DNA, and compared the stability of those cross-links to those derived from 3a. The linear precursor 9 was included as it was established that linear precursors are off-loaded from the biosynthetic assembly line and that cyclization to the final biosynthetic product occurs spontaneously, though the timing of this cyclization (before or after eukaryotic cell entry) is not known. It was established that slightly acidic conditions (pH 5.0) were necessary to stabilize ICLs derived from 3a (3a readily decomposes at pH 7.4, FIG. 9). The instant study observed that both the linear precursor 9 and colibactin 742 (4) induced stable DNA ICLs at pH 5.0 and at a concentration ten-fold lower than 3a (FIG. 6A). The increased level of ICLs derived from colibactin 742 (4) and 9 relative to 3a is most reasonably attributed to the enhanced stability of the thiazole spacer, which is not capable of bond cleavage and the resulting separation of the DNA strands. Additionally, the stability of the ICLs derived from colibactin 742 (4) and 9 at pH 5.0 were comparable to those derived from 3a under increasingly stringent denaturing conditions, suggesting a similar mode of DNA binding and alkylation (FIG. 10). Furthermore, the increased level of ICLs with 9 and 4a relative to colibactin 770 (3a) suggests that the C36-C37 1,2-diketone is not essential in facilitating DNA binding.

Figure 6B:
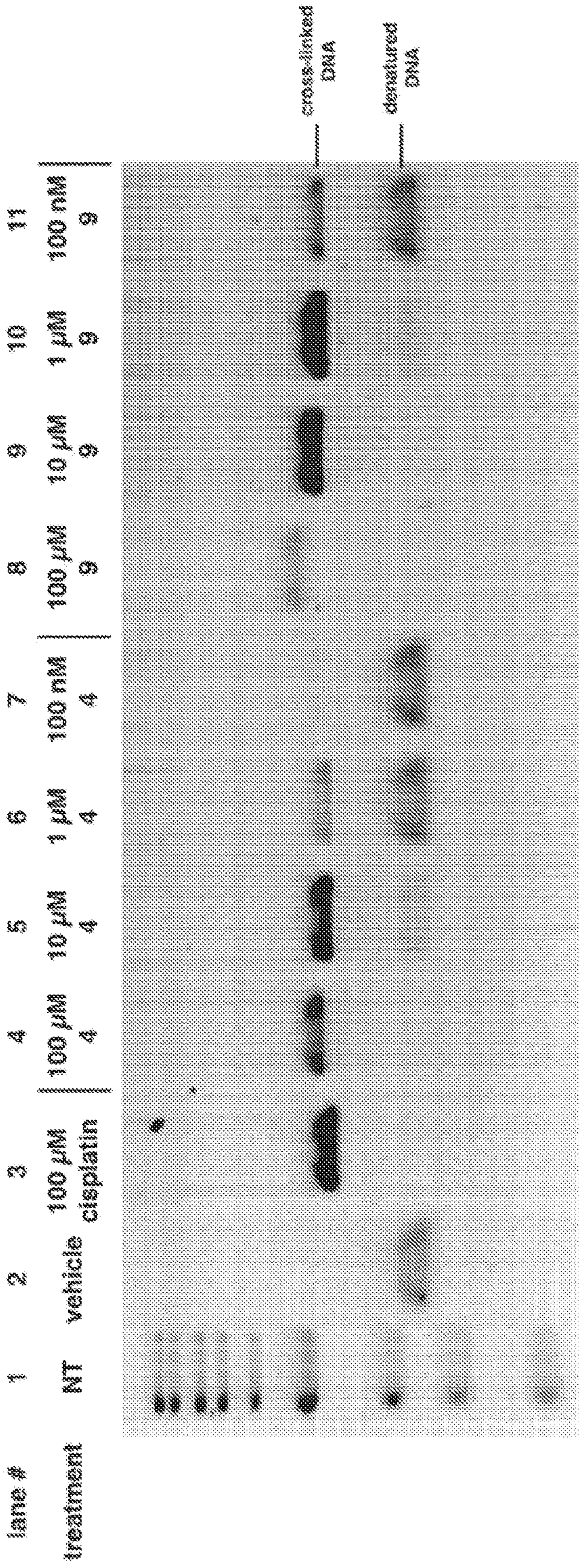
Figure 6C:
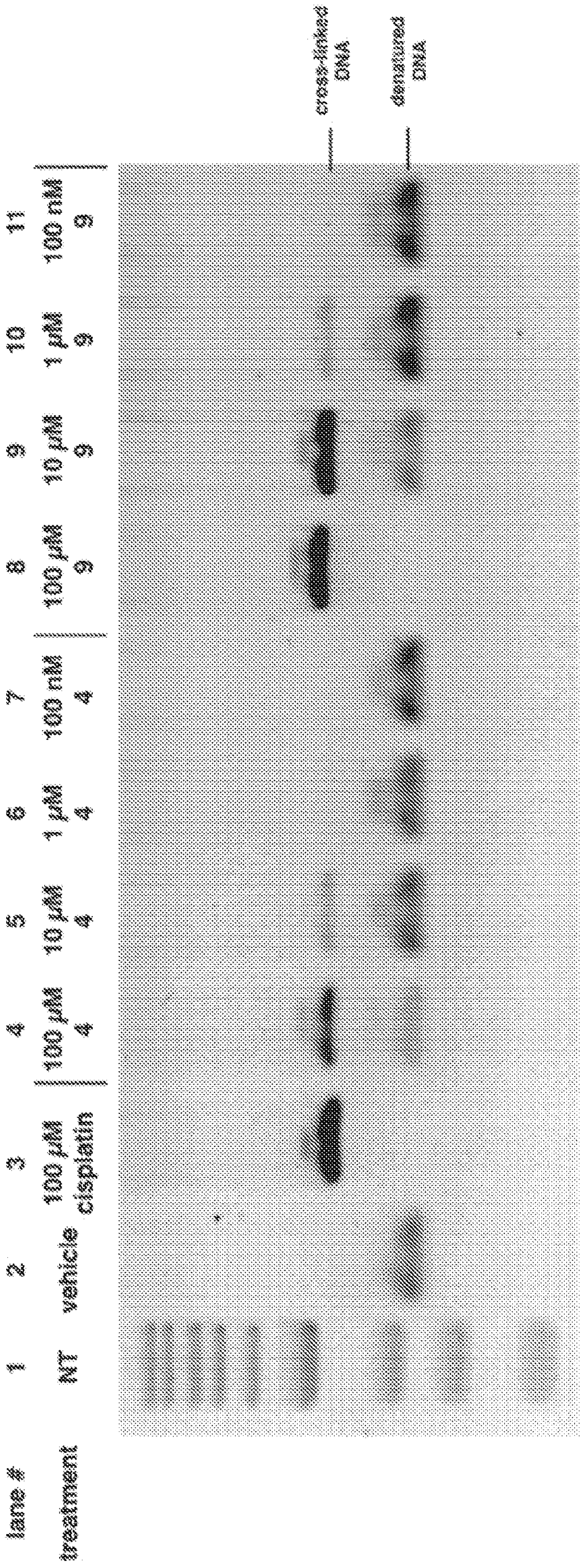
Figure 11:
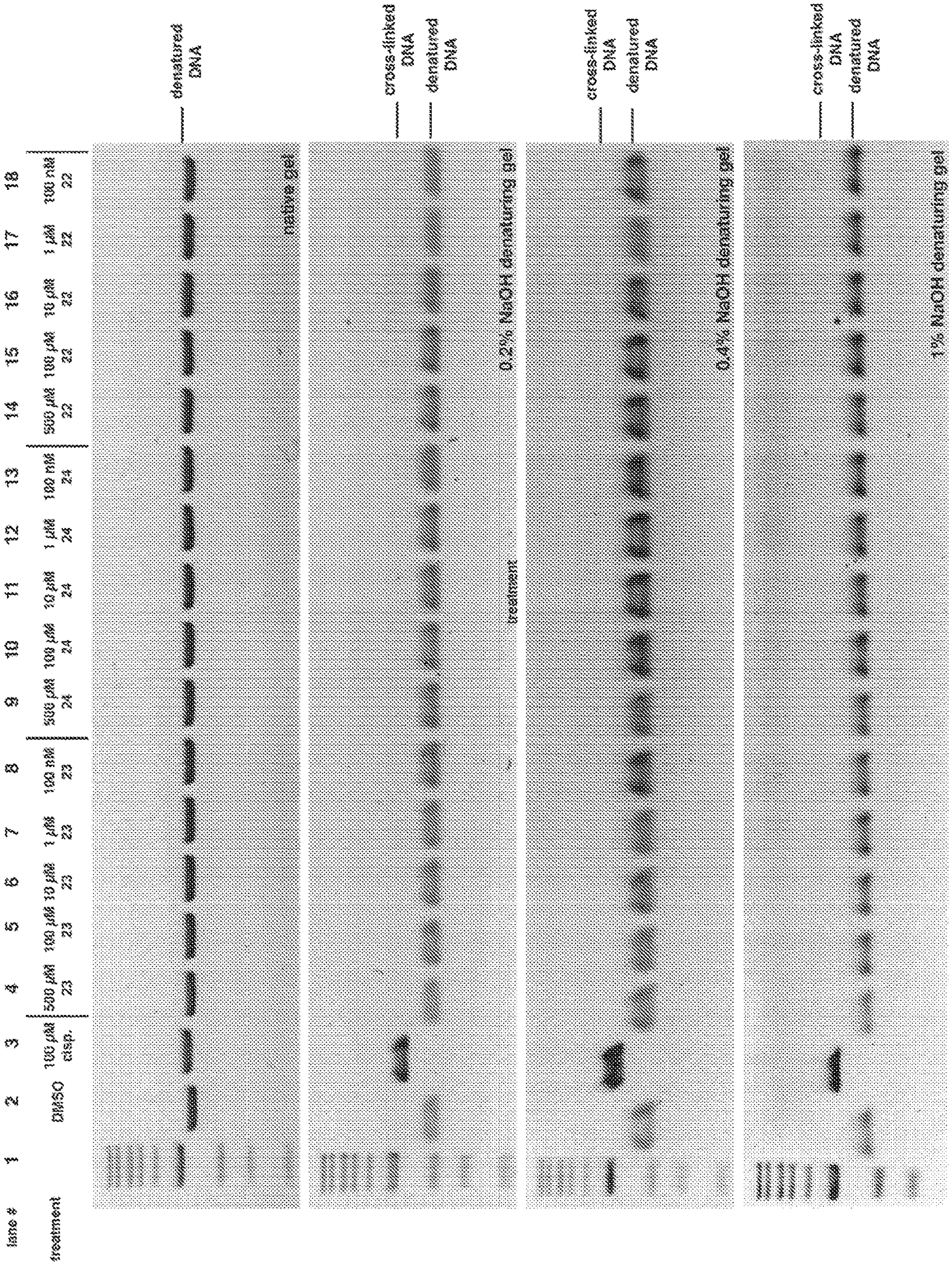
FIG. 11 depicts the DNA cross-linking assay employing linear pUC19 DNA and synthetic colibactin fragments 23, 24, and 22. Specifically, 5% DMSO was used as vehicle (negative control), and 100 μM cisplatin was used as positive control. DNA ladder (Lane #1); 5% DMSO (Lane #2); 100 μM cisplatin (Lane #3); 500 μM 23 (Lane #4); 100 μM 23 (Lane #5); 10 μM 23 (Lane #6); 1 μM 23 (Lane #7); 100 nm 23 (Lane #8); 500 μM 24 (Lane #9); 100 μM 24 (Lane #10); 10 μM 24 (Lane #11); 1 μM 24 (Lane #12); 100 nm 24 (Lane #13); 500 μM 22 (Lane #14); 100 μM 22 (Lane #15); 10 μM 22 (Lane #16); 1 μM 22 (Lane #17); 100 nm 22 (Lane #18). Conditions (Lane #2): linearized pUC19 DNA (15.4 μM in base pairs), 5% DMSO (vehicle), 10 mM citric buffer, pH 5.0, 4 h, 37° C. Conditions (Lane #3): linearized pUC19 DNA (15.4 μM in base pairs), 5% DMSO (vehicle), 100 μM cisplatin, 10 mM citric buffer, pH 5.0, 4 h, 37° C. Conditions (Lanes #4-#8): linearized pUC19 DNA (15.4 μM in base pairs), 23 (500 μM-100 nM), 5% DMSO, 10 mM citric buffer, pH 5.0, 4 h, 37° C. Conditions (Lanes #9-#13): linearized pUC19 DNA (15.4 μM in base pairs), 24 (500 μM-1 μM), 5% DMSO, 10 mM citric buffer, pH 5.0, 4 h, 37° C. Conditions (Lanes #14-#18): linearized pUC19 DNA (15.4 μM in base pairs), 22 (500 μM-100 nM), 5% DMSO, 10 mM citric buffer, pH 5.0, 4 h, 37° C. The DNA was analyzed by native, 0.2% NaOH, 0.4% NaOH, and 1% NaOH denaturing agarose gel electrophoresis (90 V, 1.5 h). Linear=linearized DNA in native form, linear-denat.=linearized DNA in denaturing form, linear-XL=DSB/linerized DNA cross-linked by colibactins or cisplatin.
Figures 12A, 12B, 12C, 12D, 12E:
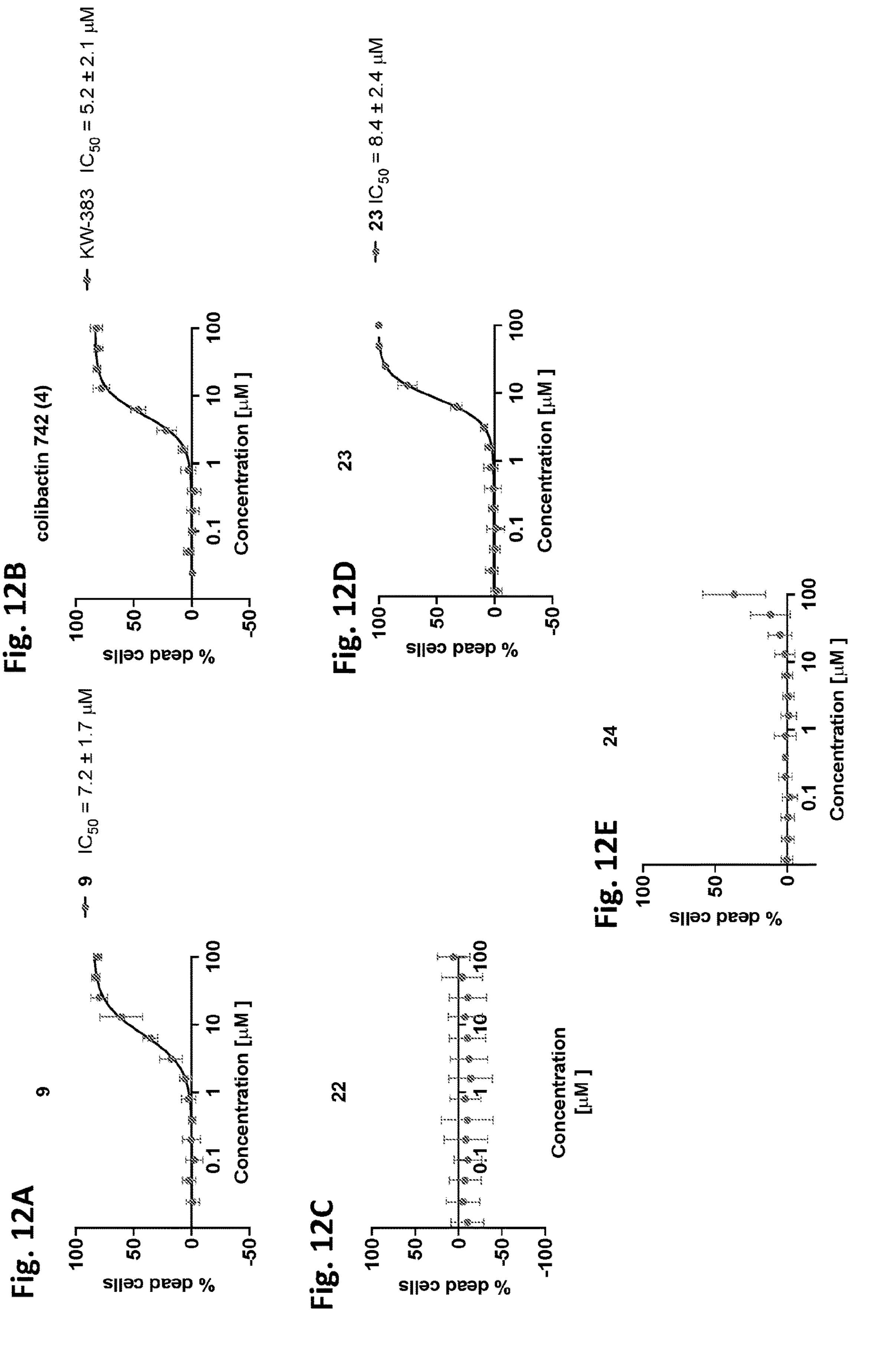

The present study then compared the cross-linking ability of colibactin 742 (4) and 9 at pH 5.0 (FIG. 6B) and pH 7.0 (FIG. 6C) over the range of concentrations 1 nM-100 μM. It was found that the linear precursor 9 and colibactin 742 (4) induced stable ICLs at pH 7.0 (FIG. 6C), a pH at which colibactin 770 (3) readily decomposes and fails to produce detectable levels of ICLs. While colibactin most likely induces DNA cross-links via nucleotide addition to the spirocyclic cyclopropanes, other sites of DNA alkylation (such as 1,2-addition to the cyclic imine) have been proposed. The control compounds 22, 23, and 24 all failed to form DNA ICLs, confirming that the cross-linking occurs via the cyclopropane ring-opening mechanism and that both electrophilic pharmacophores are required (FIG. 11).

Example 3: Colibactin Derivatives are Capable of Inducing Cell Death in Cancer Cell Line Experiments to determine if the cyclized and linear forms (colibactin 742 (4) and 9, respectively) are cytotoxic were conducted. As discussed above, the timing of the cyclization events that form the colibactin warheads is not known. To probe this, the instant study measured the cytotoxicity of both the linear precursor 9 and colibactin 742 (4) toward human cervical cancer cells (HeLa). The compounds were incubated for 72 h at concentrations ranging from 24 nM to 100 μM. Cell viability was measured using CellTiter GLO assay and normalized to tamoxifen (60 μM, set at 100% effect) and methyl sulfoxide (DMSO, set at 0% effect). Both compounds were cytotoxic, with half-maximal inhibitory potencies ($IC_{50}$s) of 7.2±1.7 μM and 5.2±2.1 μM for the linear precursor 9 and colibactin 742 (4), respectively (FIGS. 12A-12E). These data indicate that the generation of the colibactin warhead may occur spontaneously following export from the producing bacteria. Additionally, this observation further supports the notion that while the C36-C37 1,2-diketone may dictate colibactin's half-life within the gut, it may not play a critical role in DNA damage.

Figure 7A:
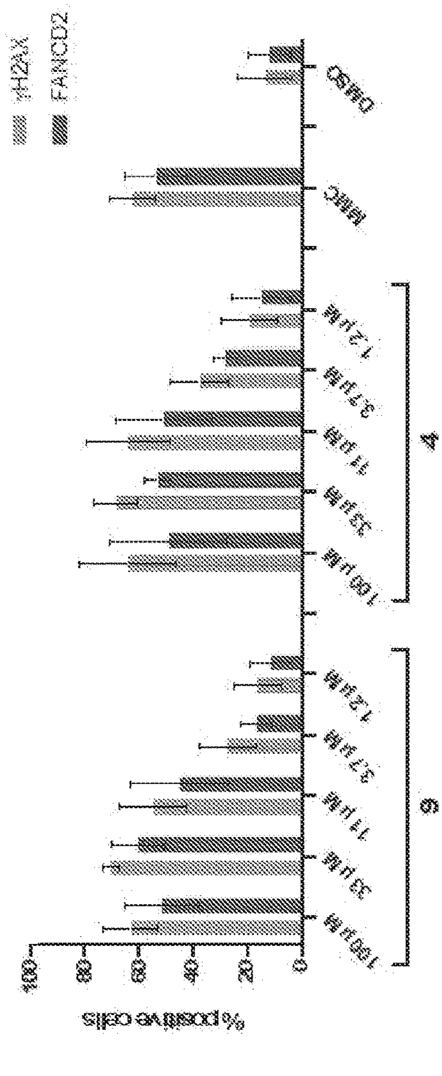
FIGS. 7A-7B evaluates the Colibactin 742 (4) and its linear precursor 9 recapitulate the clb phenotype.

The present study then probed the DNA damage response that was activated following exposure to colibactin 742 (4) or its linear precursor 9. In mammalian cells, DNA interstrand cross-links (ICLs) are repaired by the Fanconi anemia pathway, and activation of this pathway is observed when eukaryotic cells are infected with $clb^+$ bacteria. Upon detection of an ICL, the Fanconi anemia protein D2 (FANCD2) is activated by monoubiquitinylation and recruited to the ICL to coordinate repair. Following initiation of repair, a double-strand break (DSB) is generated, which in turns triggers the formation of phospho-SER139-H2AX (γH2AX) nuclear foci. It is known that HeLa cells infected with $clb^+$ *E. coli* displayed FANCD2 and γH2AX foci, similar to cells that have been treated with the cross-linking agent mitomycin C (MMC, 2.5 μM). Consequently, the instant study probed for activation of FANCD2 and γH2AX by immunofluorescence imaging in cells treated with 4 or 9. Using conditions that closely mimic the bacterial coinfection experiments, the instant study treated HeLa cells with colibactin 742 (4) (1-100 μM), the linear precursor 9 (1-100 μM), or MMC (150 nM, higher concentrations of MMC reduced cell viability) for 4 h. The cells were then washed and cultured for a further 20 h. Following treatment with 11 μM of either the linear precursor 9 or colibactin 742 (4), there was a four-fold increase in the number of positive cells for FANCD2 and γH2AX foci, which was comparable to the MMC treatment (FIG. 7A). Higher concentrations (>33 μM) of colibactin 742 (4) or 9 induced cell death and thus a decrease in positive cells. Thus, the synthetic compounds 4 and 9 induce a similar activation of the eukaryotic DNA damage response as $clb^+$ *E. coli.*

Figure 7B:
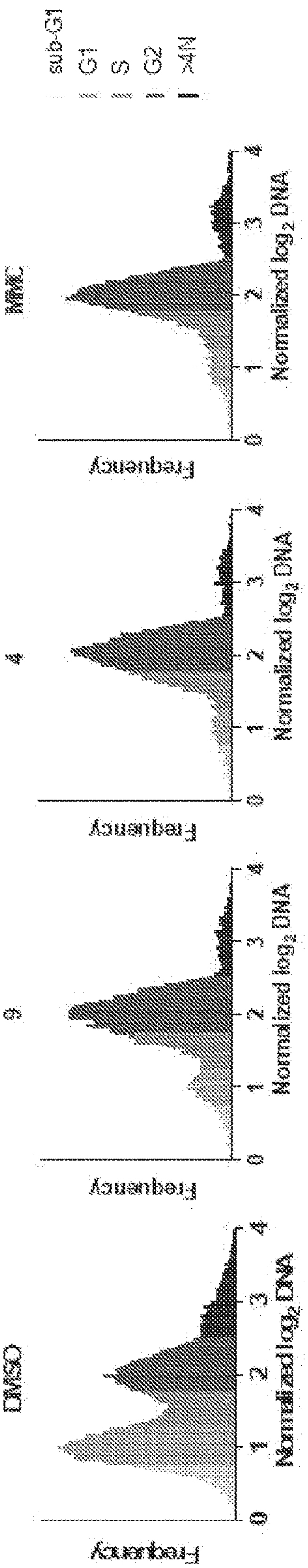
Figure 13:
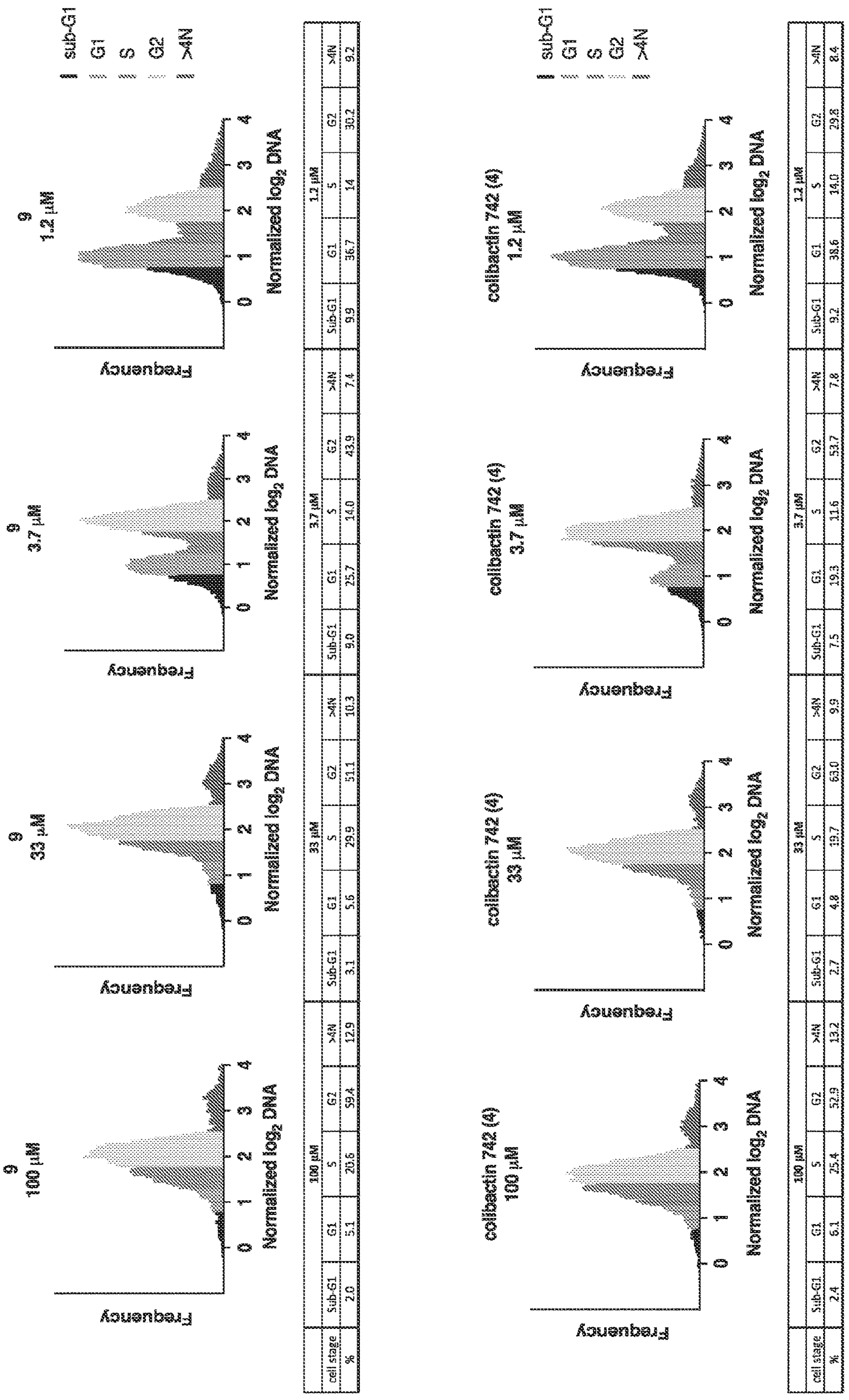
FIG. 13 shows that treatment of HeLa cells with 9 (1.2-100 μM) or colibactin 742 (4) (1.2-100 μM) induces cell cycle arrest at G2, according to some embodiments. DNA content histograms and quantification of the subpopulation of the histograms.

It has also been reported that $clb^+$ bacteria induce cell cycle arrest at the G2/M phase and eventual mitotic catastrophe. Using cell cycle analysis, the instant study determined that cells treated with >11 μM of either the linear precursor 9 or colibactin 742 (4) exhibited accumulation of cells in $G_2$, which is indicative of cell cycle arrest at $G_2$/M (FIG. 7B shows histograms of cells treated with 11 μM of colibactin 742 (4) or 9, additional histograms are presented in FIG. 13).

Figure 14:
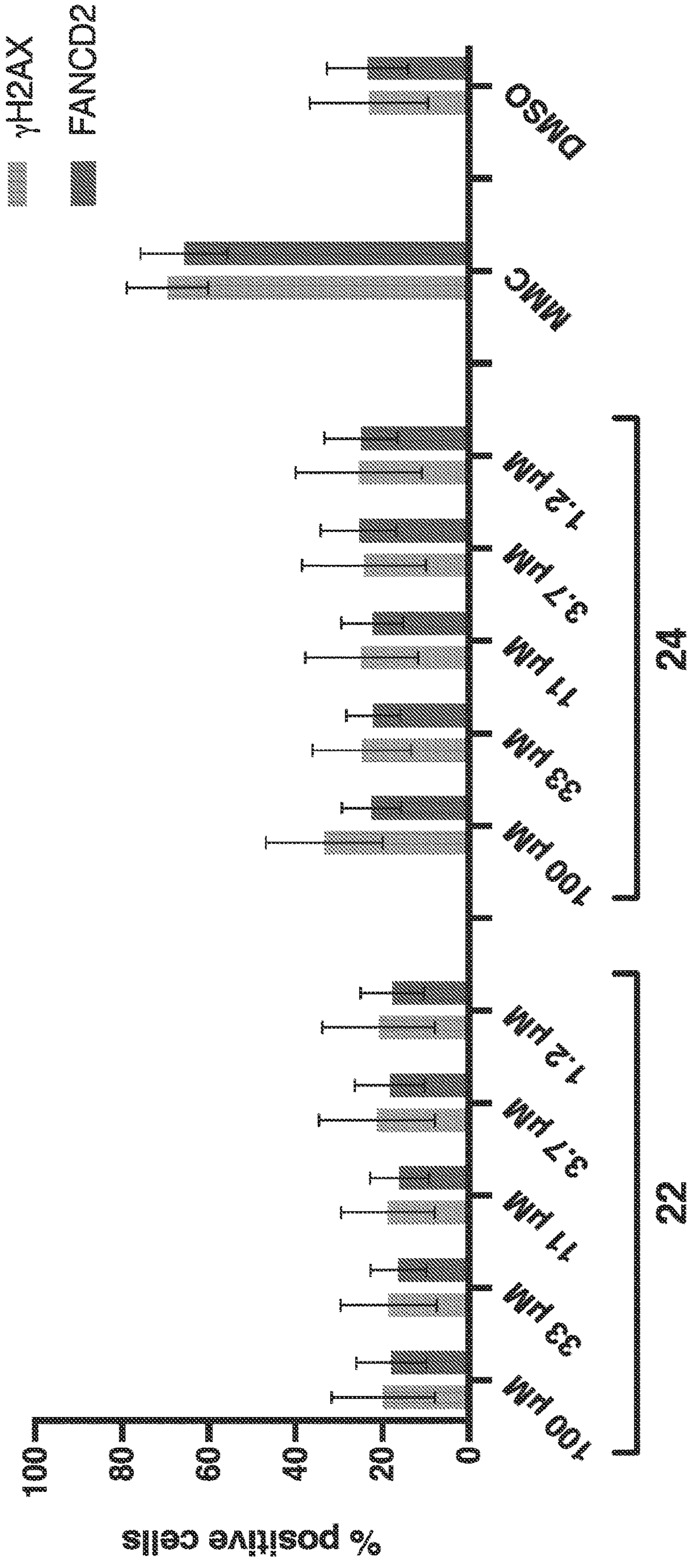
FIG. 14 shows the results of the treatment of Hela cells with 22 and 24 and the analysis for FANCD2 and γH2AX foci according to some embodiments. As shown herein, treatment with 22 or 24 did not induce either FANCD2 and γH2AX foci. HeLa cells were treated with 22 (1-100 μM), 24 (1-100 μM) or MMC (0.15 μM) for 4 h, and then washed and incubated for 20 h. Cells were considered positive when >5 foci were formed. Means and standard deviations of results from at least 3 independent experiments are shown.
Figure 15:
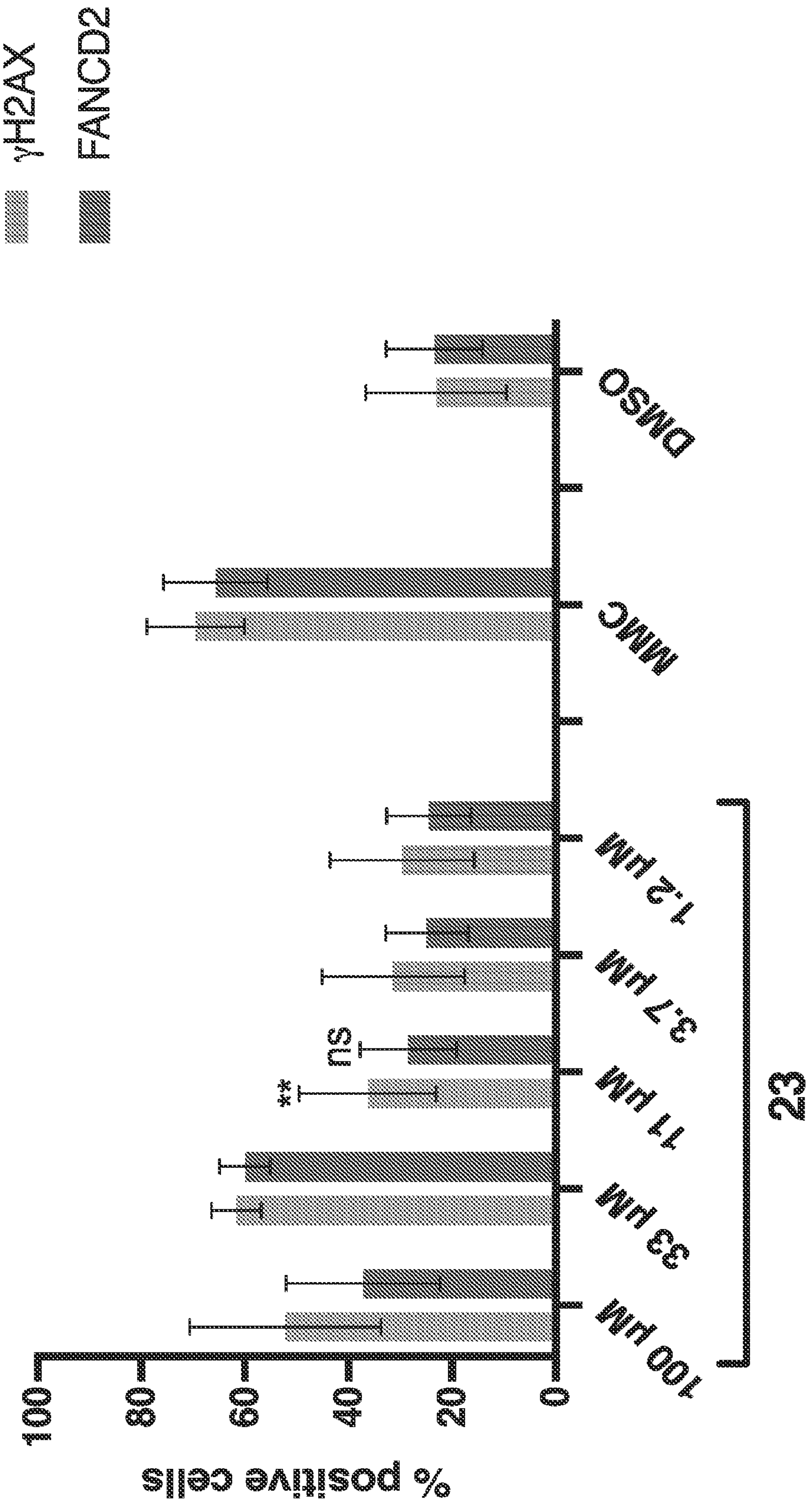
FIG. 15 shows the results of treatment of HeLa cells with 23 and the analysis for FANCD2 and γH2AX foci according to some embodiments. As shown in the figure, the treatment with 23 induces both FANCD2 and γH2AX foci at higher concentrations. HeLa cells were treated for with 23 (1-100 μM) or MMC (0.15 μM) for 4 h, and then washed and incubated for 20 h. Cells were considered positive when >5 foci were formed. Means and standard deviations of results from at least 3 independent experiments are shown. Statistical significance was assessed by an unpaired, two-tailed t test. P values: **<0.002, ns=not significant >0.05.

Finally, the instant study evaluated the biological responses of the gem-dimethyl derivative 22 and the left- and right-hand fragments 23 and 24, respectively. Interestingly, the left-hand fragment 23 was cytotoxic ($IC_{50}$=8.4±2.4 μM, see FIGS. 12A-12E) while the right-hand fragment 24 and the gem-dimethyl derivative 22 showed no toxicity. Without wishing to be limited by any theory, one interpretation of this result is that the left-hand fragment is responsible for the initial alkylation event, and this may position the remaining electrophile for the second alkylation. While the gem-dimethyl derivative 22 and the right-hand fragment 24 did not induce γH2AX or FANCD2 foci formation in Hela cells (FIG. 14), the instant study found that the left-hand fragment 23 did induced significant γH2AX foci formation at 11 μM (FIG. 15) but not FANCD2. Upon treatment with a higher concentration of 23 (33 μM), the instant study observed a three-fold increase in the number of positive cells (with respect to DMSO) for both FANCD2 and γH2AX foci (FIG. 15). Without wishing to be limited by any theory, this is likely due to the formation and accumulation of monoalkylation products, which are known to stimulate production of γH2AX[5] and subsequent recruitment of FANCD2 to chromatin at stalled replication forks.

Example 4

$clb^+$ Bacteria are capable of inducing DNA ICLs and tumorigenesis, and have been causally linked to tumors in human patients. While evidence suggests these effects derive from colibactin, to date, the direct study of colibactin itself has not been possible due to its instability toward oxidation and decomposition.

Consistent with this instability, when eukaryotic cells were treated with synthetic colibactin 770 (3a), no genotoxicity was observed. Monitoring solutions of colibactin 770 (3a) in aqueous buffer at pH 7.4 and 37° C. revealed that colibactin readily degraded within 2 h (FIG. 9). This lack of genotoxicity in cellular systems with synthetic colibactin 770 (3a) potentially explains the lack of activity seen when clb bacterial supernatant also failed to induce genotoxicity. The instant findings suggest colibactin's exquisite instability likely underlies these observations.

However, when colibactin 742 (4) and its linear precursor 9 were prepared-which are stable under physiological conditions-both were found to cross-link exogenous DNA and induce a DNA damage repair phenotype in within cellular assays. These results have several non-limiting implications in colibactin's chemistry and biology. First, these results suggest that the C36-C37 1,2-diketone in colibactin 770 (3a) is not essential in DNA ICL generation, an important finding given that this is the locus of instability in the natural product. Second, the instant data suggest that the C36-C37 1,2-diketone dictates colibactin's half-life under physiological conditions and is the origin of the difficulties encountered in studying colibactin directly. Finally, the instant results show that molecules structurally-similar to colibactin are capable of entering eukaryotic cells without active bacterial trafficking. Prior studies showed that direct cell-to-cell contact between the host and clb bacteria was required to observe genotoxicity and it is hypothesized that active bacterial trafficking is essential for colibactin to induce genotoxicity. While the instant studies by no means exclude trafficking occurs, they do show that it is not required and that colibactin stability may be a more pertinent phenomenon regulating colibactin genotoxicity. Understanding these phenomena has implications in preventing microbial induced oncogenesis and is a crucial and underexplored aspect of colibactin pharmacology. Regardless, the hypotheses of bacterial active trafficking and colibactin instability both recognize that cellular proximity is a key factor in colibactin genotoxicity and this phenomenon will likely prove foundational in understanding and preventing microbiome induced tumorigenesis.

The instant study also prepared a series of compounds (22, 23, and 24) and evaluated their DNA cross-linking and genotoxic capabilities. These studies provide convincing evidence that colibactin's mode of action involves DNA alkylation via a cyclopropane-opening mechanism (seen in lack of DNA alkylation with 22). This work also indicates that both cyclopropane containing warheads are required to induce DNA cross-links as neither the left- or right-hand warhead (23 and 24 respectively) were able to induce DNA ICLs—a critical component of the clb phenotype.

Figures 8A, 8B:
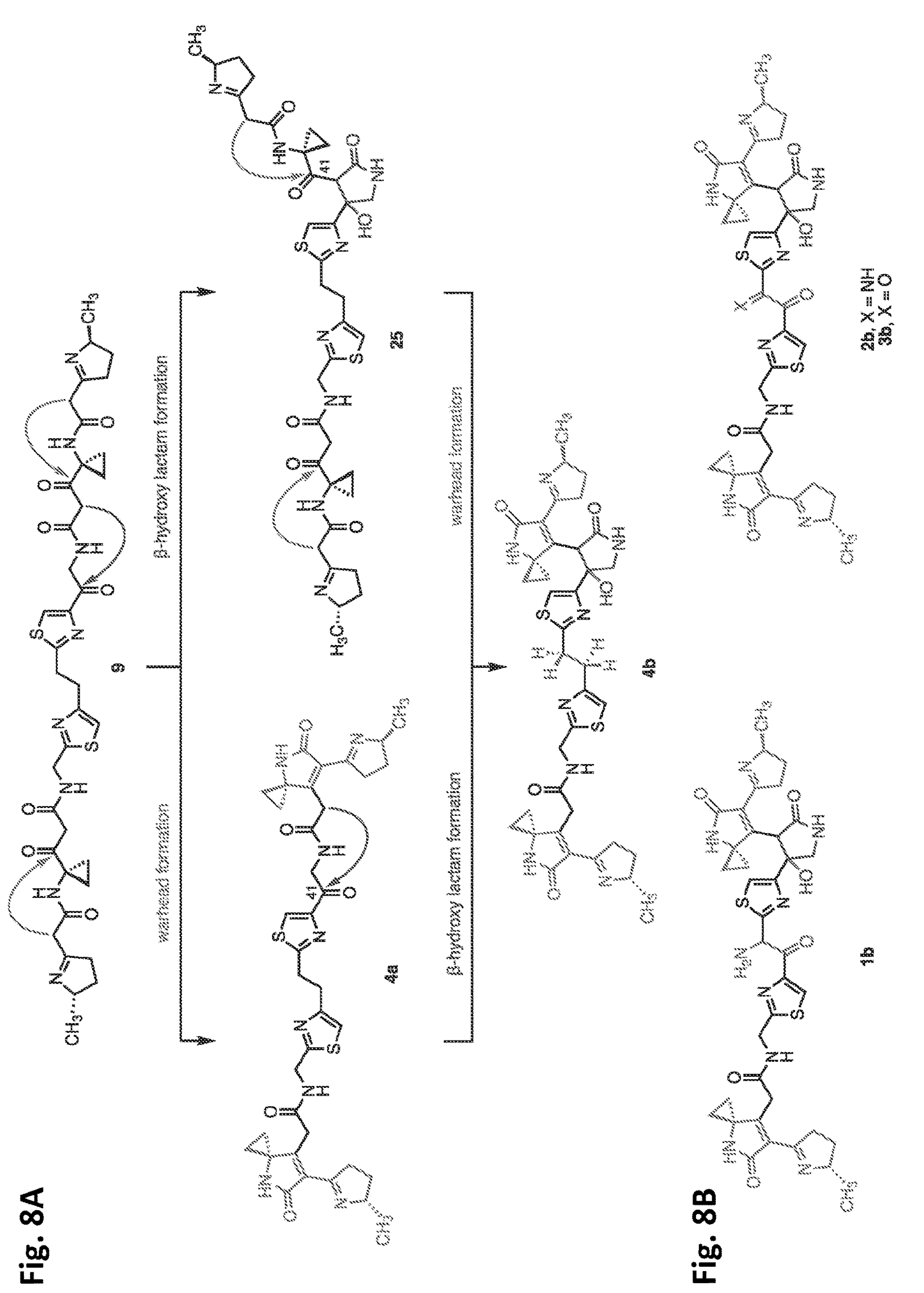
FIG. 8A depicts the proposed pathways for the formation of the ring isomer of colibactin 742 (4b).
FIG. 8B shows structures 1b, 2b, or 3b colibactin may exist as predicted from the reactivity of 9.

An unexpected and significant structural finding is that the linear precursor 9 readily converts to the β-hydroxy lactam 4b under physiological conditions. This cyclization appears to be irreversible and may occur before or after the formation of the right-hand warhead (FIG. 8A). This suggests that the structure of colibactin may be represented by either 1b, 2b, or 3b (FIG. 8B), or a mixture of these and the chain isomers 1a-3a. This finding was undetected by the MS-based methods employed earlier. Colibactin has been modeled in the minor groove of DNA in the chain form (3a, FIG. 1A), but the data here suggest the β-hydroxy lactam isomers (1b, 2b, and 3b) may be the dominant species in solution. This structural refinement may inform studies that probe the DNA sequence specificity of colibactin and improve the knowledge of the basis of colibactin's mutational signature.

Additionally, while the genotoxic phenotype induced by colibactin 742 (4) and its linear precursor 9 indicate that the C36-C37 diketone is not required to induce DNA ICLs, it does not fully explore its biological significance. The chemical identity of the C36-C37 spacer at the time of cross-linking is currently unknown, but the dramatic effect of this residue on the stability of the molecule argues for further chemical studies of this system. In fact, the redox capabilities of this potential pharmacophore may underpin currently unknown biological effects of colibactin.

Another underexplored role of colibactin in human health and disease is the effect of colibactin on other commensal microbes within the gut. The clb gene cluster is broadly distributed across Enterobacteriaceae, and while studying the interactions of $clb^+$ bacteria with other commensals would allow for a topical knowledge of the microbe-microbe interactions it does not allow the effects of colibactin to be distinguished from other effector molecules and bacterial cross-talk. However, with a stable analog of colibactin now in hand, it is possible to directly study the effects of colibactin decoupled from other factors produced by the diverse array of bacteria that possess the clb gene cluster.

In summary, the instability of colibactin prevents its direct use in cell-based assays. The instant study reported the synthesis of the stable derivative—colibactin 742 (4)—and validated this compound as a chemical probe of clb genotoxicity. Colibactin 742 (4), as well as its linear precursor 9, are capable of forming stable DNA cross-links analogous to those generated by $clb^+$ bacteria. Moreover, these compounds are shown to be cytotoxic to mammalian cells at μM concentrations, induce formation of FANCD2 and γH2AX foci, and lead to cell cycle arrest at $G_2$/M phase, all in agreement with the bacterial phenotype. These studies have revealed a novel cyclization pathway that was undetected using previous MS-based methods and suggest colibactin exists, at least in part, as 1b, 2b, or 3b.

Example 5: General Methods and Materials

DNA Cross-Linking Assays

The 2686 bp pUC19 vector (circular) was purchased from New England Biolabs® (Ipswich, MA). Linearized pUC19 DNA was used for all DNA cross-linking assays. To prepare the linearized DNA, the 2686 bp pUC19 vector was linearized with 20 units/μg EcoRI-HF® (New England Biolabs®) and the linearized DNA was purified using a PCR clean-up kit (New England Biolabs®), eluted into 10 mM Tris (pH 8.0), and quantified using a nanodrop. For each reaction with colibactin 770 (3), or the linear precursor 9, or colibactin 742 (4), 200 ng of linearized pUC19 DNA (15.4 μM base pairs) was incubated with the respective compound in concentrations ranging from 200 μM-1 nM in a total volume of 20 μL. Compounds were diluted in DMSO such that each reaction contained a fixed 5% DMSO concentration. Reactions were conducted in 10 mM sodium citrate buffer (pH 5.0) or 10 mM sodium phosphate buffer (pH 7.0). Pure cisplatin (Biovision®) and DMSO vehicle were used as positive and negative controls, respectively. Stock solutions of cisplatin in DMSO were prepared immediately before use. Controls containing 200 ng of circular pUC19 DNA (15.4 μM base pairs) and 100 μM cisplatin or DMSO vehicle in 10 mM sodium citrate (pH 5) buffer with a final DMSO concentration of 5% were prepared simultaneously. Reactions were conducted for 4 h at 37° C. The DNA was stored at −20° C. until electrophoretic analysis or follow-up experiments.

Gel Electrophoresis

For each DNA sample, the DNA concentration was preadjusted to 10 ng/μL. For native gels, 5 μL (50 ng) of DNA was removed and mixed with 1.5 μL of 6× purple gel loading dye, no SDS (New England Biolabs®), and loaded onto 1% agarose Tris Borate EDTA (TBE) gels. For denaturing gels, samples of 5 μL (50 ng) of DNA were removed and separately mixed with 15 μL of 0.2% denaturing buffer (0.27% sodium hydroxide, 10% glycerol, and 0.013% bromophenol blue) or 0.4% denaturing buffer (0.53% sodium hydroxide, 10% glycerol, and 0.013% bromophenol blue) in an ice bath. The mixed DNA samples were denatured at 4° C. for 10 min and then immediately loaded onto 1% agarose TBE gels. All gel electrophoresis was conducted at 90 V for 1.5 h, unless otherwise noted. The gel was stained with SybrGold (Thermo Fisher) for 2 h.

Mammalian Cell Lines and Reagents

The HeLa cell line was obtained from American Type Culture Collection (ATCC). HeLa cells were grown in Dulbecco's Modified Eagle Medium (DMEM, with 4.5 g/L glucose, L-glutamine & sodium pyruvate, Corning) supplemented with fetal bovine serum (FBS, Life Technologies, 10%) and penicillin-streptomycin (0.1%, Life Technologies) at 37° C. in a 95% humidity atmosphere under 5% $CO_2$ environment. The cells were split after 90% confluence was reached. Mitomycin C (cat. #11435) and tamoxifen (cat. #13258) were purchased from Cayman Chemical. Antibodies for immunofluorescence were purchased from Upstate (phospho-specific H2AX, 05-636), Novus Biologicals (FANCD2, NB100-182), or Molecular Probes [Alexa Fluor 488-conjugated goat anti-mouse immunoglobulin G (IgG) and Alexa Fluor 647-conjugated goat anti-rabbit IgG].

Cell Viability Assays

Hela cells were grown in Dulbecco's Modified Eagle Medium (DMEM) supplemented with fetal bovine serum (FBS, 10%) and penicillin-streptomycin (0.1%) at 37° C. in a 95% humidity atmosphere under 5% $CO_2$ environment. Cytotoxicity was determined using a CellTiter-GLO Assay. Cells were seeded at a density of 400 cells to achieve total well volumes of 20 μL in 384-well plates (black with an optically clear bottom, Greiner Bio One 781091) using a Thermo Combidrop liquid dispenser and grown for 16 h at 37° C., 5% $CO_2$. Cells were grown for 24 h, followed by the addition of test compounds using an Echo acoustic liquid handler (Labcyte). For each tested drug concentration, a 20 nL aliquot of the 1000× stock was added to 20 μL of cells to provide a final DMSO concentration of 0.1%. The compounds were incubated for 72 h at concentrations ranging from 24 nM to 100 μM. Each plate contained negative vehicle control wells (0.1% DMSO) and positive control wells (60 μM tamoxifen). After 72 h, the cells were treated with 10 μL CTG reagent. The plates were shaken for 1 min at 1100 rpm, then then was incubated for 30 min at 23° C. in the dark. The resulting luminescence was measured using a plate reader (Infinite M1000, TECAN Group AG). Biological triplicates, each measured four times (N=12), for each compound were recorded for each concentration and $IC_{50}$ values were determined using Prism 9 (Graph Pad) fit with a four parameters nonlinear regression.

Immunofluorescence Assays

Cells were seeded at a density of 3500 cells per well to achieve total well volumes of 20 μL in 384-well plates (black with an optically clear bottom, Greiner Bio One 781091) using a Thermo Combidrop liquid dispenser. Cells were grown for 24 h, followed by the addition of test compounds using an Echo acoustic liquid handler (Labcyte). For each tested drug concentration, a 20 nL aliquot of the 1000× stock was added to 20 μL of cells to provide a final DMSO concentration of 0.1%. The compounds were incubated for 4 h at concentrations ranging from 1.2 μM to 100 μM in growth medium, at 37° C., 5% $CO_2$. Each plate contained negative vehicle control wells (0.1% DMSO) and positive control wells (0.15 μM Mitomycin C, MMC). After 4 h incubation, the cells were washed once with Dulbecco's Phosphate-buffered solution (DPBS, Life Technologies), then fresh growth medium was added. The cells were incubated for 20 h, fixed, and subjected to immunofluorescence imaging.

Immunofluorescence Imaging

Cells were fixed with 4% paraformaldehyde (PFA) (Electron Microscopy Sciences) in the presence of 0.02% Triton X-100 at room temperature (RT) for 20 min and then incubated in permeabilization/blocking solution [10% FBS and 0.5% Triton X-100 in phosphate-buffered saline (PBS)] at RT for 1 h. Primary antibodies were diluted 1:500 in permeabilization/blocking solution and used to stain cells at 4° C. overnight. Secondary antibodies were diluted 1:1000 in permeabilization/blocking solution and used to stain cells at room temperature for 1 h. DNA was counterstained with Hoechst 33342. Cells were imaged using the InCell 2200 Imaging System (GE Corp.) and analyzed using InCell Analyzer software (GE Corp.) to quantify the number of γH2AX and FANCD2 foci. Cells were counted as positive for focus formation when 5 foci/nucleus were detected.

General Experimental Procedures.

All reactions were performed in single-neck, flame-dried round-bottomed flasks fitted with rubber septa under a positive pressure of argon, unless otherwise noted. Air- and moisture-sensitive liquids were transferred via syringe or stainless-steel cannula, or were handled in a nitrogen-filled drybox (working oxygen level <5 ppm). Flash-column chromatography was performed as described by Still et al. (Still, W. C. et al., *J. Org. Chem.* 1978, 43, 2923-2925), employing silica gel (60 Å, 40-63 μm particle size) purchased from SiliCycle. Analytical thin-layered chromatography (TLC) was performed using glass plates pre-coated with silica gel (0.25 mm, 60 Å pore size) impregnated with a fluorescent indicator (254 nm). TLC plates were visualized by exposure to ultraviolet light (UV) or aqueous potassium permanganate solution ($KMnO_4$), followed by brief heating on a hot plate (120° C., 10-15 s).

Materials

Commercial solvents and reagents were used as received with the following exceptions. Dichloromethane, diethyl ether (ether), N,N-dimethylformamide, tetrahydrofuran, and toluene were purified according to the method of Pangborn et al. (*Organometallics* 1996, 15, 1518-1520, the entirety of which is hereby incorporated by reference). Triethylamine was distilled from calcium hydride under an atmosphere of argon immediately before use. N,N-Di-iso-propyl ethylamine and triethylamine were distilled from calcium hydride and was stored under nitrogen. The intermediates S10, (Healy, A. R. et al., *J. Am. Chem. Soc.* 2016, 138, 15563-15570, the entirety of which is hereby incorporated by reference), S16 (Healy, A. R. et al., *J. Am. Chem. Soc.* 2016, 138, 5426-5432, the entirety of which is hereby incorporated by reference), 14 (Xue, M. et al., *Science* 2019, 365, the entirety of which is hereby incorporated by reference), and 11 (Xue, M. et al.) were prepared according to published procedures. Powdered 3 Å molecular sieves were activated by heating in vacuo within the reaction vessel immediately prior to use.

Instrumentation

Proton nuclear magnetic resonance ($^1H$ NMR) spectra were recorded at 600, 500, or 400 megahertz (MHz) at 23° C., unless otherwise noted. Chemical shifts are expressed in parts per million (ppm, 8 scale) downfield from tetramethylsilane and are referenced to residual proton in the NMR solvent ($CDHCl_2$, δ 5.32; $CHCl_3$, δ 7.26; $CD_2HOD$, δ 3.33; $CD_3S(O)CD_2H$, δ 2.50). Data are represented as follows: chemical shift, multiplicity (s=singlet, d=doublet, t=triplet, q=quartet, m=multiplet and/or multiple resonances, br=broad, app=apparent), coupling constant in Hertz (Hz), integration, and assignment. Proton-decoupled carbon nuclear magnetic resonance spectra ($^{13}C$ NMR) were recorded at 151 or 126 MHz at 23° C., unless otherwise noted. Chemical shifts are expressed in parts per million (ppm, 8 scale) downfield from tetramethylsilane and are referenced to the carbon resonances of the solvent ($CD_2Cl_2$, δ 53.8; $CDCl_3$, δ 77.2; $CD_3OD$, δ 49.0; $CD_3S(O)CD_3$, δ 39.5). Heteronuclear single quantum coherence (HSQC) spectra were recorded at 600 MHz at 23° C., unless otherwise noted. $^{13}C$ NMR and HSQC data are combined and represented as follows: chemical shift, carbon type [obtained from HSQC experiments]. Attenuated total reflectance Fourier transform infrared (ATR-FTIR) spectra were obtained using a Thermo Electron Corporation Nicolet 6700 FTIR spectrometer referenced to a polystyrene standard. Data are represented as follows: frequency of absorption ($cm^{-1}$), intensity of absorption (s=strong, m=medium, w=weak, br=broad). High-resolution mass spectrometry (HRMS) were obtained on a Waters UPLC/HRMS instrument equipped with a dual API/ESI high-resolution mass spectrometry detector and photodiode array detector. Unless otherwise noted, samples were eluted over a reverse-phase C18 column (1.7 μm particle size, 2.1×50 mm) with a linear gradient of 5% acetonitrile-water containing 0.1% formic acid→95% acetonitrile-water containing 0.1% formic acid for 1 min, at a flow rate of 600 μL/min.

Example 6: Synthetic Procedures

Synthesis of the Aldehyde S19

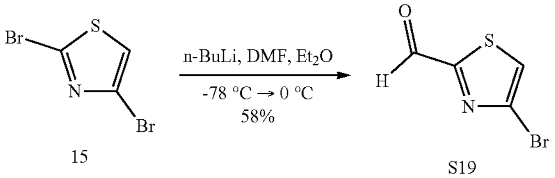 [SMILES: Brc1csc(Br)n1 ; O=Cc1nc(Br)cs1 ; "S19"]

15

S19

A solution of n-butyllithium in hexanes (2.36 M, 8.37 mL, 1.20 equiv) was added dropwise via syringe to a solution of 2,4-dibromothiazole 15 (4.00 g, 16.5 mmol, 1.00 equiv) in ether (165 mL) at −78° C. The reaction mixture was stirred for 15 min at −78° C. N,N-Dimethylformamide (2.54 mL, 33.0 mmol, 2.00 equiv) was then added dropwise via syringe at −78° C. The reaction mixture was stirred for 30 min at −78° C. The resulting mixture was then placed in an ice bath. The reaction mixture was stirred for 1 h at 0° C. The product mixture was diluted sequentially with saturated aqueous ammonium chloride solution (150 mL) water (50 mL). The resulting biphasic mixture was transferred to a separatory funnel and the layers that formed were separated. The aqueous layer was extracted with ether (2×75 mL). The organic layers were combined and the combined organic layers were washed with saturated aqueous sodium chloride solution (2×100 mL). The washed organic layer was dried over sodium sulfate. The dried solution was filtered and the filtrate was concentrated. The residue obtained was purified by automated flash-column chromatography (eluting with hexanes initially, grading to 40% ether-hexanes, linear gradient) to provide the aldehyde S19 as a white solid (1.84 g, 58%).

NMR spectroscopic data for S19 obtained in this way were in agreement with those previously reported (Pop, L. et al., *Tetrahedron Asymmetry* 2012, 23, 474-481).

Synthesis of the Bromo Alcohol 16

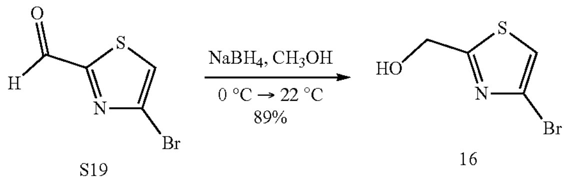 [SMILES: O=Cc1nc(Br)cs1 ; OCc1nc(Br)cs1 ; "S19"]

S19

16

Sodium borohydride (1.87 g, 49.5 mmol, 1.90 equiv) was added in three equal portions to a solution of the aldehyde S19 (5.00 g, 26.0 mmol, 1.00 equiv) in anhydrous methanol (59 mL) at 0° C. The reaction mixture was stirred for 10 min at 0° C. min. The reaction mixture was then warmed to 22° C. over 30 min. The product mixture was diluted sequentially with saturated aqueous ammonium chloride solution (100 mL), water (25 mL), and ethyl acetate (75 mL). The resulting biphasic mixture was transferred to a separatory funnel and the layers that formed were separated. The aqueous layer was extracted with ethyl acetate (2×50 mL). The organic layers were combined and the combined organic layers were washed with saturated aqueous sodium chloride solution (50 mL). The washed organic layer was dried over sodium sulfate. The dried solution was filtered and the filtrate was concentrated. The residue obtained was purified by automated flash-column chromatography (eluting with hexanes initially, grading to 40% ether-hexanes, linear gradient) to afford the bromo alcohol 16 as a white solid (4.50 g, 89%).

NMR spectroscopic data for 16 obtained in this were in agreement with those previously reported (Nicolaou, K. C. et al., *Bioorganic Med. Chem.* 1999, 7, 665-697).

Synthesis of the Silyl Ether S20

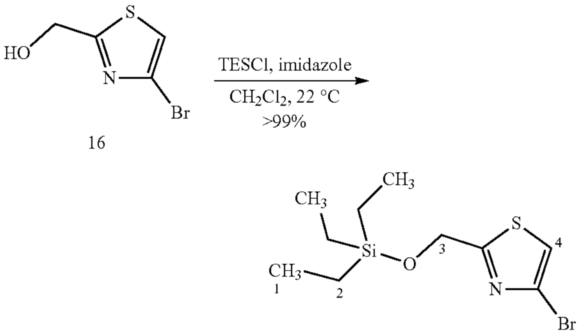

16

S20

Imidazole (2.81 g, 41.2 mmol, 2.00 equiv) and chlorotriethylsilane (4.50 mL, 26.8 mmol, 1.30 equiv) were added in sequence to a solution of the bromo alcohol 16 (4.00 g, 20.6 mmol, 1.00 equiv) in dichloromethane (69 mL) at 22° C. The reaction mixture was stirred for 90 min at 22° C. The product mixture was diluted with saturated aqueous ammonium chloride solution (100 mL) and the diluted solution was stirred for 5 min at 22° C. The layers that formed were separated, and the aqueous layer was extracted with dichloromethane (2×50 mL). The organic layers were combined and the combined organic layers were dried over sodium sulfate. The dried solution was filtered and the filtrate was concentrated. The residue obtained was purified by automated flash-column chromatography (dry loaded, eluting with hexanes initially, grading to 30% ether-hexanes, linear gradient) to afford the silyl ether S20 as a colorless oil (6.34 g, >99%).

$R_f$=0.33 (5% ether-hexanes; UV). $^1$H NMR (600 MHz, $CDCl_3$): δ 7.17 (s, 1H, $H_4$), 4.95 (s, 2H, $H_3$), 0.98 (t, J=8.0 Hz, 9H, $H_1$), 0.67 (q, J=8.0 Hz, 6H, $H_2$). $^{13}$C NMR (151 MHz, $CDCl_3$): δ 174.6 (C), 124.4 (C), 116.6 (CH), 62.9 ($CH_2$), 6.8 (3×$CH_3$), 4.5 (3×$CH_2$). IR (ATR-FTIR), $cm^{-1}$: 3296 (m), 3123 (w), 2974 (w), 2954 (m), 2910 (w), 2875 (m), 1485 (m), 1249 (m), 1184 (m), 1149 (s), 1082 (s), 1004 (m), 887 (m), 835 (m), 730 (s). HRMS-CI (m/z): $[M+H]^+$ calcd for $C_{10}H_{19}BrNONSSi$, 308.0135/310.0115; found, 308.0123/310.0104.

Synthesis of the Weinreb Amide 17

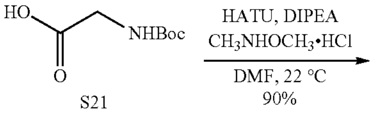

S21

-continued

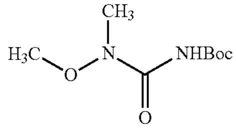

17

1-[Bis (dimethylamino) methylene]-1H-1,2,3-triazolo[4,5-b]pyridinium 3-oxide hexafluorophosphate (HATU, 15.6 g, 41.1 mmol, 1.20 equiv) and N,N-diisopropylethylamine (29.8 mL, 171 mmol, 5.00 equiv) were added in sequence to a solution of N,O-dimethylhydroxylamine hydrochloride (3.68 g, 37.7 mmol, 1.10 equiv) and S21 (6.00 g, 34.3 mmol, 1.00 equiv) in N,N-dimethylformamide (40 mL) at 22° C. The reaction mixture was stirred for 3 h at 22° C. The product mixture was diluted sequentially with dichloromethane (100 mL) and 1 μM aqueous sodium hydroxide solution (50 mL). The layers that formed were separated, and the aqueous layer was extracted with dichloromethane (3×50 mL). The organic layers were combined, and the combined organic layers were washed sequentially with water (3× 50 mL) and saturated aqueous sodium chloride solution (40 mL). The washed organic layer was dried over sodium sulfate. The dried solution was filtered and the filtrate was concentrated. The residue obtained was purified by automated flash-column chromatography (eluting with hexanes initially, grading to 80% ethyl acetate-hexanes, linear gradient) to afford the Weinreb amide 17 as a white solid (4.46 g, 90%).

NMR spectroscopic data for 17 obtained in this were in agreement with those previously reported (Breuer, C. et al., *Bioorganic Med. Chem. Lett.* 2018, 28 (11), 2008-2012).

Synthesis of the α-Aminoketone 18

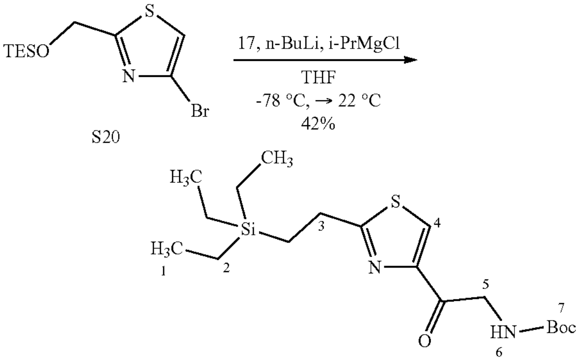

S20

18

A solution of n-butyllithium in hexanes (2.35 M, 9.10 mL, 21.4 mmol, 1.10 equiv) was added dropwise via syringe over 10 min to a solution of the silyl ether S20 (6.00 g, 19.5 mmol, 1.00 equiv; dried by azeotropic distillation from benzene (3×10 mL)) in ether (160 mL) at −78° C. The resulting solution was stirred for 30 min at −78° C. In a separate flask, a solution of iso-propylmagnesium chloride solution in tetrahydrofuran (2.00 M, 11.7 mL, 23.4 mmol, 1.20 equiv) was added dropwise via syringe over 10 min to a solution of the Weinreb amide 17 (5.10 g, 23.4 mmol, 1.20 equiv; dried by azeotropic distillation from benzene (3×10 mL)) in tetrahydrofuran (450 mL) at −78° C. The resulting solution was stirred for 30 min at −78° C. and then was transferred via cannula to solution of the thiazyl lithium reagent at −78° C. The resulting mixture was stirred at −78° C. for 30 min. The reaction mixture was then warmed to 22° C. over 1 h. The product mixture was diluted sequentially with saturated aqueous ammonium chloride solution (200 mL), water (75 mL), and ethyl acetate (200 mL). The layers that formed were separated, and the aqueous layer was extracted with ethyl acetate (2×100 mL). The organic layers were combined and the combined layers were washed with saturated aqueous sodium chloride solution. The washed organic layer was dried over sodium sulfate. The dried solution was filtered and the filtrate was concentrated. The residue obtained was purified by automated flash-column chromatography (eluting with hexanes initially, grading to 100% ether-hexanes, linear gradient) to afford the α-aminoketone 18 as colorless oil (3.16 g, 42%).

$R_f$=0.39 (30% ether-hexanes; UV). $^1$H NMR (600 MHz, $CD_2Cl_2$): δ 8.18 (s, 1H, $H_4$), 5.37 (s, 1H, $H_6$), 4.98 (s, 2H, $H_3$), 4.61 (d, J=5.1 Hz, 2H, $H_5$), 1.44 (s, 9H, $H_7$), 1.00 (t, J=8.0 Hz, 9H, $H_1$), 0.70 (q, J=8.0 Hz, 6H, $H_2$). $^{13}$C NMR (151 MHz, $CD_2Cl_2$): δ 190.5 (C), 174.9 (C), 156.2 (C), 153.0 (C), 126.3 (CH), 79.9 (C), 63.3 ($CH_2$), 49.4 ($CH_2$), 28.6 (3×$CH_3$), 7.0 (3×$CH_3$), 4.9 (3×$CH_2$). IR (ATR-FTIR), $cm^{-1}$: 3368 (m), 2953 (m), 2975 (m), 1885 (s), 1486 (m) 1367 (m), 1151 (s), 1082 (s), 729 (s). HRMS-CI (m/z): $[M+H]^+$ calcd for $C_{17}H_{31}N_2O_4SSi$, 387.1774; found, 387.1764.

Synthesis the Alcohol S22

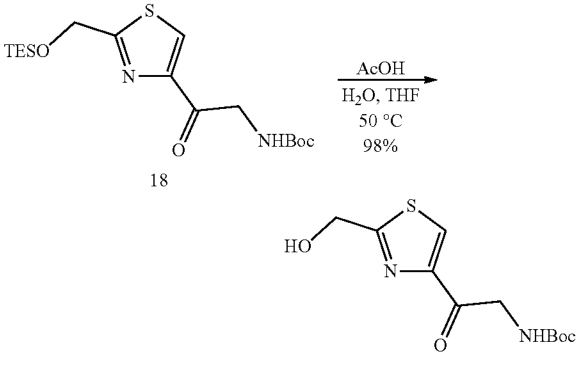

18

S22

Acetic acid (9.50 mL, 165 mmol, 71.0 equiv) was added to a solution of the α-aminoketone 18 (900 mg, 2.33 mmol, 1.00 equiv) in tetrahydrofuran (2.0 mL) and water (10 mL) at 22° C. The reaction mixture was warmed to 50° C. and stirred for 1 h. The product mixture was diluted sequentially with ethyl acetate (60 mL) and saturated aqueous sodium bicarbonate solution (30 mL). The layers that formed were separated, and the aqueous layer was extracted with ethyl acetate (3×20 mL). The organic layers were combined and the combined organic layers were washed with saturated aqueous sodium chloride solution. The washed organic layer was dried over sodium sulfate. The dried solution was filtered and the filtrate was concentrated. The residue obtained was purified by automated flash-column chromatography (eluting with 10% ethyl acetate-hexanes initially, grading to 100% ethyl acetate-hexanes, linear gradient) to afford the alcohol S22 as a white solid (619 mg, 98%).

NMR spectroscopic data for S22 obtained in this way were in agreement with those previously reported (Xue, M. et al., *Science* 2019, 365).

Synthesis of the Thiazole 13

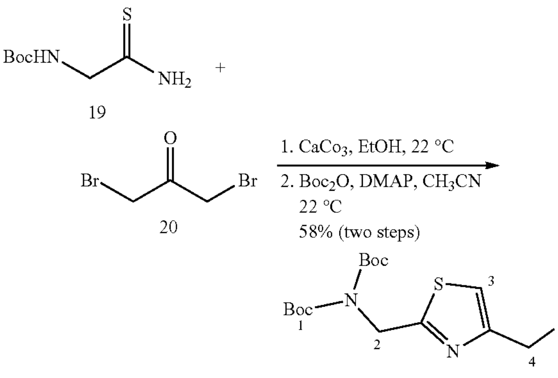

19

20

13

Calcium carbonate (10.4 g, 104 mmol, 6.00 equiv) and 1,3-dibromopropan-2-one (19) (2.30 mL, 22.5 mmol, 1.30 equiv) were added in sequence to a solution of 1,1-dimethylethyl N-(2-amino-2-thioxoethyl) carbamate (20; 3.30 g, 17.3 mmol, 1.00 equiv) in ethanol (130 mL) at 22° C. The reaction mixture was stirred for 12 h at 22° C. The product mixture was filtered through Celite. The Celite pad was washed with ethyl acetate (50 mL). The filtrates were combined and the combined filtrates were concentrated.

Di-t-Butyl dicarbonate (15.1 g, 69.2 mmol, 4.00 equiv) and (4-dimethylamino) pyridiune (DMAP, 423 mg, 3.46 mmol, 0.20 equiv) were in sequence to a solution of the residue obtained in the preceding step (nominally 17.3 mmol) in acetonitrile (43 mL) at 22° C. The reaction mixture was stirred for 12 h at 22° C. The product mixture was diluted sequentially with ethyl acetate (150 mL) and saturated aqueous sodium bicarbonate solution (75 mL). The layers that formed were separated, and the aqueous layer was extracted with ethyl acetate (2× 75 mL). The organic layers were combined and the combined organic layers were washed with saturated aqueous sodium chloride solution (75 mL). The washed organic layer was dried over sodium sulfate. The dried solution was filtered, and the filtrate was concentrated. The residue obtained was purified by automated flash-column chromatography (eluting with hexanes initially, grading to 50% ether-hexanes, linear gradient) to afford the imide 13 as a white solid (4.10 g, 58%).

$R_f$=0.54 (25% ethyl acetate-hexanes; UV). $^1$H NMR (500 MHz, $CDCl_3$): δ 7.21 (s, 1H, H3), 5.04 (s, 2H, $H_2$), 4.52 (s, 2H, $H_4$), 1.46 (s, 18H, $H_1$). $^{13}$C NMR (126 MHz, $CDCl_3$): δ 13C NMR (126 MHz, cdcl3) δ 169.2 (C), 151.7 (2×C), 117.8 (CH), 117.5 (C), 83.5 (2×C), 48.0 ($CH_2$), 28.0 (6×$CH_3$), 27.1 ($CH_2$). IR (ATR-FTIR), $cm^{-1}$: 3015 (w), 2975 (m), 1292 (m), 1751 (s), 1696 (s), 1479 (m), 1457 (m), 1367 (s), 1340 (m), 1256 (m), 1228 (m), 1135 (s), 936 (m), 853 (m), 284 (m), 585 (w), 468 (w). HRMS-CI (m/z): $[M+Na]^+$ calcd for $C_{15}H_{24}BrNaN_2O_4S$, 431.0439; found, 431.0425.

Synthesis of the Bis(Thiazole) 12

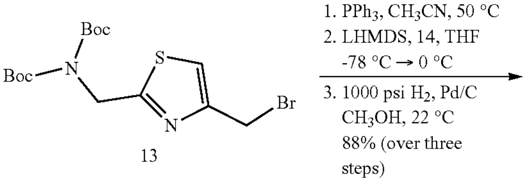

13

-continued

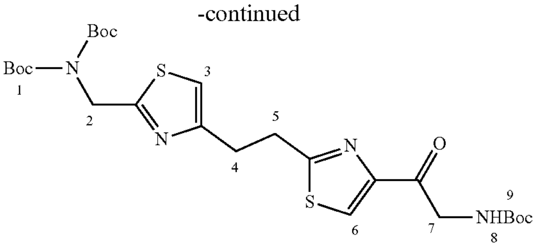

12

Triphenylphosphine (451 mg, 1.72 mmol, 1.10 equiv) was added to a solution of the imide 13 (636 mg, 1.56 mmol, 1.00 equiv) in acetonitrile (5.0 mL) at 22° C. The reaction mixture was placed in an oil bath that had been preheated to 50° C. The reaction mixture was stirred and heated for 2 h at 50° C. The product mixture was cooled to 22° C. over 30 min. The cooled solution was concentrated. The residue obtained was triturated with ice-cold ether (3×5.0 mL). The resulting white powder was dried in vacuo and used directly in the next step.

A solution lithium bis(trimethylsilyl) amide in tetrahydrofuran (1.0 M, 1.70 mL, 1.70 mmol, 1.20 equiv) was added dropwise via syringe to a solution of the phosphonium salt obtained in the preceding step (nominally 1.56 mmol, 1.10 equiv) in tetrahydrofuran (52 mL) at −78° C. The resulting heterogenous solution was stirred for 15 min at −78° C. A solution of the aldehyde 14 (384 mg, 1.42 mmol, 1.00 equiv) in tetrahydrofuran (19 mL) was then added dropwise via syringe over 10 min. Upon completion of the addition, the reaction mixture was stirred for 30 min at −78° C. The reaction vessel was then placed in an ice bath. The reaction mixture was stirred for 45 min at 0° C. The product mixture was diluted sequentially with saturated aqueous ammonium chloride solution (30 mL), water (10 mL), and ethyl acetate (70 mL). The layers that formed were separated, and the aqueous layer was extracted with ethyl acetate (50 mL). The organic layers were combined and the combined layers were washed with saturated aqueous sodium chloride solution (50 mL). The washed organic layer was dried over sodium sulfate. The dried solution was filtered and the filtrate was concentrated. The residue obtained was used directly in the next step.

Palladium on carbon (10 wt %, 330 mg, 310 μmol, 0.22 equiv) was added to a solution of the unpurified product obtained in the preceding step (nominally 1.42 mmol, 1.00 equiv) in methanol (25 mL) at 22° C. The reaction vessel was placed in a stainless steel hydrogenation apparatus. The apparatus was pressurized with dihydrogen (1,000 psi) at 22° C., sealed, and the reaction mixture was stirred for 24 h at 22° C. The apparatus was carefully vented. The product mixture was filtered through Celite and the Celite pad was rinsed with methanol (75 mL). The filtrates were combined and the combined filtrates were concentrated. The residue obtained was purified by automated flash-column chromatography (eluting with 15% ethyl acetate-hexanes initially, grading to 45% ethyl acetate-hexanes, linear gradient) to afford the bis (thiazole) 12 as a colorless oil (725 mg, 88%).

$R_f$=0.54 (75% ether-hexanes; UV). $^1$H NMR (500 MHz, $CDCl_3$): δ 8.05 (s, 1H, $H_6$), 6.85 (s, 1H, $H_3$), 5.40 (s, 1H, $H_8$), 5.05 (s, 2H, $H_2$), 4.71 (d, J=4.9 Hz, 2H, $H_7$), 3.44 (t, J=7.6 Hz, 2H, $H_4$), 3.23 (t, J=7.5 Hz, 2H, $H_5$), 1.48 (s, 18H, $H_1$), 1.47 (s, 9H, $H_9$). $^{13}$C NMR (126 MHz, $CDCl_3$): δ 189.9 (C), 170.4 (C), 168.2 (C), 155.7 (C), 154.1 (C), 152.0 (C), 151.7 (2×C), 125.7 (CH), 114.3 (CH), 83.2 (2×C), 79.69 (C), 49.0 ($CH_2$), 47.8 ($CH_2$), 32.8 ($CH_2$), 31.0 ($CH_2$), 28.4 ($3\times CH_3$), 28.0 ($6\times CH_3$). IR (ATR-FTIR), $cm^{-1}$: 3015 (m), 2995 (m), 2974 (m), 1696 (s), 1482 (m), 1424 (m), 1400 (m), 1367 (m) 1229 (m), 943 (s), 781 (m). HRMS-CI (m/z): $[M+Na]^+$ calcd for $C_{26}H_{38}N_4NaO_7S_2$, 605.2080; found, 605.2072.

Synthesis of the Diammonium Salt S23

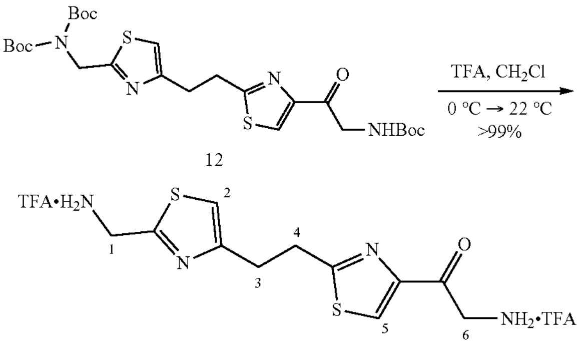

12

S23

Trifluoroacetic acid (500 μL, 6.53 mmol, 58.5 equiv) was added dropwise via syringe to a solution of the bis (thiazole) 12 (65.0 mg, 112 μmol, 1.00 equiv) in dichloromethane (2.0 mL) at 0° C. The reaction mixture was stirred at 0° C. before warming to 22° C. The reaction mixture was stirred for 3 h at 22° C. The product mixture was concentrated under a stream of nitrogen. The residue obtained was dissolved in dichloromethane (1.0 mL) and the resulting solution was concentrated again under a stream of nitrogen. This process was repeated twice. The residue S23 obtained was used immediately in the subsequent step.

$R_f$=Compound has no mobility on silica. $^1$H NMR (600 MHz, DMSO-$d_6$): δ 8.65 (s, 1H, $H_5$), 8.53 (s, 3H, $NH_3$), 8.29 (s, 3H, $NH_3$), 7.49 (s, 1H, $H_2$), 4.47 (s, 2H, $H_6$), 4.42 (s, 2H, $H_1$), 3.47 (t, J=7.6, 2H, $H_3$), 3.23 (t, J=7.6 Hz, 2H, $H_4$). $^{13}$C NMR (151 MHz, DMSO-$d_6$): δ 186.9 (C), 170.8 (C), 161.6 (C), 154.3 (C), 150.4 (C), 128.9 (CH), 117.0 (CH), 45.9 ($CH_2$), 40.1 ($CH_2$), 32.0 ($CH_2$), 30.3 ($CH_2$). IR (ATR-FTIR), $cm^{-1}$: 2922 (m), 1675 (s), 1522 (m), 1490 (m), 1428 (m), 1200 (s), 1137 (s), 1025 (m), 1003 (m), 836 (m), 789 (m), 722 (m), 707 (s). HRMS-CI (m/z): $[M+Na]^+$ calcd for $C_{11}H_{14}N_4NaOS_2$, 305.0507; found, 305.0516.

Synthesis of the Vinylagous Imide 10

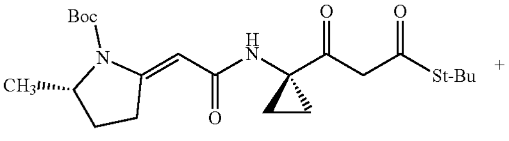

11

-continued

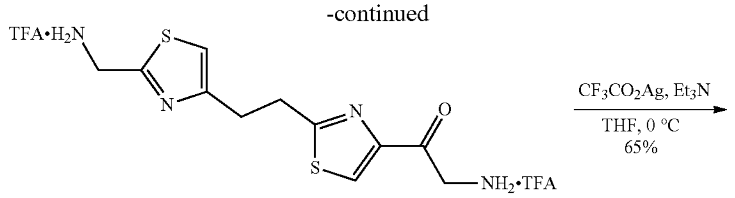

S23

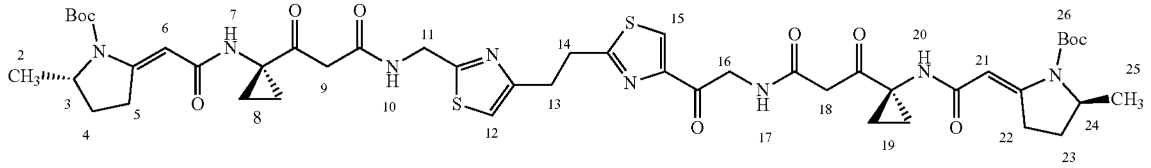

10

Triethylamine (258 μL, 1.86 mmol, 8.00 equiv) was added dropwise via syringe to a solution of the diammonium salt S23 (118 mg, 232 μmol, 1.00 equiv) and the β-ketothioester 11 (224 mg, 510 μmol, 2.20 equiv) in tetrahydrofuran (4.0 mL) at 0° C. Following completion of the addition the reaction vessel was wrapped in aluminum foil. A solution of silver trifluoroacetate (128 mg, 580 μmol, 2.50 equiv) in tetrahydrofuran (800 μL) was then added dropwise via syringe 3 min. The reaction mixture was stirred with protection from light for 30 min at 0° C. The product mixture was diluted sequentially with ethyl acetate (20 mL) and saturated aqueous ammonium chloride solution (10 mL). The resulting biphasic mixture was filtered through a pad of Celite and the Celite pad was rinsed with ethyl acetate (20 mL). The layers that formed were separated, and the aqueous layer was extracted with ethyl acetate (3× 20 mL). The organic layers were combined and the combined organic layers were washed with saturated aqueous sodium chloride solution (20 mL). The washed organic layer was dried over sodium sulfate. The dried solution was filtered and the filtrate was concentrated. The residue obtained was purified by automated flash-column chromatography (eluting with 100% dichloromethane initially, grading to 100% (9:1 ethyl acetate-methanol)-dichloromethane, linear gradient) to afford the vinylogous imide 10 as a white solid (148 mg, 151 μmol, 65%).

$R_f$=0.27 (5% methanol-dichloromethane, UV) $^1$H NMR (400 MHz, $CD_2Cl_2$): δ 8.09 (s, 1H, $H_{15}$), 7.97-7.93 (m, 1H, $H_{10}$ or $H_{17}$), 7.54-7.50 (m, 1H, $H_{10}$ or $H_{17}$), 6.85 (s, 1H, $H_{12}$), 6.69-6.60 (m, 2H, $H_7$ and $H_{20}$), 6.55 (s, 1H, $H_6$ or $H_{21}$), 6.53 (s, 1H, $H_6$ or $H_{21}$), 4.69 (m, 4H, $H_{11}$ and $H_{16}$), 4.23 (p, J=6.6 Hz, 2H, $H_3$ and $H_{24}$), 3.66 (s, 2H, $H_9$ or $H_{18}$), 3.65 (s, 2H, $H_9$ or $H_{18}$), 3.56-3.45 (m, 2H, $H_{5a}$ and $H_{22a}$), 3.44 (t, J=7.2 Hz, 2H, $H_{13}$), 3.21 (t, J=7.3 Hz, 2H, $H_{14}$), 2.92 (ddddd, J=17.6, 14.3, 11.1, 8.4, 2.2 Hz, 2H, $H_{5b}$ and $H_{22b}$), 2.01-1.89 (m, 2H, $H_{4a}$ and $H_{23a}$), 1.62-1.57 (m, 6H, $H_{4b}$, $H_{23b}$, and $H_{8a}$), 1.48 (s, 9H, $H_1$ or H26), 1.46 (s, 9H, $H_1$ or $H_{26}$),), 1.19 (d, J=2.7 Hz, 3H, $H_2$ or $H_{25}$), 1.18 (d, J=2.7 Hz, 3H, $H_2$ or $H_{25}$), 1.14 (p, J=3.8 Hz, 4H, $H_{8b}$). $^{13}$C NMR (126 MHz, $CD_2Cl_2$): δ 206.5 (C), 206.2 (C), 189.9 (C), 171.0 (C), 170.4 (C), 170.3 (C), 168.6 (C), 167.4 (C), 167.3 (C), 156.3 (C), 156.2 (C), 156.1 (C), 155.1 (C), 152.6 (C), 152.4 (C), 126.4 (CH), 115.1 (CH), 97.9 (CH), 97.7 (CH), 82.0 (C), 82.0 (C), 57.4 (CH), 57.3 (CH), 48.6 ($CH_2$), 46.6 ($CH_2$), 46.3 ($CH_2$) 41.8 (C), 41.7 (C), 41.7 ($CH_2$), 33.2 ($CH_2$), 31.6 ($CH_2$), 30.1 ($CH_2$) 30.0 ($CH_2$), 28.9 ($CH_2$), 28.9 ($CH_2$), 28.5 (3×$CH_3$), 28.5 (3×$CH_3$), 21.5 (2×$CH_2$), 21.4 (2×$CH_2$), 19.9 (2×$CH_3$). IR (ATR-FTIR), cm-1: (3292 (m), 2980 (m), 2970 (m), 2930 (w), 1702 (s), 1650 (s), 1604 (s), 1518 (s), 1153 (s), 1026 (m), 848 (m). HRMS-CI (m/z): $[M+Na]^+$ calcd for $C_{47}H_{62}N_8NaO_{11}S_2$, 1001.3877; found, 1001.3844.

Synthesis of the Bis(Iminium) Salt 9

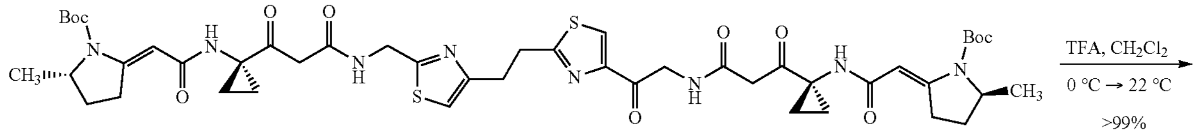

10

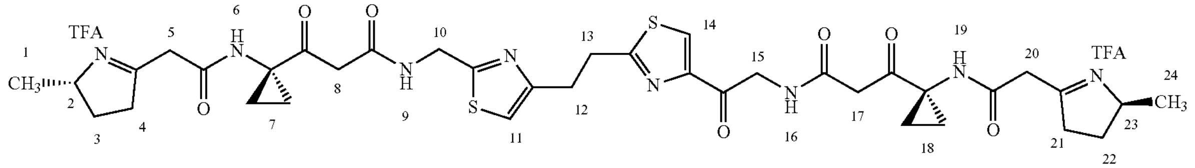

9

Trifluoroacetic acid (156 μL, 2.04 mmol, 200 equiv) was added to a solution of the vinylogous imide 10 (10.0 mg, 10.2 μmol, 1.00 equiv) in dichloromethane (200 μL) at 0° C. The reaction mixture was stirred for 5 min at 0° C. The cooling bath was removed, and the reaction mixture was allowed to warm to 22° C. over 15 min. The reaction mixture was stirred for 4 h at 22° C. The product mixture was concentrated under a stream of nitrogen to afford the bis (iminium) salt 9 as an orange oil (9.9 mg, >99%). The product so obtained was judged to be >95% pure ($^1$H NMR analysis) and was used without further purification.

$R_f$=Compound has no mobility on silica. $^1$H NMR (500 MHz, $CD_2Cl_2$): δ 8.62 (m, 3H, $H_6$, $H_9$, $H_{16}$, or $H_{19}$), 8.24 (m, 1H, $H_6$, $H_9$, $H_{16}$, or $H_{19}$), 8.16 (s, 1H, $H_{14}$), 7.30 (s, 1H, $H_{11}$), 4.97-4.87 (m, 2H, $H_{15}$), 4.67 (s, 2H, $H_{10}$), 4.61-4.51 (m, 2H, $H_2$ and $H_{23}$), 3.71 (s, 2H, $H_8$ or $H_{17}$), 3.68 (s, 2H, $H_8$ or $H_{17}$), 3.47 (m, 2H, $H_{12}$), 3.37 (m, 2H, $H_{13}$), 3.22 (m, 4H, $H_4$ and $H_{21}$), 2.55-2.49 (m, 2H, $H_{3a}$ and $H_{22a}$), 1.88 (m, 2H, $H_{3b}$ and $H_{22b}$), 1.58 (m, 2H, $H_{7a}$ or $H_{18a}$), 1.53 (m, 2H, $H_{7a}$ or $H_{18a}$), 1.46 (s, 6H, $H_1$ and $H_{24}$), 1.22 (s, 4H, $H_{7b}$ and $H_{18b}$). $^{13}$C NMR (126 MHz, $CD_2Cl_2$): δ 204.0 (C), 203.5 (C), 189.8 (2×C), 189.1 (C), 171.6 (C), 169.23 (C), 168.6 (C), 168.4 (C), 167.1 (C), 166.9 (C), 151.4 (C), 149.8 (C), 127.2 (CH), 117.9 (CH), 63.8 (2×CH), 47.8 ($CH_2$), 45.8 ($CH_2$), 45.4 ($CH_2$), 41.4 ($CH_2$), 41.3 ($CH_2$), 38.9 ($CH_2$), 38.0 ($CH_2$), 37.9 ($CH_2$), 37.3 (C), 37.2 (C), 31.6 ($CH_2$), 27.7 ($CH_2$), 27.5 (2×$CH_2$), 20.4 (2×$CH_2$), 20.2 (2×$CH_2$), 19.3 ($CH_3$), 19.2 ($CH_3$). IR (ATR-FTIR), $cm^{-1}$: 3234 (w), 2963 (w), 2866 (w), 1674 (s), 1382 (m), 1296 (m), 1265 (m), 1175 (m), 1126 (m), 1067 (m), 994 (m), 924 (w), 850 (m), 777 (m), 733 (m), 544 (m), 473 (w). HRMS-CI (m/z): $[M+Na]^+$ calcd for $C_{37}H_{46}N_8NaO_7S_2$ 801.2829; found, 801.2850.

Synthesis of Colibactin 742 (4)

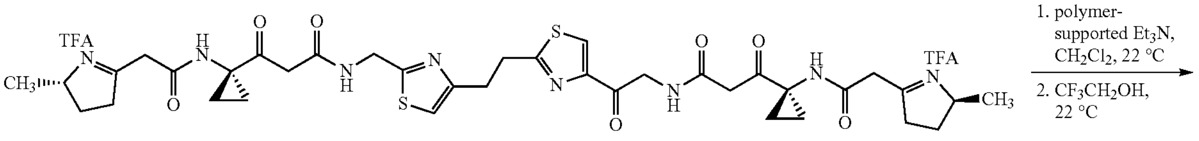

9

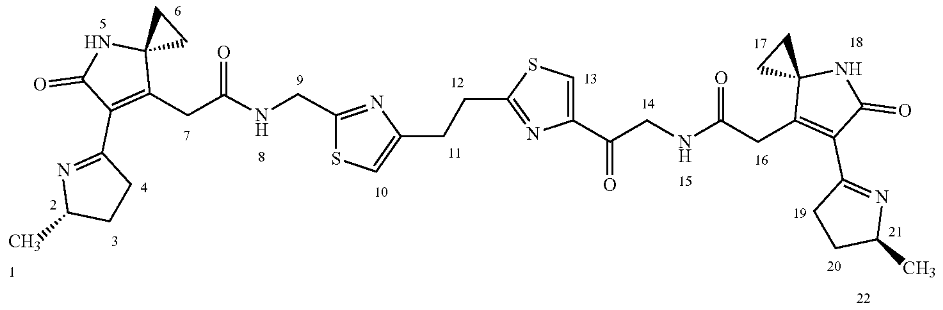

4a

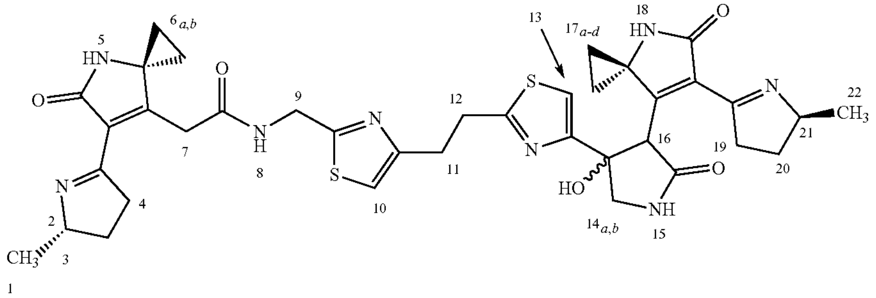

4b colibactin 742 (4) 4a/4b 1:8 mixture of isomers

Polymer supported triethylamine (102 mg, 102 μmol triethylamine, 10.0 equiv) was added to a solution of the unpurified bis (iminium) ion 9 (nominally 10.2 μmol, 1.00 equiv) in dichloromethane (1.00 mL) at 22° C. The heterogenous mixture was stirred for 10 min at 22° C. The reaction mixture was filtered through Celite and the Celite pad was rinsed with dichloromethane (3.0 mL). The filtrates were combined and the combined filtrates were concentrated. The residue obtained was dissolved in 2,2,2-trifluoroethanol (500 μL) at 22° C. and the resulting solution incubated at 22° C. for 10 min. The product mixture was concentrated to provide colibactin 742 (4) as a white solid (1:8 mixture of chain (4a) and ring (4b) isomers; 1.2:1 mixture of C41 diastereomers in 4b; 7.6 mg, >99%).

$R_f$=Compound has no mobility on silica. $^1$H NMR (600 MHz, $CD_2Cl_2$, C41 1,2-addition product diastereomers, minor diastereomer denoted by *) δ 10.74 (t, J=6.0 Hz, 1H, $H_8$ or $H_8$*), 10.70 (t, J=6.1 Hz, 1H, $H_8$ or $H_8$*), 7.75 (s, 1H, $H_{18}$), 7.71 (s, 1H, $H_{18}$*), 7.68 (s, 2H, H5), 7.26 (s, 1H, $H_{13}$*), 7.24 (s, 1H, $H_{13}$), 6.80 (s, 1H, $H_{10}$), 6.80 (s, 1H, $H_{10}$*), 6.66 (s, 1H, $H_{15}$), 6.65 (s, 1H, $H_{15}$*), 4.69-4.52 (m, 7H, $H_9$, $H_9$*), 4.22-4.13 (m, 4H, $H_2$, $H_2$*, and either $H_{21}$ or $H_{21}$*), 4.05 (d, J=10.3 Hz, 1H, $H_{14a}$), 4.00 (d, J=10.2 Hz, 1H, $H_{14a}$*), 3.96 (q, J=7.4 Hz, 1H, $H_{21}$ or $H_{21}$*) 3.56 (s, 1H, $H_{16}$*), 3.53 (s, 1H, $H_{16}$), 3.49-3.11 (m, 29H, $H_{4a}$, $H_{4a}$*, $H_{19a}$, $H_{19a}$*, $H_7$, $H_7$*, $H_{14b}$, $H_{14}$*, $H_1$, $H_{11}$*, $H_{12}$, $H_{12}$*), 3.03-2.87 (m, 3H, $H_4$, $H_{4b}$*), 2.69 (dddd, J=17.3, 9.7, 4.6, 2.2 Hz, 1H, $H_{19b}$ or $H_{19b}$*), 2.50 (dtd, J=18.0, 9.2, 2.3 Hz, 1H, $H_{19b}$ or $H_{19b}$*), 2.22-2.11 (m, 6H, $H_{3a}$, $H_{3a}$*, $H_{20a}$, $H_{20a}$*), 1.91-1.76 (m, 9H, $H_{6a}$, $H_{6a}$*), 1.51-1.39 (m, 13H, $H_{3b}$, $H_{3b}$*, $H_{20b}$, $H_{20b}$*, $H_{6b}$, $H_{6b}$*), 1.31 (d, J=6.7 Hz, 3H, $H_2$, or $H_2$*, or $H_{22}$, or $H_{22}$*), 1.28 (d, J=6.8 Hz, 3H, $H_2$, or $H_2$*, or $H_{22}$, or $H_{22}$*), 1.26 (d, J=6.9 Hz, 3H, $H_2$, or $H_2$*, or $H_{22}$, or $H_{22}$*), 1.22 (d, J=6.7 Hz, 3H, $H_2$, or $H_2$*, or $H_{22}$, or $H_{22}$*), 1.20-1.14 (m, 2H, $H_{17a}$ and $H_{17a}$*), 1.12-1.07 (m, 2H, $H_{17b}$ and $H_{17b}$*), 0.78-0.67 (m, 2H, $H_{17c}$ and $H_{17c}$*), −0.38-−0.47 (m, 2H, $H_{17d}$ and $H_{17d}$*).

$^1$H NMR (600 MHz, $CD_2Cl_2$, C41 ketone) δ 10.66 (t, J=5.9 Hz, 1H, $H_8$), 10.25 (t, J=5.1 Hz, 1H, $H_{15}$), 8.03 (s, 1H, $H_{13}$), 7.44 (s, 1H, $H_{18}$), 7.38 (s, 1H, $H_5$), 6.83 (s, 1H, $H_{10}$), 4.69-4.52 (overlap, m, 4H, $H_9$ and $H_{14}$), 4.32-4.27 (m, 1H, $H_2$ or $H_{21}$), 4.22-4.13 (overlap, 1H, $H_2$ or $H_{21}$), 3.49-3.11 (overlap, 10H, $H_1$, $H_{12}$, $H_{4a}$, $H_{19a}$, $H_7$, $H_{16}$), 3.03-2.87 (overlap, 2H, $H_{4b}$, $H_{19b}$), 2.22-2.11 (overlap, $H_{3a}$, $H_{20a}$), 1.91-1.76 (overlap, $H_{6a}$, $H_{17a}$), 1.51-1.39 (overlap, $H_{6b}$, $H_{17b}$, $H_{3b}$, $H_{20b}$), 1.37 (d, J=6.8 Hz, 1H, $H_1$ or $H_{22}$), 1.25-1.23 (overlap, 6H, $H_1$ or $H_{22}$).

$^{13}$C NMR (151 MHz, $CD_2Cl_2$) δ 189.9 (C), 173.3 (C), 172.9 (C), 171.9 (C), 171.7 (C), 171.7 (C), 171.7 (C), 171.4 (C), 171.0 (C), 171.0 (C), 169.7 (C), 169.7 (C), 169.4 (C), 169.4 (C), 169.0 (C), 168.9 (C), 168.9 (C), 168.8 (C), 159.3 (C), 159.3 (C), 159.1 (C), 159.0 (C), 158.9 (C), 157.3 (C), 156.4 (C), 155.4 (C), 155.4 (C), 155.3 (C), 152.9 (C), 132.4 (C), 132.3 (C), 128.5 (C), 128.3 (C), 128.2 (C), 127.9 (C), 127.8 (C), 126.0 (CH), 116.1 (2×CH), 114.9 (CH), 114.7 (CH), 114.6 (CH), 81.1, 81.0, 67.9 (CH), 67.7 (2×CH), 67.7 (CH), 67.7 (CH), 66.1 (C), 57.7 ($CH_2$), 57.7 ($CH_2$), 51.7 (2×CH), 48.8 ($CH_2$), 47.0 (C), 46.9 (C), 46.5 (C), 46.5 (C), 46.4 (C), 46.3 (C), 41.5 (C), 41.5 (C), 37.5 (2×$CH_2$), 37.5 ($CH_2$), 37.4 ($CH_2$), 37.2 ($CH_2$), 36.6 ($CH_2$), 35.4 (3×$CH_2$), 35.3 ($CH_2$), 35.3 ($CH_2$), 33.2 ($CH_2$), 32.8 ($CH_2$), 32.8 ($CH_2$), 31.7 ($CH_2$), 31.6 ($CH_2$), 31.3 ($CH_2$), 31.2 ($CH_2$), 30.9 ($CH_2$), 30.8 ($CH_2$), 30.8 ($CH_2$), 22.5 (CH), 22.4 (CH), 21.9 (CH), 21.6 (CH), 13.2 ($CH_2$), 13.1 ($CH_2$), 13.0 ($CH_2$), 13.0 ($CH_2$), 13.0 ($CH_2$), 13.0 ($CH_2$), 12.8 ($CH_2$), 11.1 ($CH_2$), 11.0 ($CH_2$). IR (ATR-FTIR), $cm^{-1}$: 3207 (w), 2982 (w), 2343 (w), 1676 (s), 1428 (m), 1335 (m), 1265 (m), 1174 (w), 1123 (m), 994 (m), 959 (m), 926 (w), 849 (m), 775 (m), 732 (m), 638 W), 549 (w), 472 (w). HRMS-CI (m/z): $[M+Na]^+$ calcd for $C_{37}H_{42}N_8NaO_5S_2$ 765.2617; found, 765.2633.

Synthesis of the Vinylogous Imide S12

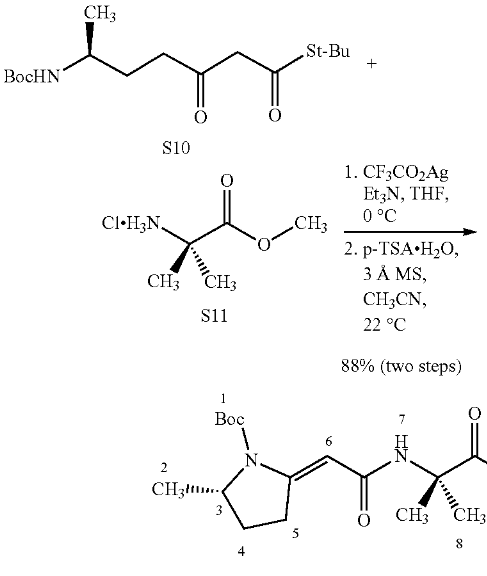

S10
S11
S12

Triethylamine (367 μL, 2.64 mmol, 4.00 equiv) was added to a solution of 2-amino-2-methylpropanoic acid methyl ester hydrochloride S11 (152 mg, 989 μmol, 1.50 equiv) and the thioester S10 (200 mg, 659 μmol, 1.00 equiv) in tetrahydrofuran (3.0 mL) at 0° C. A solution of silver trifluoroacetate (291 mg, 1.32 mmol, 2.00 equiv) in tetrahydrofuran (2.0 mL) was then added dropwise via syringe over 5 min. The reaction mixture was stirred for 20 min at 0° C. The product mixture was filtered through a pad of Celite, and the Celite pad was rinsed with ethyl acetate (30 mL). The filtrates were combined and the combined filtrates were concentrated. The residue obtained was dissolved in ethyl acetate (20 mL). The resulting solution was washed sequentially with saturated aqueous ammonium chloride solution (2× 20 mL) and saturated aqueous sodium chloride solution (20 mL). The washed organic layer was dried over sodium sulfate. The dried solution was filtered and the filtrate was concentrated. The residue obtained was used directly in the next step.

A solution of p-toluenesulfonic acid monohydrate (227 mg, 1.32 mmol, 2.00 equiv) and the residue obtained in the preceding step (nominally 659 μmol; dried by azeotropic distillation from benzene (3×5 mL)) in acetonitrile (20 mL) was added dropwise via syringe to a round-bottomed flask containing activated powdered 3 Å molecular sieves (2.00 g) at 22° C. The resulting mixture was stirred for 30 min at 22° C. The product mixture was filtered through a pad of Celite, and the Celite pad was rinsed with ethyl acetate (30 mL). The filtrates were combined and the combined filtrates were concentrated. The residue obtained was dissolved in ethyl acetate (30 mL). The resulting solution was washed sequentially with saturated aqueous sodium bicarbonate solution (20 mL) and saturated aqueous sodium chloride solution (20 mL). The washed organic layer was dried over sodium sulfate. The dried solution was filtered and the filtrate concentrated. The residue obtained was purified by automated flash-chromatography (eluting with 5% ethyl acetate-hexanes initially, grading to 70% ethyl acetate-hexanes, linear gradient) to afford the vinylagous imide S12 as white solid (197 mg, 88%).

$R_f$=0.37 (40% ethyl acetate-hexanes; UV) $^1$H NMR (600 MHz, $CDCl_3$): δ 6.48 (s, 1H, $H_6$), 5.77 (s, 1H, $H_7$), 4.24-4.16 (m, 1H, $H_3$), 3.69 (s, 3H, $H_9$), 3.48 (ddt, J=18.1, 8.9, 1.6 Hz, 1H, $H_{5a}$), 2.90 (dddd, J=18.1, 11.7, 8.4, 2.4 Hz, 1H, $H_{5b}$), 1.91 (tt, J=12.1, 8.5 Hz, 1H, $H_{4a}$), 1.60-1.52 (m, 1H, $H_{4b}$), 1.49 (s, 15H, $H_1$ and $H_8$), 1.16 (d, J=6.3 Hz, 3H, $H_2$). $^{13}$C NMR (151 MHz, $CDCl_3$): δ 175.4 (C), 167.7 (C), 154.2 (C), 152.2 (C), 98.8 (CH), 81.5 (C), 56.6 (CH), 56.0 (C), 52.5 ($CH_3$), 29.2 ($CH_2$), 28.5 ($CH_2$), 28.3 (3×$CH_3$), 25.4 (2×$CH_3$), 19.7 ($CH_3$). IR (ATR-FTIR), $cm^{-1}$: 3370 (w), 2978 m), 1715 (s), 1655 (m), 1610 (s), 1518 (s), 1382 (s), 1240 (m), 1141 (s), 1048 (m), 851 (s), 773 (m), 771 (m), 552 (m), 522 (w), 429 (w). HRMS-CI (m/z): $[M+Na]^+$ calcd for $C_{17}H_{28}N_2NaO_5$ 363.1896; found, 363.1907.

Synthesis of the β-Ketothioester S13

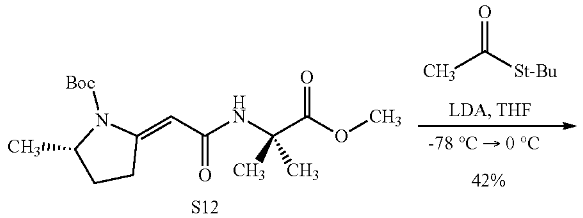

S12

-continued

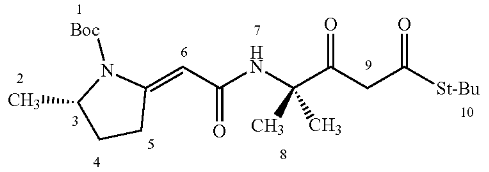

S13

A solution of n-butyllithium in hexanes (2.40 M, 1.47 mL, 3.53 mmol, 12.0 equiv) was added dropwise via syringe to a solution of di-iso-propylamine (498 μL, 3.53 mmol, 12.0 equiv) in tetrahydrofuran (3.0 mL) at −78° C. The solution was stirred for 15 min at −78° C. tert-Butyl thioacetate (503 μL, 3.53 mmol, 12.0 equiv) was then added dropwise via syringe to this solution at −78° C. The resulting mixture was stirred for 15 min at −78° C. A solution of the ester S12 (100.0 mg, 294 μmol, 1.00 equiv) was then added dropwise via syringe at −78° C. The reaction vessel was then placed in an ice bath. The reaction mixture was stirred for 3 h at 0° C. The product mixture was diluted sequentially with a mixture of saturated aqueous ammonium chloride solution and water (1:1 v/v, 20 mL) and ethyl acetate (30 mL). The layers that formed were separated, and the organic layer was dried over sodium sulfate. The dried solution was filtered and the filtrate was concentrated. The residue obtained was purified by automated flash-column chromatography (eluting with hexanes initially, grading to 60% ethyl acetate-hexanes, linear gradient) to provide the β-ketothioester S13 as a colorless oil (53.4 mg, 42%).

$R_f$=0.68 (40% ethyl acetate-hexanes; UV) $^1$H NMR (600 MHz, $CDCl_3$): δ 6.50 (s, 1H, $H_6$), 5.70 (s, 1H, $H_7$), 4.26-4.20 (m, 1H, $H_3$), 3.71 (s, 2H, $H_9$), 3.50 (ddt, J=18.4, 8.8, 1.6 Hz, 1H, $H_{5a}$), 2.90 (dddd, J=18.3, 11.9, 8.4, 2.4 Hz, 1H, $H_{5b}$), 1.93 (tt, J=12.2, 8.6 Hz, 1H, $H_{4a}$), 1.61-1.56 (m, 1H, $H_{4b}$), 1.51 (s, 9H, $H_1$), 1.44 (s, 9H, $H_{10}$), 1.38 (s, 3H, $H_{8a}$), 1.37 (s, 3H, $H_{8b}$), 1.18 (d, J=6.3, 3H, $H_2$). $^{13}$C NMR (151 MHz, $CDCl_3$): δ 202.6 (C), 193.7 (C), 167.9 (C), 155.3 (C), 152.2 (C), 97.6 (CH), 81.8 (C), 61.1 (C), 56.8 (CH), 51.6 ($CH_2$), 48.7 (C), 29.8 (3×$CH_3$), 29.4 ($CH_2$), 28.5 ($CH_2$), 28.4 (3×$CH_3$), 24.1 ($CH_3$), 24.0 ($CH_3$), 19.7 ($CH_3$). IR (ATR-FTIR), $cm^{-1}$: 3367 (w), 2974 (m), 1716 (s), 1688 (m), 1605 (s), 1518 (m), 1457 (m), 1383 (s), 1243 (s), 1152 (s), 1025 (s), 988 (m), 849 (m), 771 (m), 733 (s), 701 (m), 658 (w), 534 (w), 494 (w). HRMS-CI (m/z): $[M+H]^+$ calcd for $C_{22}H_{37}N_2O_5S$, 441.2423; found, 441.2438.

Synthesis of the Vinylogous Imide S14

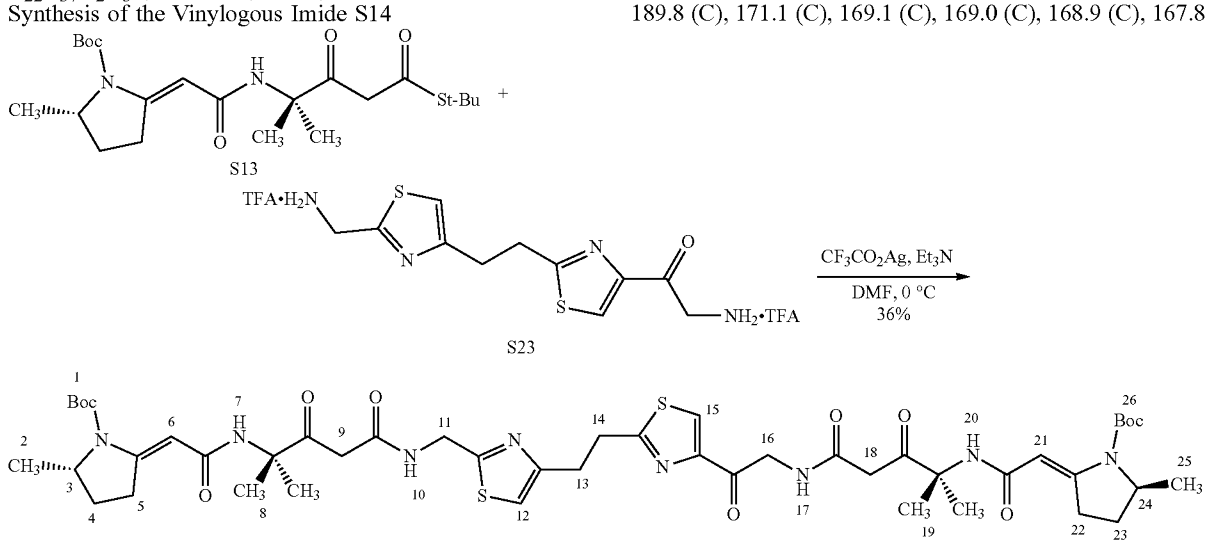

S13

S23

S14

Triethylamine (62.0 μL, 44.8 μmol, 8.00 equiv) was added dropwise via syringe to a solution of the bis (ammonium) salt S23 (nominally 56.0 μmol, 1.00 equiv) and the β-keto-thioester S13 (54.3 mg, 123 μmol, 2.20 equiv) in N,N-dimethylformamide (500 μL) at 0° C. The reaction vessel was immediately covered with aluminum foil. A solution of silver trifluoroacetate (30.9 mg, 140 μmol, 2.5 equiv) in N,N-dimethylformamide (400 μL) was then added dropwise via syringe over 3 min. The reaction mixture was stirred for 30 min at 0° C., with protection from light. The product mixture was diluted sequentially with ethyl acetate (10 mL) and saturated aqueous ammonium chloride solution (5.0 mL). The resulting biphasic mixture was filtered through a pad of Celite. The Celite pad was rinsed with ethyl acetate (10 mL). The filtrates were combined and the combined filtrates were transferred to a separatory funnel. The layers that formed were separated, and the aqueous layer was extracted with ethyl acetate (3× 10 mL). The organic layers were combined and the combined organic layers were washed with saturated aqueous sodium chloride solution (10 mL). The washed organic layer was dried over sodium sulfate. The dried solution was filtered and the filtrate was concentrated. The residue obtained was purified by automated flash-column chromatography (eluting with 100% dichloromethane initially, grading to 100% (9:1 ethyl acetate-methanol)-dichloromethane, linear gradient) to afford the vinylogous imide S14 as a white solid (20.0 mg, 36%).

$R_f$=0.59 (10% methanol-dichloromethane; UV). $^1$H NMR (600 MHz, $CD_2Cl_2$): δ 8.08 (s, 1H, $H_{15}$), 7.78 (t, J=6.0 Hz, 1H, $H_{10}$), 7.65 (t, J=4.9 Hz, 1H, $H_{17}$), 6.88 (s, 1H, $H_{12}$), 6.55 (s, 2H, $H_6$, $H_{21}$), 6.03 (s, 1H, $H_7$ or $H_{20}$), 5.98 (s, 1H, $H_7$ or $H_{20}$), 4.75 (d, J=5.0 Hz, 2H, $H_{16}$), 4.68 (s, J=6.0 Hz, 2H, $H_{11}$), 4.23 (m, 2H, $H_3$ and $H_{24}$), 3.54-3.49 (m, 1H, $H_{5a}$ or $H_{22a}$), 3.53 (d, J=1.1 Hz, 2H, $H_9$ or $H_{18}$), 3.51 (s, 2H, $H_9$ or $H_{18}$), 3.45 (t, J=7.5 Hz, 2H, $H_{13}$), 3.38 (ddt, J=18.2, 8.8, 1.6 Hz, 1H, $H_{5a}$ or $H_{22a}$), 3.24 (t, J=7.5 Hz, 2H, $H_{14}$), 2.94 (dddd, J=18.3, 11.9, 8.4, 2.3 Hz, 1H, $H_{5b}$ or $H_{22b}$), 2.80 (dddd, J=18.2, 11.7, 8.4, 2.3 Hz, 1H, $H_{5b}$ or $H_{22b}$), 1.92 (dtt, J=36.0, 12.1, 8.6 Hz, 2H, $H_{4a}$, $H_{23a}$), 1.63-1.55 (m, 2H, $H_{4b}$, $H_{23b}$), 1.50 (s, 9H, $H_1$ or $H_{26}$), 1.50 (s, 9H, $H_1$ or $H_{26}$), 1.34 (d, J=2.7 Hz, 6H, $H_{8a}$, $H_{19a}$), 1.33 (s, 6H, $H_{8b}$, $H_{19b}$), 1.20 (d, J=6.4 Hz, 3H, $H_2$ or $H_{25}$), 1.16 (d, J=6.4 Hz, 3H, $H_2$ or $H_{25}$). $^{13}$C NMR (151 MHz, $CD_2Cl_2$): δ 206.4 (C), 206.2 (C), 189.8 (C), 171.1 (C), 169.1 (C), 169.0 (C), 168.9 (C), 167.8

(C), 167.6 (C), 156.7 (2×C), 155.2 (C), 152.8 (C), 152.5 (C), 152.4 (C), 126.1 (CH), 115.1 (CH), 97.2 (CH), 97.1 (CH), 82.2 (C), 82.1 (C), 61.2 (C), 61.2 (C), 57.4 (CH), 57.4 (CH), 48.7 ($CH_2$), 43.3 ($CH_2$), 43.3 ($CH_2$), 41.7 ($CH_2$), 33.3 ($CH_2$), 31.6 ($CH_2$), 30.0 ($CH_2$), 30.0 ($CH_2$), 28.9 ($CH_2$), 28.8 ($CH_2$), 28.5 (3×$CH_3$), 28.5 (3×$CH_3$), 24.3 ($CH_3$), 24.3 ($CH_3$), 24.2 ($CH_3$), 24.2 ($CH_3$), 19.9 (2×$CH_3$). IR (ATR-FTIR), $cm^{-1}$: 3306 (w), 2975 (m), 2289 (w), 1711 (s), 1659 (s), 1597 (s), 1524 (s), 1364 (s), 1346 (s), 1244 (s) 1026 (m), 849 (m). HRMS-CI (m/z): $[M+Na]^+$ calcd for $C_{47}H_{66}N_8NaO_{11}S_2$ 1005.4190; found, 1005.4157.

Synthesis of the Bis(Iminium) Salt S15

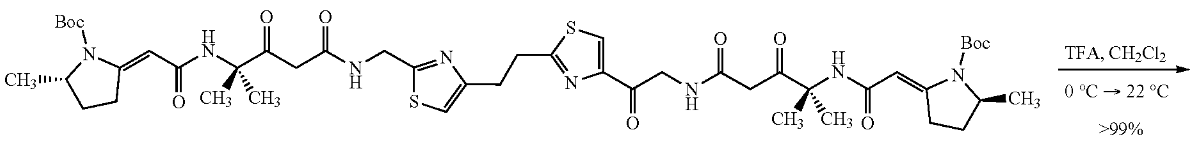

S14

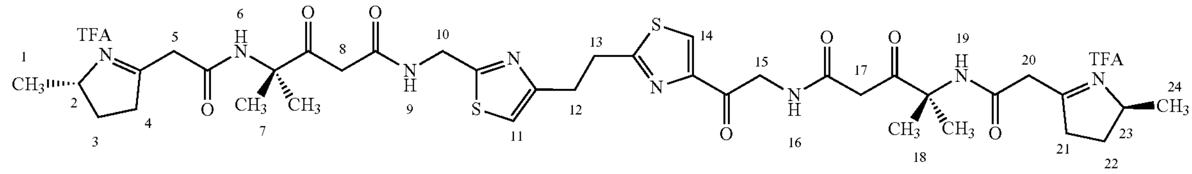

S15

Trifluoroacetic acid (308 μL, 4.03 mmol, 200 equiv) was added to a solution the vinylogous imide S14 (19.8 mg, 20.1 μmol, 1.00 equiv) in dichloromethane (2.0 mL) at 0° C. The reaction mixture was stirred for 5 min at 0° C. The reaction vessel was removed from the cooling bath. The reaction mixture was stirred for 1 h at 22° C. The product mixture was concentrated under a stream of nitrogen to provide the bis (iminium) salt S15 as an orange oil (19.7 mg, >99%). The bis (iminium) salt S15 obtained in this way was judged to be >95% pure ($^1$H NMR analysis) and was used without further purification.

$R_f$=Compound has no mobility on silica. $^1$H NMR (600 MHz, $CD_2Cl_2$) δ 9.43 (s, 1H, $H_9$), 8.75 (s, 1H, $H_{16}$), 8.08 (s, 1H, $H_{14}$), 7.34 (s, 1H, $H_6$ or $H_{19}$), 7.16 (s, 1H, $H_6$ or $H_{19}$), 7.03 (s, 1H, $H_{11}$), 4.79 (d, J=5.7 Hz, 2H, $H_{10}$), 4.71 (d, J=5.1 Hz, 2H, $H_{15}$), 4.62-4.57 (m, 2H, $H_2$, $H_{23}$), 3.96-3.79 (m, 4H, $H_8$, $H_{17}$), 3.76-3.62 (m, 2H, $H_{4a}$, $H_{21a}$), 3.60-3.48 (m, 2H, $H_{4b}$, $H_{21b}$), 3.43 (t, J=7.2 Hz, 2H, $H_{12}$), 3.29 (t, J=7.3 Hz, 2H, $H_{13}$), 2.66-2.57 (m, 2H, $H_{3a}$, $H_{22a}$), 2.02-1.91 (m, 2H, $H_{3b}$, $H_{22b}$), 1.51 (s, 12H, $H_1$, $H_{24}$ and either $H_7$ or $H_{18}$), 1.40 (s, 6H, $H_7$ or $H_{18}$). $^{13}$C NMR spectra could not be obtained as the compound cyclized to 22 on the on the $^{13}$C NMR timescale. IR (ATR-FTIR), $cm^{-1}$: 2933 (w), 2110 (w), 1697 (s), 1541 (m), 1450 (m), 1366 (m), 1259 (m), 1170 (s), 1136 (s), 797 (m), 750 (m), 719 (m), 705 (m), 477 (w). HRMS-CI (m/z): $[M+Na]^+$ calcd for $C_{37}H_{46}N_8NaO_5S_2$ 769.2930; found, 769.2945, the cyclized product mass of S22.

Synthesis of the Gem-Dimethyl Colibactin Derivative 22

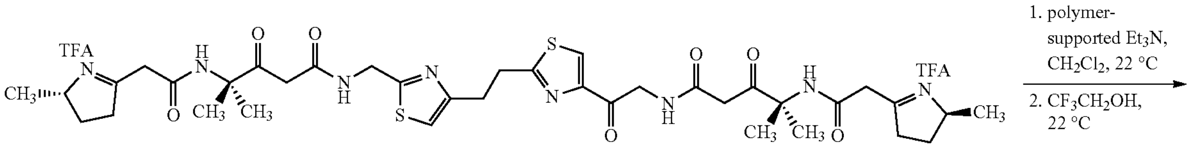

S15

-continued

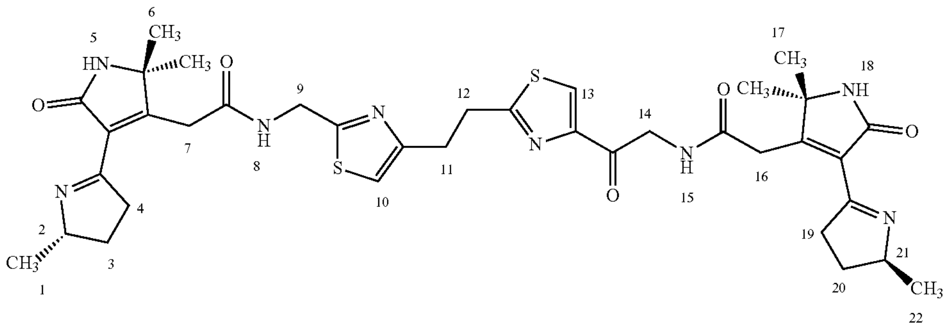

22

Polymer-supported triethylamine (201 mg, 201 μmol triethylamine, 10.0 equiv) was added to a solution of S15 (nominally 20.1 μmol, 1.00 equiv) in dichloromethane (2.0 mL) at 22° C. The resulting heterogenous mixture was stirred for 10 min at 22° C. The product mixture was filtered through a pad of Celite. The Celite pad was a washed with dichloromethane (3×2.0 mL) and the filtrates were combined and concentrated. The residue obtained was dissolved in 2,2,2-trifluoroethanol (1.0 mL) at 22° C. and the resulting solution incubated at 22° C. for 10 min. The product mixture was concentrated to provide the gem-dimethyl colibactin derivative 22 as a white solid (15.0 mg, >99%). The gem-dimethyl colibactin derivative 22 obtained in this way judged to be >95% purity ($^1$H NMR analysis) and was used without further purification.

$R_f$=Compound has no mobility on silica. $^1$H NMR (600 MHz, $CD_2Cl_2$) δ 9.44 (m, 1H, $H_{15}$), 8.75 (m, 1H, $H_8$), 8.08 (s, 1H, $H_{13}$), 7.34 (s, 1H, $H_5$), 7.16 (s, 1H, $H_{18}$), 7.03 (s, 1H, $H_{10}$), 4.79 (d, J=5.7 Hz, 2H, $H_{14}$), 4.71 (d, J=5.1 Hz, 2H, $H_9$), 4.61-4.58 (m, 2H, $H_2$, $H_{21}$), 3.95-3.80 (m, 4H, $H_7$, $H_{16}$), 3.76-3.62 (m, 2H, $H_{4a}$, $H_{19a}$), 3.54 (m, 2H, $H_{4b}$, $H_{19b}$), 3.43 (t, J=7.2 Hz, 2H, $H_{11}$), 3.29 (t, J=7.3 Hz, 2H, $H_{12}$), 2.64-2.57 (m, 2H, $H_{3a}$, $H_{20a}$), 2.01-1.92 (m, 2H, $H_{3b}$, $H_{20b}$), 1.51 (s, 12H, $H_6$, $H_{17}$), 1.40 (s, 6H, $H_1$, $H_{22}$). $^{13}$C NMR (151 MHz, $CD_2Cl_2$) δ 188.5 (C), 180.1 (C), 179.9 (C), 176.5 (2×C), 170.5 (2×C), 168.6 (2×C), 168.4 (2×C), 153.5 (C), 152.28 (C), 131.6 (2×C), 126.8 (CH), 116.6 (CH), 64.8 (C), 64.7 (C), 63.2 (CH), 63.1 (CH), 49.0 ($CH_2$), 41.1 ($CH_2$) 36.0 ($CH_2$), 35.9 ($CH_2$), 34.7 (2×$CH_2$), 32.7 ($CH_2$), 30.2 ($CH_2$), 28.6 ($CH_2$), 28.5 ($CH_2$), 24.5 (2×$CH_3$), 24.3 (2×$CH_3$), 20.4 (2×$CH_3$). IR (ATR-FTIR), $cm^{-1}$: 2963 (w), 1675 (s), 1478 (w), 1427 (m), 1335 (m), 1265 (m), 1172 (m), 1123 (m), 1057 (m), 944 (m), 925 (m), 849 (m), 774 (m), 732 (s), 700 (m), 623 (m), 540 (m), 469 (w). HRMS-CI (m/z): $[M+Na]^+$ calcd for $C_{37}H_{46}N_8NaO_5S_2$ 769.2930; found, 769.2945.

Synthesis of the Vinylogous Imide S17

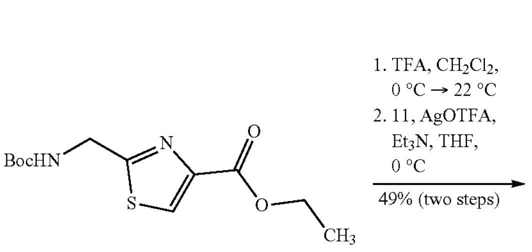

S16

-continued

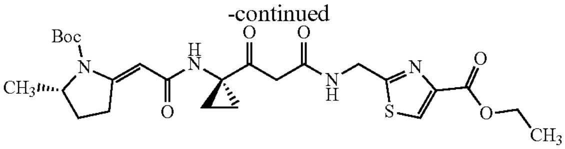

S17

Trifluoroacetic acid (1.90 mL, 25.4 mmol, 200 equiv) was added to a solution of the thiazole S16 (36.4 mg, 127 μmol, 1.00 equiv) in dichloromethane (1.3 mL) at 0° C. The reaction mixture was stirred for 5 min at 0° C. The cooling bath was removed and the reaction mixture was allowed to warm to 22° C. over 10 min. The warmed reaction mixture was stirred for 1 h at 22° C. The product mixture was concentrated under a stream of nitrogen and the residue obtained was employed directly in the following step.

Triethylamine (47.0 μL, 338 μmol, 4.00 equiv) was added dropwise via syringe to a solution of the unpurified product obtained in the preceding step (nominally 127 μmol, 1.50 equiv) and the β-ketothioester 11 (37.0 mg, 84.4 μmol, 1.00 equiv) in tetrahydrofuran (1.5 mL) at 0° C. Upon completion of the addition the reaction vessel was wrapped with aluminum foil. A solution of silver trifluoroacetate (37.3 mg, 169 μmol, 2.00 equiv) in tetrahydrofuran (500 μL) was then added dropwise via syringe over 3 min. The reaction mixture was stirred for 30 min at 0° C., with protection from light. The product mixture was diluted sequentially with ethyl acetate (10 mL) and saturated aqueous ammonium chloride solution (5.0 mL). The resulting biphasic mixture was filtered through Celite and the Celite pad was rinsed with ethyl acetate (10 mL). The filtrates were combined and the combined filtrates were transferred to a separatory funnel. The layers that formed were separated, and the aqueous layer was extracted with ethyl acetate (3× 10 mL). The organic layers were combined and the combined organic layers were washed with saturated aqueous sodium chloride solution (10 mL). The washed organic layer was dried over sodium sulfate. The dried solution was filtered and the filtrate was concentrated. The residue obtained was purified by automated flash-column chromatography (eluting with 100% dichloromethane initially, grading to 100% (9:1 ethyl acetate-methanol) dichloromethane, linear gradient) to afford the vinylogous imide S17 as a white solid (22.0 mg, 49%).

NMR spectroscopic data for S17 obtained in this way were in agreement with those previously reported (Wilson, M. R. et al., *Science* 2019, 363,).

Synthesis of the Iminium Ion S18

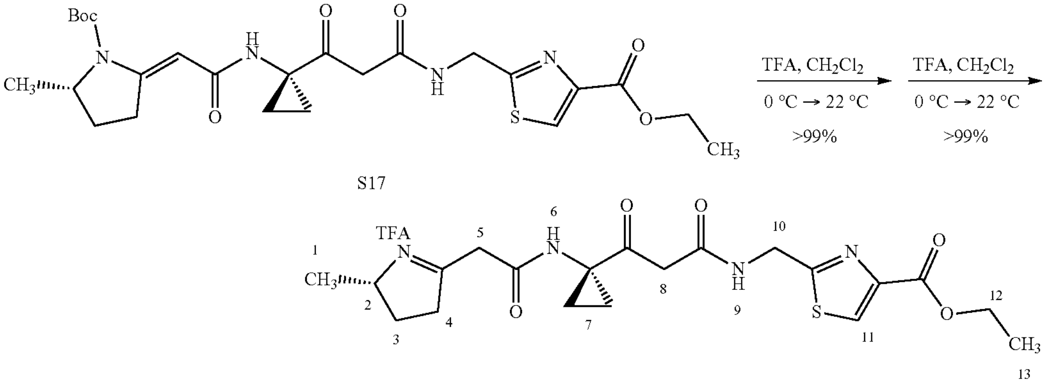

S17

S18

Trifluoroacetic acid (500 μL, 6.53 mmol, 233 equiv) was added to a solution of the vinylogous imide S17 (15.0 mg, 28.1 μmol, 1.00 equiv) in dichloromethane (250 μL) at 0° C. The reaction mixture was stirred for 5 min at 0° C. The cooling bath was then removed and the reaction mixture was allowed to warm to 22° C. over 10 min. The reaction mixture was stirred for 4 h at 22° C. The product mixture was concentrated under a stream of nitrogen to provide the iminium ion S18 as an orange oil (14.9 mg, >99%). The iminium ion S18 obtained in this way judged to be >95% purity ($^1H$ NMR analysis) and was used without further purification.

$R_f$=Compound has no mobility on silica. $^1H$ NMR (600 MHz, $CD_2Cl_2$) δ 9.26 (s, 1H, $H_6$), 8.87 (s, 1H, $H_9$), 8.15 (s, 1H, $H_{11}$), 4.82-4.72 (m, 4H, $H_5$ and $H_{10}$), 4.60-4.53 (m, 1H, $H_2$), 4.34 (q, J=7.0 Hz, 2H, $H_{12}$), 3.61-3.52 (m, 2H, $H_8$), 3.22-3.13 (m, 2H, $H_4$), 2.51 (ddt, J=13.7, 8.8, 5.1 Hz, 1H, $H_{3a}$), 1.88 (ddt, J=13.5, 9.3, 6.9 Hz, 1H, $H_{3b}$), 1.56-1.50 (m, 2H, $H_{7a}$), 1.48 (d, J=6.5 Hz, 3H, $H_1$), 1.36 (t, J=7.0 Hz, 3H, $H_{13}$), 1.13 (m, 2H, $H_{7b}$). $^{13}C$ NMR (151 MHz, $CD_2Cl_2$) δ 203.8 (C), 190.0 (C), 170.1 (C), 168.1 (C), 167.7 (C), 162.0 (C), 146.4 (C), 128.6 (CH), 64.2 (CH), 62.2 ($CH_2$), 48.8 ($CH_2$), 41.7 ($CH_2$), 41.1 ($CH_2$), 38.9 ($CH_2$), 37.9 (C), 28.5 ($CH_2$), 20.8 ($CH_2$), 20.7 ($CH_2$), 20.1 ($CH_3$), 14.6 ($CH_3$). IR (ATR-FTIR), $cm^{-1}$: 3271 (w), 2980 (w), 1666 (s), 1548 (s), 1420 (m), 1335 (m), 1180 (s), 1136 (s), 1100 (s), 1022 (m), 798 (m), 759 (m), 721 (m), 616 (w). HRMS-CI (m/z): $[M+Na]^+$ calcd for $C_{20}H_{26}N_4NaO_5S$, 457.1522; found, 457.1533.

Synthesis of the Electrophile 23

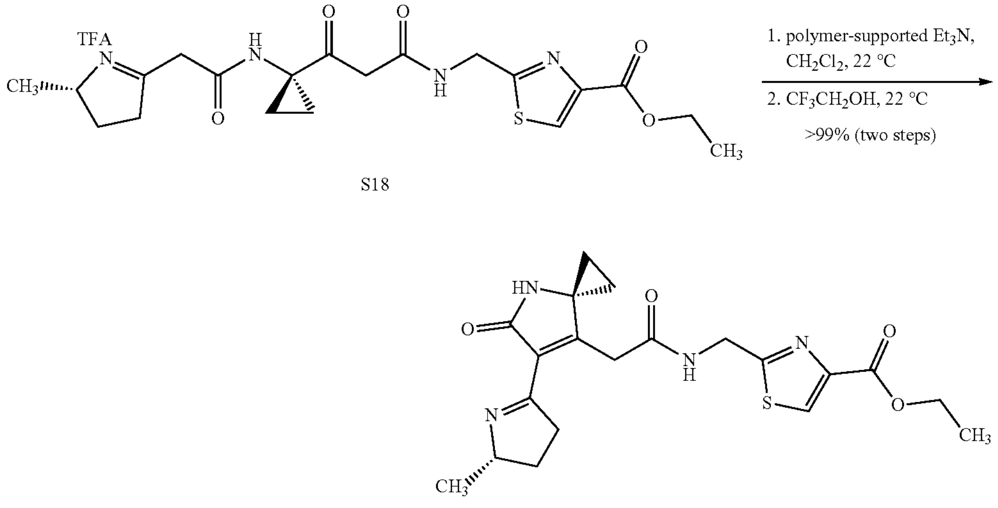

S18

23

Polymer-supported triethylamine (281 mg, 281 μmol triethylamine, 10.0 equiv) was added to a solution of S18 (nominally 28.1 μmol, 1.00 equiv) in dichloromethane (2.0 mL) at 22° C. The heterogenous mixture was stirred for 10 min at 22° C. The product mixture was filtered through a pad of Celite. The Celite pad was washed with ethyl acetate (3×5.0 mL). The filtrates were combined and the combined filtrates were concentrated. The residue obtained was dissolved in 2,2,2-trifluoroethanol (1.00 mL) at 22° C. and the resulting solution was incubated at 22° C. for 10 min. The product mixture was concentrated to provide the electrophile 23 as a white solid (11.7 mg, >99%).

NMR spectroscopic data for 23 obtained in this way were in agreement with those previously reported (Wilson, M. R. et al., *Science* 2019, 363).

Synthesis of the α-Azido Ketone S21

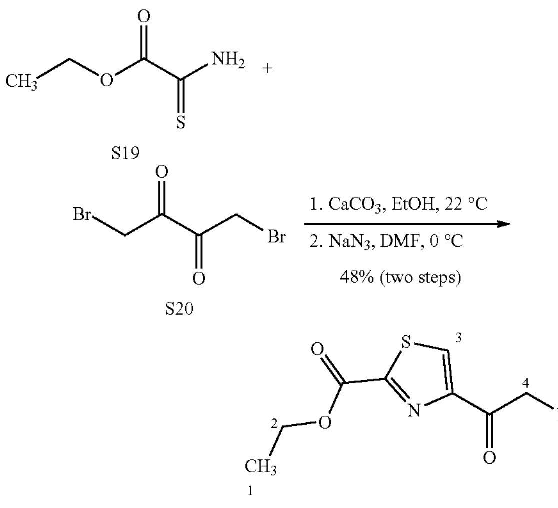

S19 S20 S21

Calcium carbonate (620 mg, 6.19 mmol, 3.30 equiv) was added to a solution of ethyl 2-amino-2-thioxoacetate (S19) (250 mg, 1.88 mmol, 1.00 equiv) and 1,4-dibromobutane-2,3-dione (S20) (1.37 g, 5.63 mmol, 3.00 equiv) in ethanol (9.4 mL) at 22° C. The reaction mixture was stirred for 14 h at 22° C. The product mixture was diluted with ethyl acetate (15 mL) and the diluted product mixture was filtered through a pad of Celite. The Celite pad was rinsed with ethyl acetate (30 mL). The filtrates were combined and the combined filtrates were concentrated. The residue obtained was used directly in the following step.

Sodium azide (859 mg, 13.2 mmol, 7.00 equiv) was added to a solution of the unpurified product obtained the preceding step (nominally 1.88 mmol, 1.00 equiv) in N,N-dimethylformamide (6.3 mL) at 0° C. The reaction mixture was stirred for 30 min at 0° C. The product mixture was diluted with ethyl acetate (50 mL). The diluted solution was washed sequentially with water (5×25 mL) and saturated aqueous sodium chloride solution (20 mL). The washed organic layer was dried over sodium sulfate. The dried solution was filtered and the filtrate was concentrated. The residue obtained was purified by automated flash-column chromatography (eluting with hexanes initially, grading to 70% ethyl acetate-hexanes, linear gradient) to afford the α-azidoketone S21 as a yellow oil (215 mg, 48% over three steps).

$R_f$=0.28 (30% ethyl acetate-hexanes; UV). $^1$H NMR (500 MHz, $CDCl_3$): δ 8.48 (s, 1H, $H_3$), 4.74 (s, 2H, $H_4$), 4.46 (q, J=7.1 Hz, 2H, $H_2$), 1.41 (t, J=7.2 Hz, 3H, $H_1$). $^{13}$C NMR (126 MHz, $CDCl_3$): δ 188.4 (C), 159.1 (C), 159.0 (C), 153.3 (C), 131.1 (CH), 63.2 ($CH_2$), 56.4 ($CH_2$), 14.2 ($CH_3$). IR (ATR-FTIR), $cm^{-1}$: 3102 (w), 3015 (m), 2995 (m), 2975 (m), 2958 (m), 2258 (w), 2102 (s), 1737 (s), 1704 (s), 1412 (m), 1249 (m), 1081 (s), 938 (m). HRMS-CI (m/z): $[M+H]^+$ calcd for $C_8H_9N_4O_3S$ 241.0395; found, 241.0386.

Synthesis of the Carbamate S22

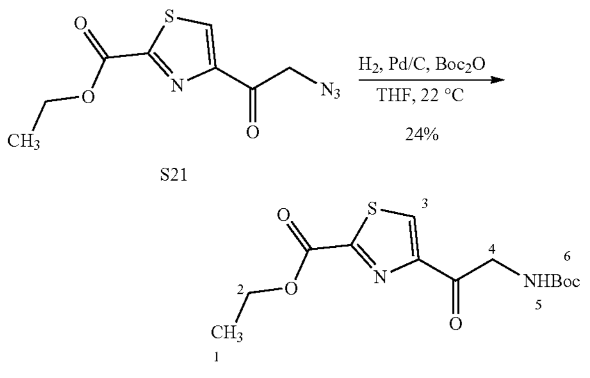

S21 S22

Palladium on carbon (10 wt %, 45.3 mg, 42.6 μmol, 0.02 equiv) was added to a solution of the α-azido ketone S21 (453 mg, 1.89 mmol 1.00 equiv) in tetrahydrofuran (6.3 mL) at 22° C. The reaction vessel was transferred to a stainless-steel hydrogenation apparatus. The apparatus was pressurized with dihydrogen (1,000 psi) at 22° C., sealed, and the reaction mixture was stirred for 1 h at 22° C. The apparatus was then carefully depressurized. The product mixture was filtered through Celite and the Celite pad was rinsed with ethyl acetate (50 mL). The filtrates were combined and the combined filtrates were concentrated. The residue obtained was purified by automated flash-column chromatography (eluting with 5% ethyl acetate-hexanes initially, grading to 55% ethyl acetate-hexanes, linear gradient) to afford the carbamate S22 as a colorless oil (149.3 mg, 24%).

$R_f$=0.23 (30% ethyl acetate hexanes; UV). $^1$H NMR (400 MHz, $CDCl_3$): δ 8.44 (s, 1H, $H_3$), 5.32 (s, 1H, $H_5$), 4.81 (d, J=5.2 Hz, 2H, $H_4$), 4.50 (q, J=7.1 Hz, 2H, $H_2$), 1.47 (s, 9H, $H_6$), 1.46 (t, J=7.1 Hz, 3H, $H_1$). $^{13}$C NMR (126 MHz, $CDCl_3$): δ 190.1 (C), 159.48 (C), 159.2 (C), 155.8 (C), 153.9 (C), 130.7 (CH), 79.9 (C), 63.2 ($CH_2$), 49.2 ($CH_2$), 28.5 (3×$CH_3$), 14.3 ($CH_3$). IR (ATR-FTIR), $cm^{-1}$: 3400 (w), 2979 (m), 2930 (w), 2111 (w), 1297 (s), 1506 (s), 1482 (s), 1246 (s), 1156 (s) 1083 (s), 1011 (m), 855 (m), 856 (m), 734 (m). HRMS-CI (m/z): $[M+Na]^+$ calcd for $C_{13}H_{18}N_2NaO_5S$, 337.0834; found 337.0847.

Synthesis of the Ammonium Ion S25

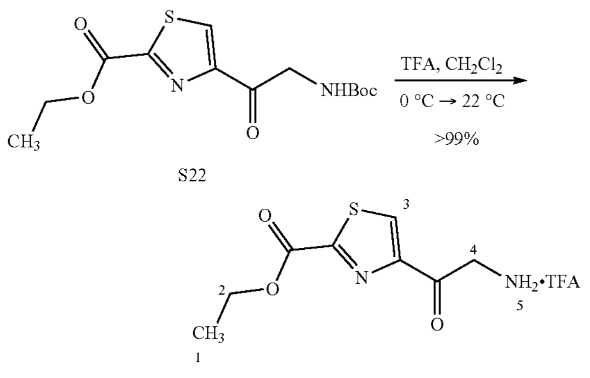

S22 S25

Trifluoroacetic acid (2.10 mL, 27.4 mmol, 200 equiv) was added to a solution of the thiazole S22 (43.1 mg, 137 μmol, 1.00 equiv) in dichloromethane (1.1 mL) at 0° C. The reaction mixture was stirred for 5 min at 0° C. The cooling bath was then removed and the reaction mixture was allowed to warm to 22° C. over 10 min. The reaction mixture was stirred for 1 h at 22° C. The product mixture was concentrated under a stream of nitrogen to provide the ammonium salt S25 as an orange oil (42.6 mg, >99%). The ammonium ion S25 obtained in this way judged to be >95% purity ($^1$H NMR analysis) and was used without further purification.

$R_f$=Compound has no mobility on silica. $^1$H NMR (600 MHz, $CD_2Cl_2$): δ 8.69 (s, 1H, $H_3$), 8.52 (s, 3H, $H_5$), 4.87 (s, 2H, $H_4$), 4.45 (q, J=7.1 Hz, 2H, $H_2$), 1.40 (t, J=7.1 Hz, 3H, $H_1$). $^{13}$C NMR (151 MHz, $CD_2Cl_2$): δ 187.3 (C), 159.8 (C), 159.6 (C), 152.4 (C), 133.8 (CH), 64.1 ($CH_2$), 47.2 ($CH_2$), 14.4 ($CH_3$). IR (ATR-FTIR), $cm^{-1}$: 2991 (w), 1708 (s), 1670 (s), 1483 (m), 1424, (m), 1370 (m), 1261 (m), 1160 (s), 1131 (s), 1089 (s), 1004 (m), 910 (m), 854 (m), 835 (m), 789 (m), 760 (w), 722 (m), 597 (w), 519 (w). HRMS-CI (m/z): $[M+H]^+$ calcd for $C_8H_{11}N_2O_3S$ 215.0485; found, 215.0495.

Synthesis of the Vinylogous Imide S24

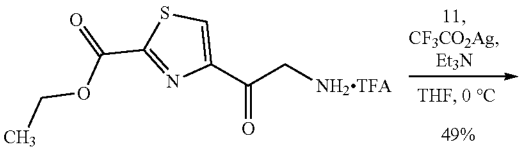

S25

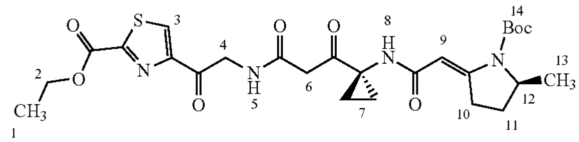

S24

Triethylamine (101 μL, 730 μmol, 4.00 equiv) was added dropwise via syringe to a solution of the ammonium salt S25 (72.0 mg, 219 μmol, 1.20 equiv) and the β-ketothioester 11 (80.0 mg, 182 μmol, 1.00 equiv) in tetrahydrofuran (4.3 mL) at 0° C. The reaction vessel was then wrapped in aluminum foil. A solution of silver trifluoroacetate (81.0 mg, 365 μmol, 2.00 equiv) in tetrahydrofuran (1.8 mL) was then added dropwise over 3 min via syringe at 0° C. The reaction mixture was stirred for 30 min at 0° C., with protection from light. The product mixture was diluted sequentially with ethyl acetate (5.0 mL) and saturated aqueous ammonium chloride solution (5.0 mL). The resulting biphasic mixture was filtered through Celite. The Celite pad was rinsed with ethyl acetate (20 mL). The filtrates were collected and combined and the combined filtrates were transferred to a separatory funnel. The layers that formed were separated, and the aqueous layer was extracted with ethyl acetate (3×5.0 mL). The organic layers were combined and the combined organic layers were washed with saturated aqueous sodium chloride solution (3.0 mL). The washed organic layer was dried over sodium sulfate. The dried solution was filtered and the filtrate was concentrated. The residue obtained was purified by automated flash-column chromatography (eluting with hexanes initially, grading to 100% ethyl acetate-hexanes, linear gradient) to afford the vinylogous imide S24 as a white solid (60 mg, 59%).

$R_f$=0.40 (100% ethyl acetate; UV). $^1$H NMR (600 MHz, $CD_2Cl_2$) δ 8.48 (s, 1H, $H_3$), 7.56 (t, J=5.1 Hz, 1H, $H_5$), 6.53 (s, 1H, $H_8$), 6.50 (s, 1H, $H_9$), 4.84 (d, J=5.1 Hz, 2H, $H_4$), 4.48 (q, J=7.1 Hz, 2H, $H_2$), 4.23 (p, J=6.6 Hz, 1H, $H_{12}$), 3.66 (s, 2H, $H_6$), 3.53 (ddt, J=18.3, 8.8, 1.6 Hz, 1H, $H_{10a}$), 3.00-2.89 (m, 1H, $H_{10b}$), 1.99-1.91 (m, 1H, $H_{11a}$), 1.64-1.58 (m, 1H, $H_{11b}$), 1.46 (s, 9H, $H_{14}$), 1.44 (t, J=7.1 Hz, 3H, $H_1$), 1.19 (d, J=6.4 Hz, 3H, $H_{13}$), 1.15 (q, J=2.8, 1.9 Hz, 2H, $H_7$). $^{13}$C NMR (151 MHz, $CD_2Cl_2$) δ 206.4 (C), 189.9 (C), 170.2 (C), 167.2 (C), 159.8 (C), 159.4 (C), 156.4 (C), 154.3 (C), 152.4 (C), 131.4 (CH), 97.7 (CH), 82.0 (C), 63.6 ($CH_2$), 57.4 (CH), 48.4 ($CH_2$), 46.3 ($CH_2$), 41.8 (C), 30.0 ($CH_2$), 28.9 ($CH_2$), 28.5 (3×$CH_3$), 21.6 ($CH_2$), 21.5 ($CH_2$), 19.9 ($CH_3$), 14.5 ($CH_3$). IR (ATR-FTIR), $cm^{-1}$: 3306 (w), 2978 (w), 2930 (w), 1706 (s), 1518 (m), 1482 (m), 1367 (m), 1291 (s), 1250 (s), 1159 (s), 1087 (s), 1027 (m), 849 (m), 733 (m), 701 (w), 540 (w). HRMS-CI (m/z): $[M+Na]^+$ calcd for $C_{26}H_{34}N_4NaO_8S$ 585.1990; found, 585.2007.

Synthesis of the Iminium Ion S26

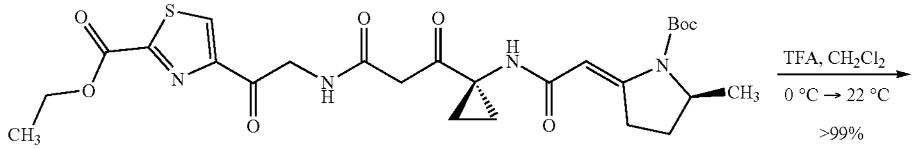

S24

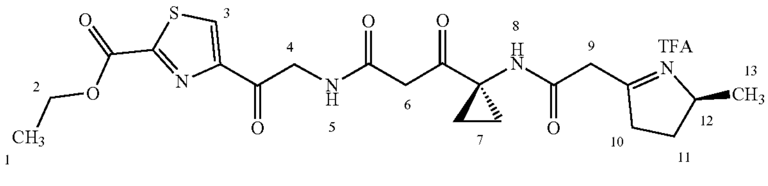

S26

Trifluoroacetic acid (273 μL, 3.56 mmol, 200 equiv) was added to a solution the vinylogous imide S24 (10 mg, 17.8 μmol, 1.00 equiv) in dichloromethane (180 μL) at 0° C. The reaction mixture was stirred for 5 min at 0° C. The cooling bath was then removed and the reaction mixture was allowed to warm to 22° C. over 10 min. The reaction mixture was stirred for 1 h at 22° C. The product mixture was concentrated under a stream of nitrogen to provide the iminium ion S26 as an orange oil (10.0 mg, >99%). The iminium ion S26 obtained in this way judged to be >95% purity ($^{1}H$ NMR analysis) and was used without further purification.

$R_f$=Compound has no mobility on silica. $^{1}H$ NMR (500 MHz, $CD_2Cl_2$) δ 8.59 (s, 1H, $H_8$), 8.51 (s, 1H, $H_3$), 8.38 (s, 1H, $H_5$), 4.88 (d, J=5.0 Hz, 2H, $H_4$), 4.59 (q, J=7.2 Hz, 1H, $H_{12}$), 4.48 (q, J=7.1 Hz, 2H, $H_2$), 3.78 (s, 2H, $H_6$), 3.33-3.18 (m, 2H, $H_{10}$), 2.55 (dtd, J=13.8, 9.1, 5.8 Hz, 1H, $H_{11a}$), 1.91 (ddt, J=13.5, 9.4, 7.1 Hz, 1H, $H_{11b}$), 1.70-1.61 (m, 2H, $H_{7a}$), 1.50 (d, J=6.5 Hz, 3H, $H_{13}$), 1.43 (t, J=7.1 Hz, 3H, $H_1$), 1.31-1.20 (m, 2H, $H_{7b}$). $^{13}C$ NMR (126 MHz, $CD_2Cl_2$) δ 204.5 (C), 190.7 (C), 189.4 (C), 167.9 (C), 159.8 (C), 159.7 (C), 153.7 (C), 132.1 (CH), 131.8 (C), 64.5 (CH), 63.8 ($CH_2$), 48.6 ($CH_2$), 45.3 ($CH_2$), 42.1 ($CH_2$), 38.7 ($CH_2$), 37.9 (C), 30.2 ($CH_2$), 28.2 ($CH_2$), 21.1 ($CH_2$), 19.9 ($CH_3$), 14.48 ($CH_3$). IR (ATR-FTIR), $cm^{-1}$: 2927 (w), 1785 (m), 1640 (s), 1462 (m), 1350 (m), 1258 (m), 1170 (s), 1092 (m), 1015 (m), 798 (m), 721 (m). HRMS-CI (m/z): $[M+Na]^+$ calcd for $C_{21}H_{27}N_4NaO_6S$ 485.1465; found, 485.1479.

Synthesis of the Electrophile 24

$H_{4b}$*, $H_{6a}$), 3.36-3.28 (m, 1H, $H_{6a}$*), 2.76 (dddd, J=18.0, 9.8, 4.5, 2.2 Hz, 1H, $H_{6b}$), 2.57 (dtd, J=18.0, 9.2, 2.4 Hz, 1H, $H_{6b}$*), 2.30-2.18 (m, 2H, $H_{7a}$, $H_{7a}$*), 1.58-1.50 (m, 2H, $H_{7b}$, $H_{7b}$*), 1.48-1.38 (m, 7H, $H_1$, $H_1$*, and either $H_{10a}$ or $H_{10a}$*), 1.38-1.27 (m, 7H, $H_9$, $H_9$*, and either $H_{10a}$ or $H_{10a}$*), 1.03 (dtd, J=10.4, 8.1, 5.6 Hz, 2H, $H_{10b}$, $H_{10b}$*), 0.98-0.82 (m, 2H, $H_{10c}$, $H_{10c}$*), −0.31 (ddd, J=10.7, 8.2, 5.6 Hz, 2H, $H_{10d}$, $H_{10d}$*). $^{13}C$ NMR (151 MHz, $CD_3OD$) δ 174.4 (C), 173.8 (C), 172.5 (C), 172.2 (C), 172.1 (C), 172.0 (C), 162.2 (C), 162.0 (C), 160.9 (C), 160.8 (C), 159.7 (C), 159.6 (C), 158.1 (C), 157.2 (C), 133.1 (C), 132.9 (C), 124.6 (CH), 124.5 (CH), 81.9 (C), 81.8 (C), 68.5 (CH), 66.8 (C), 63.9 (2×$CH_2$), 58.4 ($CH_2$), 58.3 ($CH_2$), 52.6 (CH), 52.5 (CH), 47.6 (C), 47.5 (C), 37.6 ($CH_2$), 37.1 ($CH_2$), 31.7 ($CH_2$), 21.8 ($CH_3$), 21.5 ($CH_3$), 14.5 (2×$CH_3$), 13.0 ($CH_2$), 12.9 ($CH_2$), 11.2 ($CH_2$), 11.0 ($CH_2$). IR (ATR-FTIR), $cm^{-1}$: 3227 (br w), 2926 (m), 2362 (m), 1696 (s), 1677 (s), 1467 (m), 1298 (m), 1258 (m), 1172 (m), 1089 (m), 794 (w). HRMS-CI (m/z): $[M+NaN]^+$ calcd for $C_{21}H_{24}N_4NaO_5S$ 467.1360; found, 467.1372.

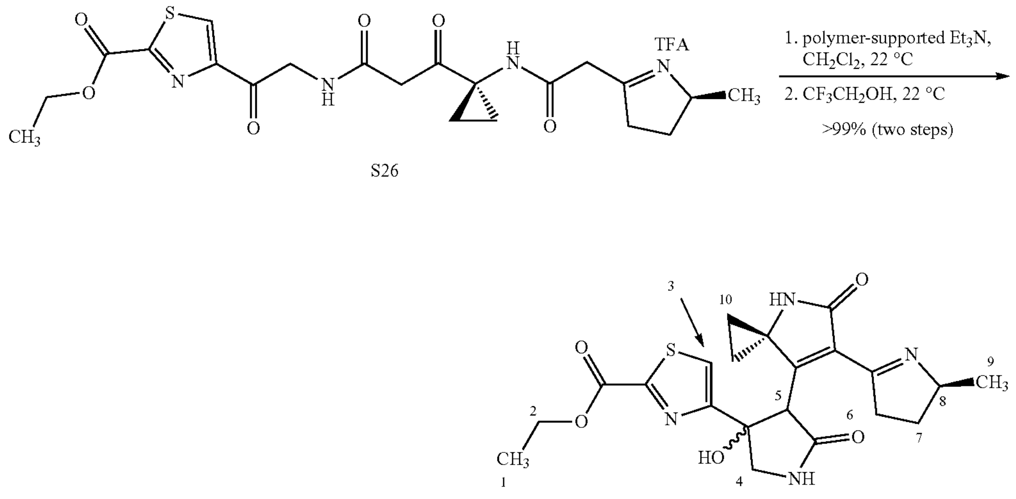

S26

24

Polymer-supported triethylamine (178 mg, 178 μmol triethylamine, 10.0 equiv) was added to a solution of S26 (nominally 17.8 μmol, 1.00 equiv) in dichloromethane (2.0 mL) at 22° C. The heterogenous mixture was stirred for 10 min at 22° C. The product mixture was filtered through a pad of Celite. The Celite pad was washed with dichloromethane (5.0 mL). The filtrates were collected and combined. The combined filtrates were concentrated.

The resulting residue obtained in the preceding step was dissolved in 2,2,2-trifluoroethanol (1.0 mL) at 22° C. and the resulting solution incubated at 22° C. for 10 min. The product mixture was concentrated to provide the electrophile 24 as a white solid (7.9 mg, >99%). The product was formed as an 1:1.3 mixture of C5 diasteromers. The electrophile 24 obtained in this way judged to be >95% purity ($^{1}H$ NMR analysis) and was used without further purification.

$R_f$=Compound has no mobility on silica. $^{1}H$ NMR (600 MHz, $CD_3OD$, C41 1,2-addition product diastereomers, minor diastereomer denoted by *) δ 7.92 (s, 1H, $H_3$*), 7.91 (s, 1H, $H_3$), 4.48 (q, J=7.1 Hz, 4H, $H_2$, $H_2$*), 4.26-4.20 (m, 1H, $H_8$), 4.10 (d, J=10.8 Hz, 1H, $H_{4a}$), 4.07 (d, J=10.8 Hz, 1H, $H_{4a}$*), 4.06-4.01 (m, 1H, $H_8$*), 3.79 (s, 1H, $H_5$*), 3.78 (s, 1H, $H_5$), 3.50 (d, J=10.8 Hz, 1H, $H_{4b}$), 3.50-3.42 (m, 2H,

Enumerated Embodiments

In some aspects, the present invention is directed to the following non-limiting embodiments:

Embodiment 1: A compound of Formula (I): A1-B-A2 (I), wherein A1 and A2 are each independently selected from the group consisting of

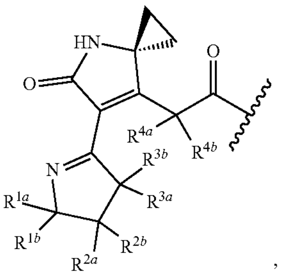

,

-continued

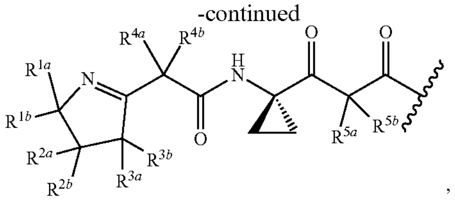

, and

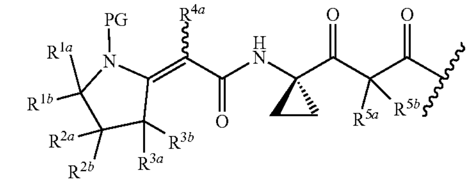

wherein B is a bifunctional group selected from the group consisting of:

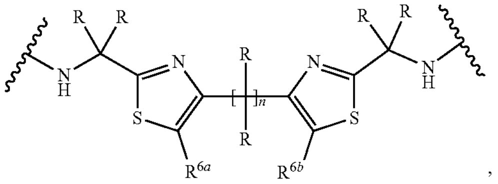

,

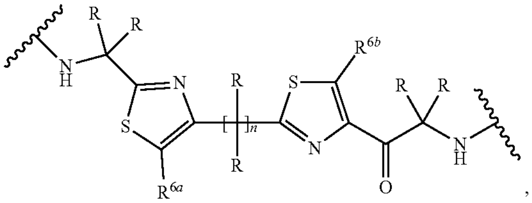

,

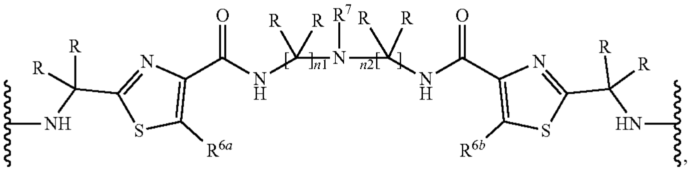

,

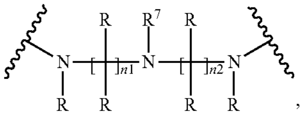

, and

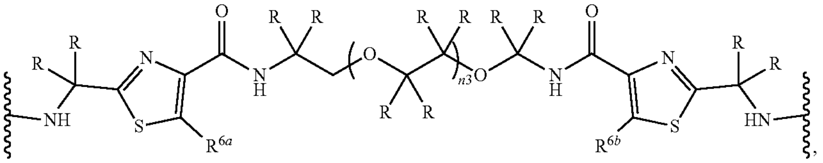

, wherein each occurrence of $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl;

wherein $R^7$ is selected from the group consisting of hydrogen, optionally substituted $C_1$-$C_6$ alkyl, optionally substituted $C_3$-$C_6$ cycloalkyl, optionally substituted $C_2$-$C_6$ cycloalkenyl, and optionally substituted $C_2$-$C_6$ cycloalkynyl;

wherein PG is a protective group selected from the group consisting of tert-butoxycarbonyl (Boc), trityl, dimethoxytrityl, tert-butyldimethylsilyl (TBDMS), carboxybenzyl (Cbz), nitroveratryloxycarbonyl (Nvoc), aryldithioethyloxycarbonyl (Ardec), (9H-fluoren-9-yl) methyl ((S)-1-(((S)-1-((4-(hydroxymethyl)phenyl) amino)-1-oxo-5-ureidopentan-2-yl) amino)-3-methyl-1-oxobutan-2-yl) carbamate (Fmoc-Val-Cit-PAB) and derivates thereof;

each occurrence of R is independently H and optionally substituted $C_1$-$C_6$ alkyl;

wherein each occurrence of n, n1, and n2 is independently an integer ranging from 2 to 6; and wherein each occurrence of n3 is independently an integer ranging from 1 to 6;

or a salt, solvate, isotopically labelled derivative, stereoisomer, tautomer, or geometric isomer thereof, or a mixture thereof.

Embodiment 2: The compound of Embodiment 1, wherein A1 and A2 are each independently selected from the group consisting of

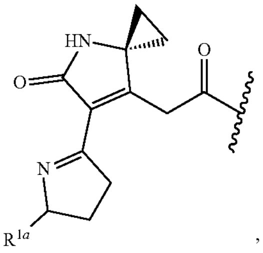

,

-continued

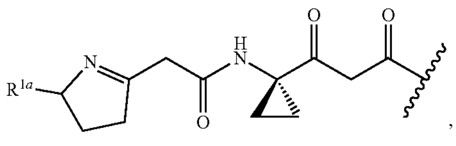

, and

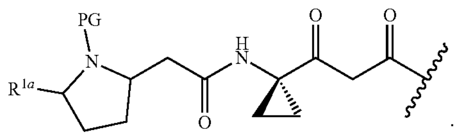

.

Embodiment 3: The compound of Embodiment 1, wherein A1 and A2 are each independently selected from the group consisting of:

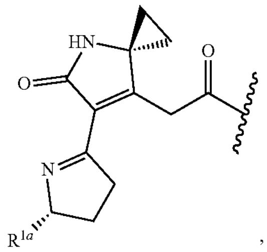
,
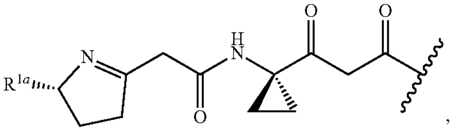
, and
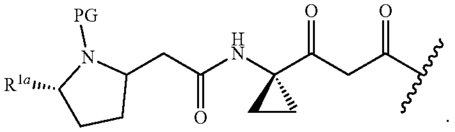
.
Embodiment 4: The compound of Embodiment 1, wherein A is
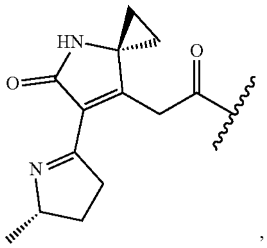
,
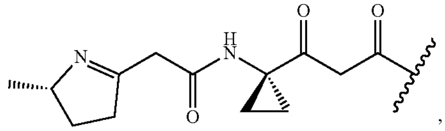
, or
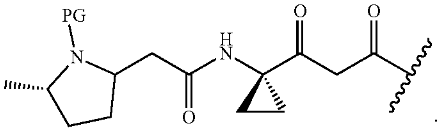
.
Embodiment 5: The compound of claim 1, which is at least one selected from the group consisting of:
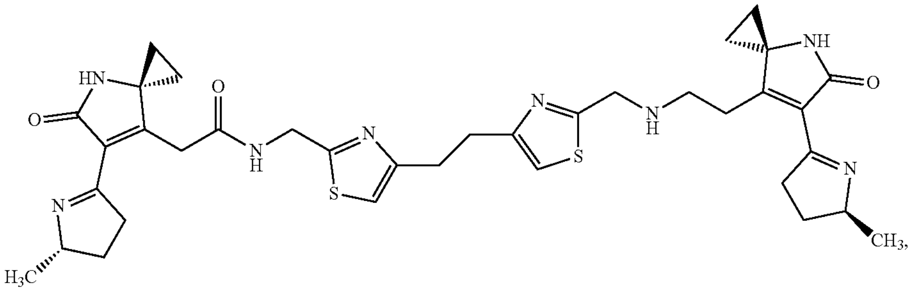
,
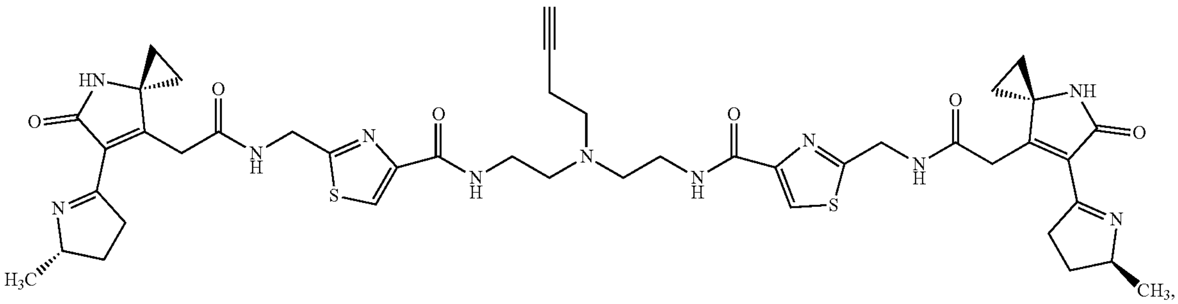
,
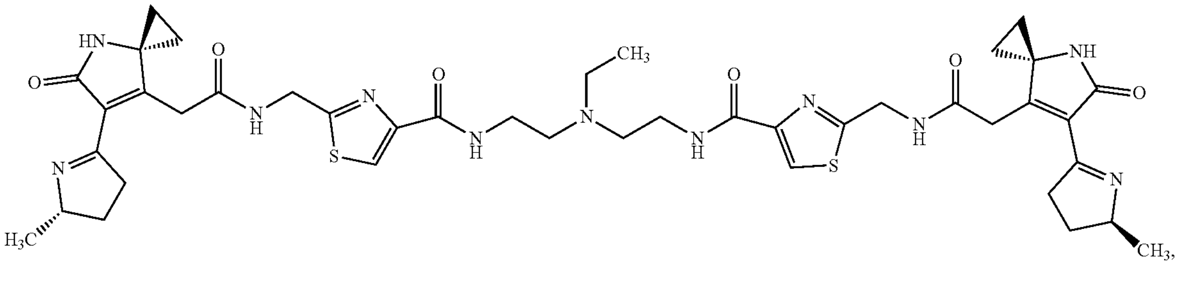
, -continued

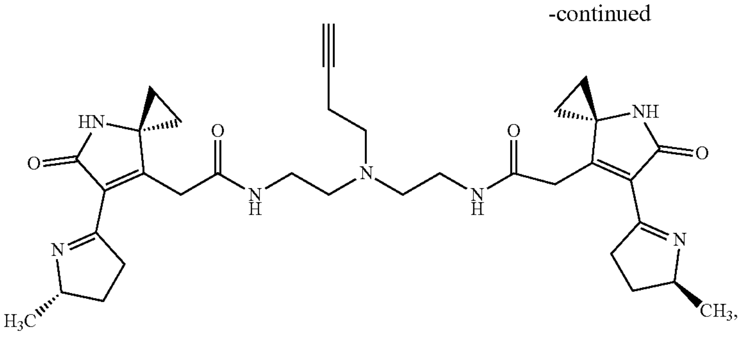

and

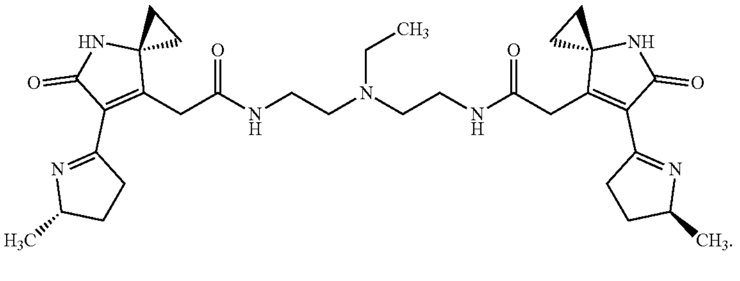

Embodiment 6: The compound of Embodiment 1, which is capable of alkylating a DNA molecule.

Embodiment 7: The compound of Embodiment 1, which is capable of forming an interstrand cross-link in a DNA molecule.

Embodiment 8: A compound of Formula (II):

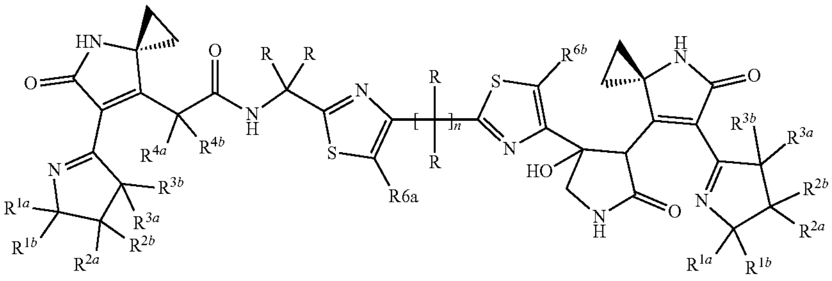

wherein each occurrence of $R^{1a}$, $R^{1b}$, $R^{2a}$, $R^{2b}$, $R^{3a}$, $R^{3b}$, $R^{4a}$, $R^{4b}$, $R^{6a}$, and $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl;

each occurrence of R is independently H and optionally substituted $C_1$-$C_6$ alkyl; and wherein n is independently an integer ranging from 2 to 6;

or a salt, solvate, isotopically labelled derivative, stereoisomer, tautomer, or geometric isomer thereof, and any mixtures thereof.

Embodiment 9: The compound of Embodiment 8, wherein the compound is

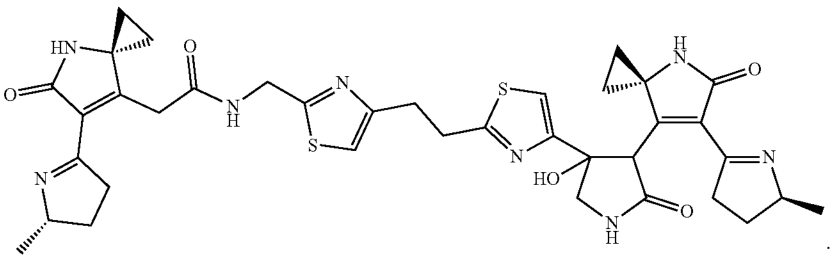

.

Embodiment 10: A method of alkylating a DNA molecule, the method comprising contacting the DNA molecule with the compound of Embodiment 1, or a salt, solvate, isotopically labelled derivative, stereoisomer, tautomer, or geometric isomer, or mixtures thereof.

Embodiment 11: The method of Embodiment 10, wherein alkylating the DNA molecule comprising forming a DNA interstrand cross-link in the DNA molecule.

Embodiment 12: The method of Embodiment 10, wherein the contacting is performed at a pH ranging from about 5.0 to 7.0.

Embodiment 13: The method of Embodiment 10, wherein the DNA molecule is genomic DNA of a cell in a nucleus of the cell.

Embodiment 14: The method of Embodiment 13, wherein the cell is a cancer cell.

Embodiment 15: A method of preventing, treating, and/or ameliorating cancer in a subject in need thereof, the method comprising administering to the subject an effective amount of the compound of Embodiment 1, or a salt, solvate, isotopically labelled derivative, stereoisomer, tautomer, or geometric isomer, or mixtures thereof.

Embodiment 16: The method of Embodiment 15, wherein the compound is administered as a pharmaceutical composition comprising a pharmaceutically acceptable carrier.

Embodiment 17: The method of Embodiment 15, wherein the cancer comprises at least one of cervical cancer, breast cancer, urinary tract cancer, and gastrointestinal cancer.

The foregoing outlines features of several embodiments so that those skilled in the art may better understand the aspects of the instant specification. Those skilled in the art should appreciate that they may readily use the instant specification as a basis for designing or modifying other processes and structures for carrying out the same purposes and/or achieving the same advantages of the embodiments introduced herein. Those skilled in the art should also realize that such equivalent constructions do not depart from the spirit and scope of the instant specification, and that they may make various changes, substitutions, and alterations herein without departing from the spirit and scope of the instant specification.

What is claimed is:

1. A compound of Formula (I):

A1-B-A2 (I), wherein A1 and A2 are each independently selected from the group consisting of

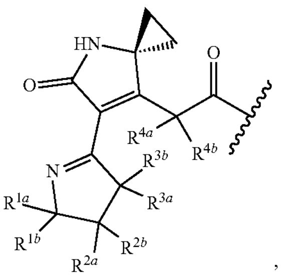

,

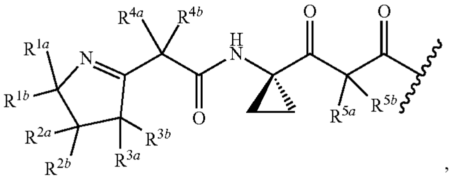

, and

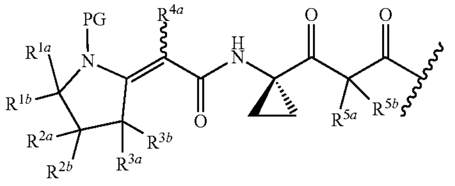

wherein B is a bifunctional group selected from the group consisting of:

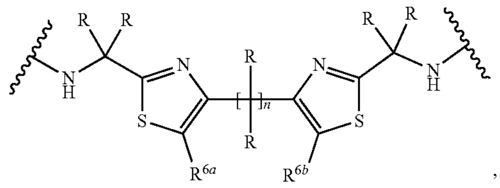

,

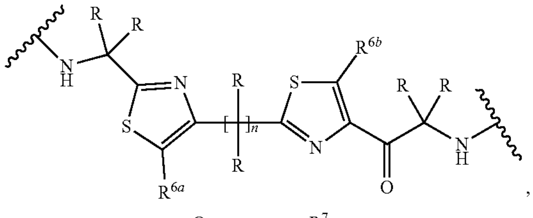

,

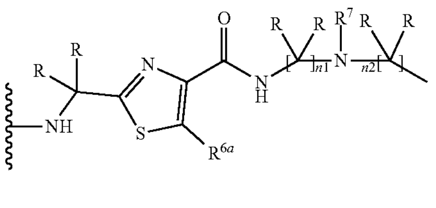

-continued

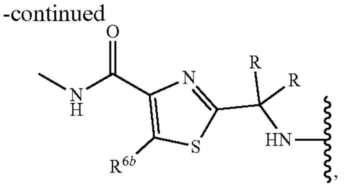,

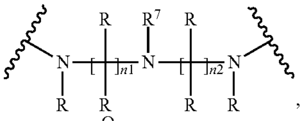

, and

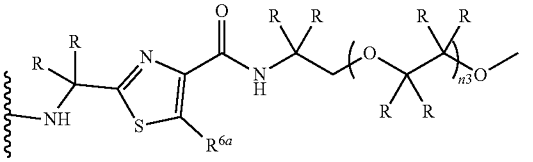

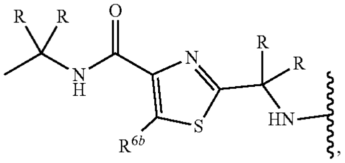, wherein each occurrence of $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl;

wherein $R^7$ is selected from the group consisting of hydrogen, optionally substituted $C_1$-$C_6$ alkyl, optionally substituted $C_3$-$C_6$ cycloalkyl, optionally substituted $C_2$-$C_6$ cycloalkenyl, and optionally substituted $C_2$-$C_6$ cycloalkynyl;

wherein PG is a protective group selected from the group consisting of tert-butoxycarbonyl (Boc), trityl, dimethoxytrityl, tert-butyldimethylsilyl (TBDMS), carboxybenzyl (Cbz), nitroveratryloxycarbonyl (Nvoc), aryldithioethyloxycarbonyl (Ardec), and (9H-fluoren-9-yl) methyl ((S)-1-(((S)-1-((4-(hydroxymethyl) phenyl) amino)-1-oxo-5-ureidopentan-2-yl) amino)-3-methyl-1-oxobutan-2-yl) carbamate (Fmoc-Val-Cit-PAB);

each occurrence of R is independently H and optionally substituted $C_1$-$C_6$ alkyl;

wherein each occurrence of n, n1, and n2 is independently 2, 3, 4, 5, or 6; and wherein each occurrence of n3 is independently 1, 2, 3, 4, 5, or 6;

or a salt, solvate, isotopically labelled derivative, stereoisomer, tautomer, or geometric isomer thereof, or a mixture thereof.

2. The compound of claim 1, wherein A1 and A2 are each independently selected from the group consisting of

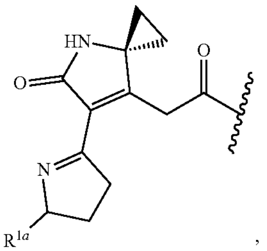

,

-continued

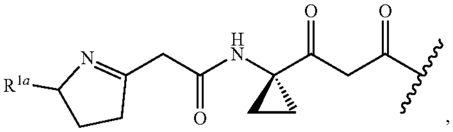

, and

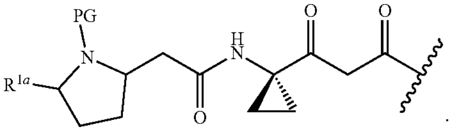

.

3. The compound of claim 1, wherein A1 and A2 are each independently selected from the group consisting of:

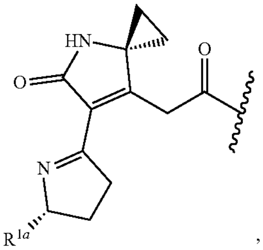

,

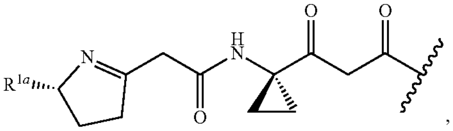

, and

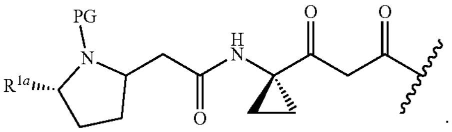

.

4. The compound of claim 1, wherein A1 or A2 are each independently selected from the group consisting of:

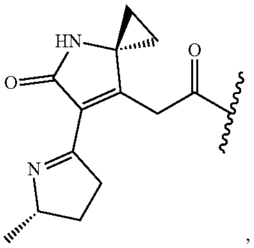

,

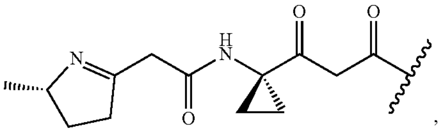

, and

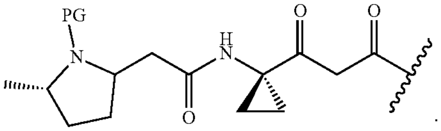

.

5. The compound of claim 1, which is capable of alkylating a DNA molecule.

6. The compound of claim 1, which is capable of forming an interstrand cross-link in a DNA molecule.

7. A method of alkylating a DNA molecule, the method comprising contacting the DNA molecule with the compound of claim 1, or a salt, solvate, isotopically labelled derivative, stereoisomer, tautomer, or geometric isomer, or mixtures thereof.

8. The method of claim 7, wherein alkylating the DNA molecule comprising forming a DNA interstrand cross-link in the DNA molecule.

9. The method of claim 7, wherein the contacting is performed at a pH ranging from about 5.0 to 7.0.

10. The method of claim 7, wherein the DNA molecule is genomic DNA of a cell in a nucleus of the cell.

11. The method of claim 10, wherein the cell is a cancer cell.

12. A method of treating or ameliorating cancer in a subject in need thereof, the method comprising administering to the subject an effective amount of the compound of claim 1, or a salt, solvate, isotopically labelled derivative, stereoisomer, tautomer, or geometric isomer, or mixtures thereof.

13. The method of claim 12, wherein the compound is administered as a pharmaceutical composition comprising a pharmaceutically acceptable carrier.

14. The method of claim 12, wherein the cancer comprises at least one of cervical cancer, breast cancer, urinary tract cancer, and gastrointestinal cancer.

15. A compound of Formula (II):

(II)

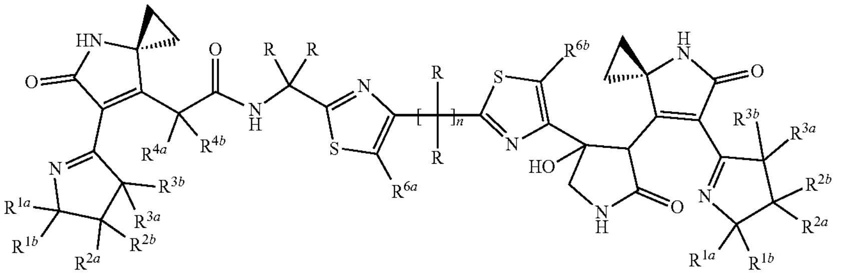

.

wherein each occurrence of $R^{1a}$, $R^{1b}$, $R^{2a}$, $R^{2b}$, $R^{3a}$, $R^{3b}$, $R^{4a}$, $R^{4b}$, $R^{6a}$, and $R^{6b}$ is independently selected from the group consisting of hydrogen, deuterium, halogen, optionally substituted $C_1$-$C_6$ alkoxy, optionally substituted $C_1$-$C_6$ alkyl, and optionally substituted $C_3$-$C_6$ cycloalkyl;

each occurrence of R is independently H and optionally substituted $C_1$-$C_6$ alkyl; and wherein n is independently 2, 3, 4, 5, or 6;

or a salt, solvate, isotopically labelled derivative, stereoisomer, tautomer, or geometric isomer thereof, and any mixtures thereof.

16. The compound of claim 15, wherein the compound is

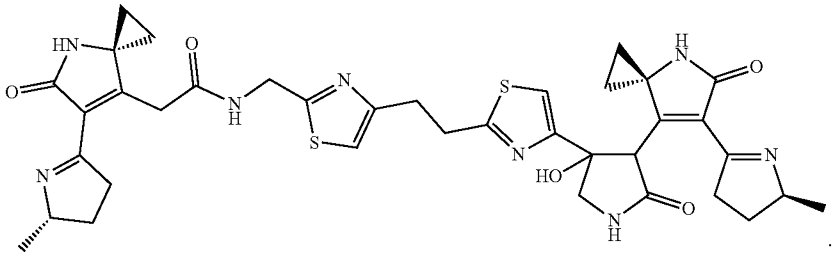

.

17. A compound selected from the group consisting of:

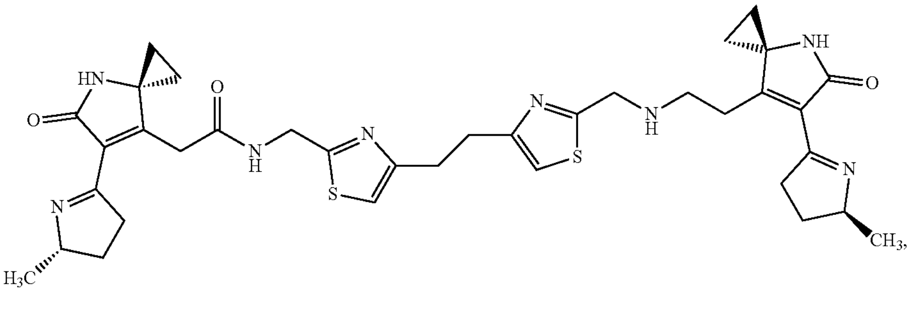

,

-continued
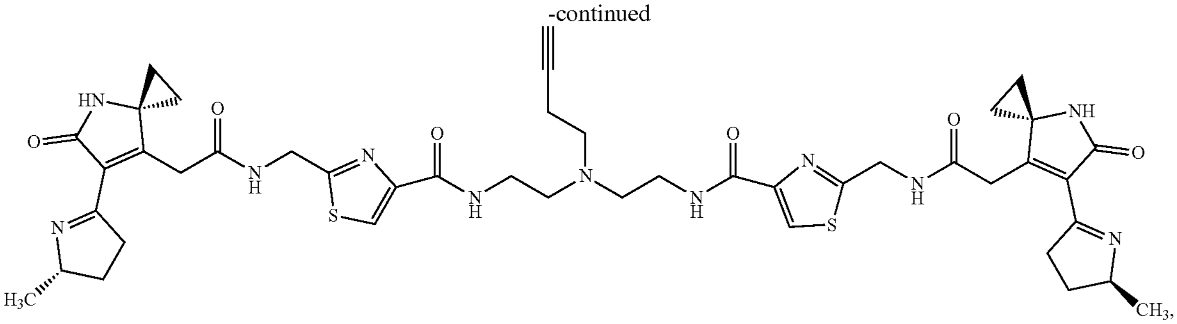
,
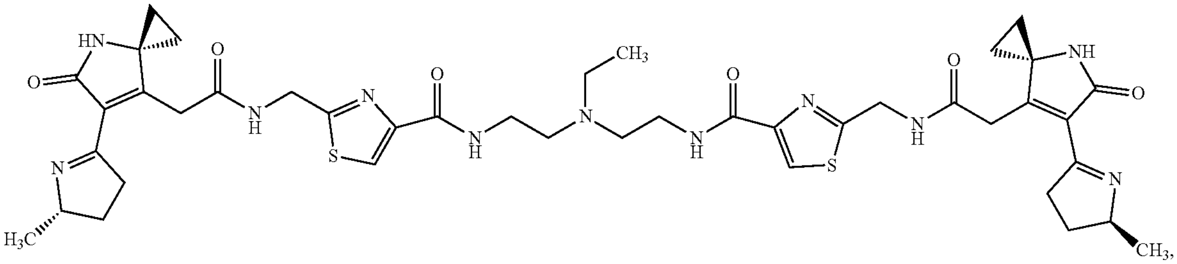
,
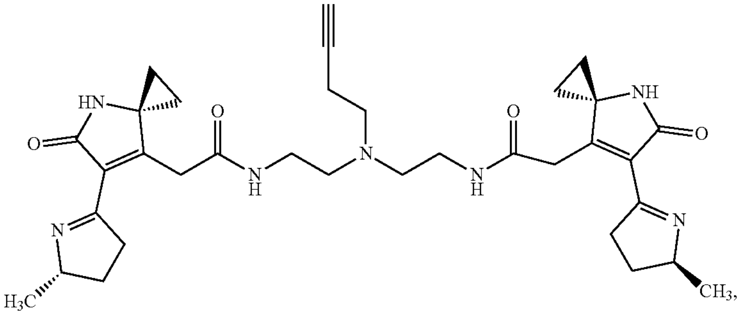
, and
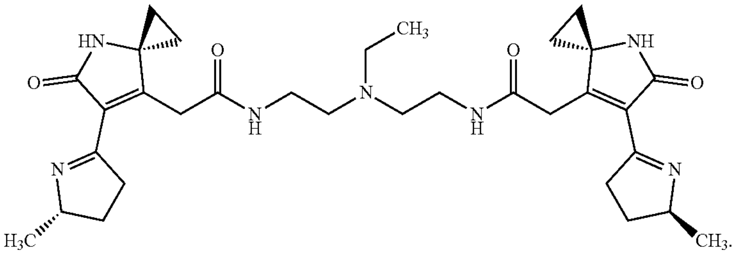
.
or a salt, solvate, isotopically labelled derivative, stereoisomer, tautomer, or geometric isomer thereof, or a mixture thereof.
* * * * *